(12) United States Patent
Hochberg et al.

(10) Patent No.: US 7,041,654 B2
(45) Date of Patent: *May 9, 2006

(54) METHODS AND COMPOSITIONS FOR INDUCING TUMOR-SPECIFIC CYTOTOXICITY

(75) Inventors: Abraham Hochberg, Jerusalem (IL); Suhail Ayesh, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 173 days.

This patent is subject to a terminal disclaimer.

(21) Appl. No.: 10/012,131

(22) Filed: Oct. 22, 2001

(65) Prior Publication Data

US 2004/0082529 A1    Apr. 29, 2004

Related U.S. Application Data

(60) Continuation-in-part of application No. 09/568,059, filed on May 10, 2000, now Pat. No. 6,306,833, which is a division of application No. 09/165,240, filed on Oct. 1, 1998, now Pat. No. 6,087,164, which is a continuation-in-part of application No. 08/943,608, filed on Oct. 3, 1997, now abandoned.

(51) Int. Cl.
*A01N 43/04*   (2006.01)
*A61K 31/70*   (2006.01)
*C07H 21/02*   (2006.01)
*C12Q 1/68*    (2006.01)
*C12N 15/00*   (2006.01)

(52) U.S. Cl. ............... 514/44; 536/23.1; 536/24.5; 435/6; 435/69.1; 435/320.1; 435/375

(58) Field of Classification Search ............ 435/6, 435/325, 475, 455, 70.1, 70.3, 320.1, 375, 435/69.1; 514/44; 536/23.1, 24.5
See application file for complete search history.

(56) References Cited

U.S. PATENT DOCUMENTS 5,998,205 A    12/1999   Hallenbeck et al.

FOREIGN PATENT DOCUMENTS

| AU | 714867 | 4/1996 |
|---|---|---|
| FR | 2725213 | 4/1996 |
| WO | WO 94/13824 | 6/1994 |
| WO | WO 95/05835 | 3/1995 |
| WO | WO 95/14101 A1 | 5/1995 |
| WO | WO 95/24503 | 9/1995 |
| WO | WO 96/05321 | 2/1996 |
| WO | WO 99/18195 A2 | 4/1999 |
| WO | WO 01/23004 A1 | 4/2001 |

OTHER PUBLICATIONS

Boccehetta et al. Epidemiology and molecular pathology at crossroads to establish causation: molecular mechanisms of malignant transformation. Aug., 2004. Oncogene (23):6484-91.*
Morris et al. Adenoviral—mediated gene transfer to bladder in vivo Aug., 1994. Journal of Urology (152):506-509.*
Webster's II new Riverside university dictionary. 1994 The Riverside Publishing Company p. 933.*
The CancerWEB Project, Published at the Dept. of Medical Oncology, University of Newcastle upon Tyne (cancerweb.ncl.ac.uk). Nov., 1997.*
Anderson, 1998, "Human gene therapy", Nature 392:25-30.
Ariel et al. 1997, "The product of the imprinted H19 gene is an oncofetal RNA", J. Clin. Pathol. Mol. Pathol. 50:34-44.
Branch, 1998, "A Good antisense molecule is hard to find", TIBS 23:45-50.
Brannan et al., 1990, "The product of the H19 gene may function as an RNA", Mol. Cell. Biol. 10:28-36.
Brunkow and Tilghman, 1991, "Ectopic expression of the H19 gene in mice causes prenatal lethality", Genes & Dev. 5:1092-1101.
Crooke, 1998, "Basic principles of antisense therapeutics", in: *Antisense Research and Application*, Cooke, ed., Springer-Verlag, pp. 1-50.
Crooke et al., 1997, "A roundtable on the state of the industry", Nature Biotechnol. 15:522.

(Continued)

*Primary Examiner*—Andrew Wang
*Assistant Examiner*—Jon B. Ashen
(74) *Attorney, Agent, or Firm*—Browdy and Neimark, PLLC

(57) ABSTRACT

The present invention relates to the tumor-specific expression of heterologous polynucleotides, particularly genes encoding cytotoxic products, under the control of transcriptional regulatory sequences. Particularly preferred transcriptional regulatory sequences comprise H19, IGF-1 and IGF-2 P4 transcriptional regulatory sequences, and variants thereof. The present invention also provides expression constructs and methods of administering such expression constructs. The compositions and methods of the invention are useful for the treatment of proliferative disorders, particularly cancer.

22 Claims, 19 Drawing Sheets

OTHER PUBLICATIONS

Figure 2:
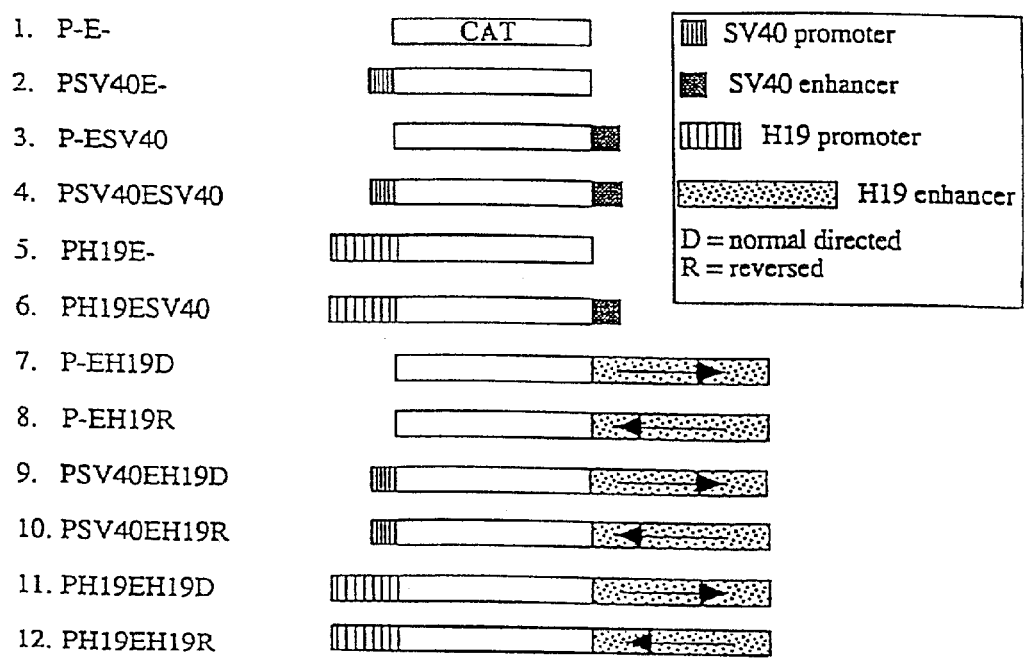

Davis et al., 1987, "Expresion of a single transfected cDNA converts fibroblasts to myoblasts", Cell 51:987-1000.

DeGroot et al., 1994, "Genetic imprinting in human embryogenesis H19 and IGF2 gene expression", Trophoblast Res. 8:285-302.

Elkin et al., 1995, "The expression of the imprinted H19 and IGF-2 genes in human bladder carcinoma", FEBS Lett. 374:57-61.

Glassman et al, 1996, "Relaxation of imprinting in carcinogenesis", Cancer Genet. Cytogenet. 89:69-73.

Gura, 1995, "Antisense has growing pains", Science 270: 575-577.

Hao et al., 1993, "Tumour-suppressor activity of H19 RNA", Nature 365:764-767.

Holthuizen et al., 1993, "Transcriptional regulation of the major promoters of the human IGF-II gene", Mol. Reprod. Dev. 35:391-393.

Hu et al., 1997, "Genomic deletion of an imprint maintenance element abolishes imprinting of both insulin-like growth factor II and H19", J. Biol. Chem. 272:20715-20720.

Huber et al., 1991, "Retroviral—mediated gene therapy for the treatment of hepatocellular carcinoma: an innovative approach for cancer therapy", Proc. Natl. Acad. Sci. USA 88:8039-8043.

Hurst et al., 1996, "Imprinted genes have few small introns", Nature Genetics 12:234-237.

Kaneko et al. 1995, "Adenovirus—mediated gene therapy of hepatocellular carcinoma using cancer-specific gene expression", Cancer Res. 55:5283-5287.

Leighton et al., 1995, "Disruption of imprinting caused by deletion of the *H19* gene region in mice", Nature 375:34-39.

Lustig-Yariv et al., 1997, "The expression of the imprinted genes H19 and IGF-2 in choriocarcinoma cell lines. Is H19 a tumor suppressor gene?", Oncogene 15:169-177.

Ogawa et al., 1993, "Relaxation of insulin-like growth factor II gene imprinting implicated in Wilms' tumour", Nature 362:747-749.

Orkin et al., 1995, "Report and recommendations of the panel to assess the NIH investment in research on gene therapy", pp. 1-23.

Osaki et al., 1994, "Gene therapy for carcinoembryonic antigen-producing human lung cancer cells by cell type-specific expression of herpes simplex virus thymidine kinase gene", Cancer Res. 54:5258-5261.

Pachnis et al., 1984, "Locus unlinked to α-fetoprotein under the control of the murine raf and Rif genes", Proc. Natl. Acad. Sci. USA 81:5523-5527.

Pfeiffer et al., 1996, "The structural H19 gene Is required for transgene imprinting", Proc. Natl. Acad. Sci. USA 93: 13876-13883.

Poirier et al., 1991, "The murine H19 gene is activated during embryonic stem cell differentiation *in vitro* and at the time of implantation in the developing embryo", Devel. 113:1105-1114.

Rachmilewitz et al., 1992, "Transcription of the H19 gene in differentiating cytotrophoblasts from human placenta", Mol. Reprod. Dev. 32:196-202.

Rainier et al., 1993, "Relaxation of imprinted genes in human cancer", Nature 362:747-749.

Seo et al., 1998, "Different protein-binding patterns in the P3 promoter region of the human insulin-like growth factor II gene in the human liver cirrhosis and hepatocellular carcinoma tissues", J. Korean Med. Sci. 13:171-178.

Vile et al., 1993, "Use of tissue-specific expression of the herpes simplex virus thymidine kinase gene to inhibit growth of established murine melanomas following direct intratumoral injection of DNA", Cancer Res. 53:3860-3864.

Wilkins, 1988, "Genomic imprinting and carcinogenesis", Lancet, Feb. 13;1(8581):329-31.

Xu et al., 1996, "Tissue specific growth suppression and chemosensitivity promotion in human hepatocellular carcinoma cells by retroviral—mediated transfer of the wild-type p53 gene", Hepatol. 24:1264-1268.

Alemany et al. Replicative adenoviruses for cancer therapy. Nat Biotechnol. Jul. 2000;18(7):723-7. Review.

Atencio et al. A phase 1 clinical trial of intro-arterial adenovirus p53 (SCH 58500) gene therapy for colorectal tumors metastatic to the liver. Molecular Therapy May 2001; 3(5):S309.

Burchin et al. Adenovirus—mediated regulable target gene expression in vivo. Proc Natl Acad Sci U S A. Jan. 19, 1999;96(2):355-60.

Gomez-Navarro et al. Gene therapy for cancer. Eur J Cancer. Jun. 1999;35(6):867-85. Review.

Jeremy W. Fry and Kathryn J. Wood (1999) Gene therapy: potential application in clinical transplantation. Exp. Rev. Mol. Med. Jun. 8, http://www-ermm.cbcu.cam.ac.uk/99000691h.htm.

Kusumanto et al, Phase III comparison of intramuscular delivery of ANG1 (a Vascular Endothelial Growth Factor containing plasmid) with placebo in diabetic patients with critical limb ischaemia. Molecular Therapy May 2001; 3(5): S73.

Marshall E. Gene therapy's growing pains. Science. Aug. 25, 1995;269(5227):1050, 1052-5.

Oyama et al. Intravesical and intravenous therapy of human bladder cancer by the herpes vector G207. Hum Gene Ther. Aug. 10, 2000;11(12):1683-93.

Pagliaro LC. Gene therapy for bladder cancer. World J Urol. Apr. 2000;18(2):148-51, Review.

Ramachandra et al. Re-engineering adenovirus regulatory pathways to enhance oncolytic specificity and efficacy. Nat Biotechnol. Nov. 2001;19(11):1035-41.

Ramesh et al. Successful treatment of primary and disseminated human lung cancers by systemic delivery of tumor suppressor genes using an improved liposome vector. Mol Ther. Mar. 2001;3(3):337-50.

Sayre et al. Gene therapy with systemically delivered IL-2 based plasmid/lipid complexes. Molecular Therapy May 2001; 3(5):S384.

Ayesh et al, "Inhibition of tumor growth by DT-A expressed under the control of IGF2 P3 and P4 promoter sequences", *Mol Ther* 7(4):535-541 (2003).

Holthuizen et al, "Transcriptional regulation of the major promoters of the human IGF-II gene", *Mol Reprod Dev* 35(4):391-3 (1993).

Lidor et al, "In vitro expression of the diphtheria toxin A-chain gene under the control of human chorionic gonadotropin gene promoters as a means of directing toxicity to ovarian cancer cell lines", *Am J Obstet Gynecol* 177(3):579-585 (1997).

Yee et al, "Insulin-like growth factor I expression by tumors of neuroectodermal origin with the t(11;22) chromosomal translocation. A potential autocrine growth factor", *J Clin Invest* 86(6):1806-1814 (1990).

Zhang et al,"Regulation of insulin-like growth factor II P3 promoter by p53: a potential mechanism for tumorigenesis", *Cancer Res* 56(6):1367-1373 (1996).

\* cited by examiner

```
      CTGCAGGGCCCCAACAACCCTCACCAAAGGCCAAGGTGGTGACCGACGGACCCACAGCGG
 1    ------------+---------+---------+---------+---------+---------+  60
      GACGTCCCGGGGTTGTTGGGAGTGGTTTCCGGTTCCACCACTGGCTGCCTGGGTGTCGCC
      |
-837
```

```
      GGTGGCTGGGGGAGTCGAAACTCGCCAGTCTCCACTCCACTCCCAACCGTGGTGCCCCAC
61    ---------+---------+---------+---------+---------+---------+ 120
      CCACCGACCCCCTCAGCTTTGAGCGGTCAGAGGTGAGGTGAGGGTTGGCACCACGGGGTG
```

```
      GCGGGCCTGGGAGAGTCTGTGAGGCCGCCCACCGCTTGTCAGTAGAGTGCGCCCGCGAGC
121   ---------+---------+---------+---------+---------+---------+ 180
      CGCCCGGACCCTCTCAGACACTCCGGCGGGTGGCGAACAGTCATCTCACGCGGGCGCTCG
```

```
      CGTAAGCACAGCCCGGCAACATGCGGTCTTCAGACAGGAAAGTGGCCGCGAATGGGACCG
181   ---------+---------+---------+---------+---------+---------+ 240
      GCATTCGTGTCGGGCCGTTGTACGCCAGAAGTCTGTCCTTTCACCGGCGCTTACCCTGGC
```

FIG. 1A

```
     GGGTGCCCAGCGGCTGTGGGGACTCTGTCCTGCGGAAACCGCGGTGACGAGCACAAGCTC
241  ------------+---------+---------+---------+---------+---------+ 300
     CCCACGGGTCGCCGACACCCCTGAGACAGGACGCCTTTGGCGCCACTGCTCGTGTTCGAG

GGTCAACTGGATGGGAATCGGCCTGGGGGGCTGGCACCGCGCCCACCAGGGGGTTTGCGG
301  ------------+---------+---------+---------+---------+---------+ 360
     CCAGTTGACCTACCCTTAGCCGGACCCCCCGACCGTGGCGCGGGTGGTCCCCCAAACGCC

CACTTCCCTCTGCCCCTCAGCACCCCACCCCTACTCTCCAGGAACGTGAGGTCTGAGCCG
361  ------------+---------+---------+---------+---------+---------+ 420
     GTGAAGGGAGACGGGGAGTCGTGGGGTGGGGATGAGAGGTCCTTGCACTCCAGACTCGGC

TGATGGTGGCAGGAAGGGGCCCTCTGTGCCATCCGAGTCCCCAGGGACCCGCAGCTGGCC
421  ------------+---------+---------+---------+---------+---------+ 480
     ACTACCACCGTCCTTCCCCGGGAGACACGGTAGGCTCAGGGGTCCCTGGGCGTCGACCGG

CCCAGCCATGTGCAAAGTATGTGCAGGGCGCTGGCAGGCAGGGAGCAGCAGGCATGGTGT
481  ------------+---------+---------+---------+---------+---------+ 540
     GGGTCGGTACACGTTTCATACACGTCCCGCGACCGTCCGTCCTCGTCGTCCGTACCACA

CCCCTGAGGGGAGACAGTGGTCTGGGAGGGAGAGGTCCTGGACCCTGAGGGAGGTGATGG
541  ------------+---------+---------+---------+---------+---------+ 600
     GGGGACTCCCCTCTGTCACCAGACCCTCCCTCTCCAGGACCTGGGACTCCCTCCACTACC
```

FIG. 1B

```
     GGCAATGCTCAGCCCTGTCTCCGGATGCCAAAGGAGGGGTGCGGGGAGGCCGTCTTTGGA
601  ------------+----------+----------+----------+----------+---------+ 660
     CCGTTACGAGTCGGGACAGAGGCCTACGGTTTCCTCCCCACGCCCCTCCGGCAGAAACCT

GAATTCCAGGATGGGTGCTGGGTGAGAGAGACGTGTGCTGGAACTGTCCAGGGCGGAGGT
661  ------------+----------+----------+----------+----------+---------+ 720
     CTTAAGGTCCTACCCACGACCCACTCTCTCTGCACACGACCTTGACAGGTCCCGCCTCCA

GGGCCCTGCGGGGGCCCTCGGGAGGGCCCTGCTCTGATTGGCCGGCAGGGCAGGGGCGGG
721  ------------+----------+----------+----------+----------+---------+ 780
     CCCGGGACGCCCCCGGGAGCCCTCCCGGGACGAGACTAACCGGCCGTCCCGTCCCCGCCC

AATTCTGGCGGGCCACCCCAGTTAGAAAAAGCCCGGGCTAGGACCGAGGA
781  ------------+----------+----------+----------+---------+ 830
     TTAAGACCGCCCGGTGGGGTCAATCTTTTTCGGGCCCGATCCTGGCTCCT
                  |         |                        |
                 -35       -27                       -7
```

FIG. 1C

A schematic presentation of the plasmids containing the different promoters and enhancers.

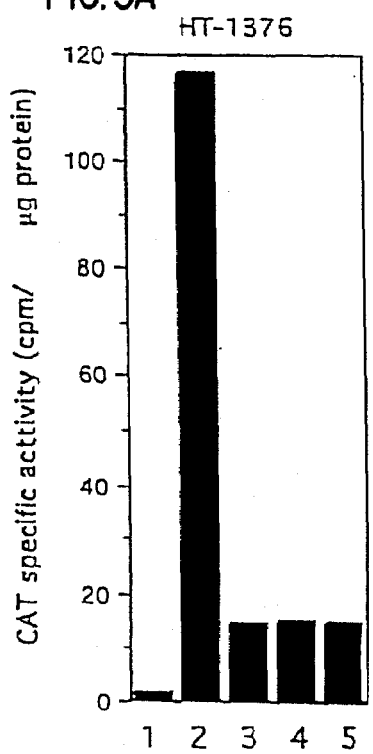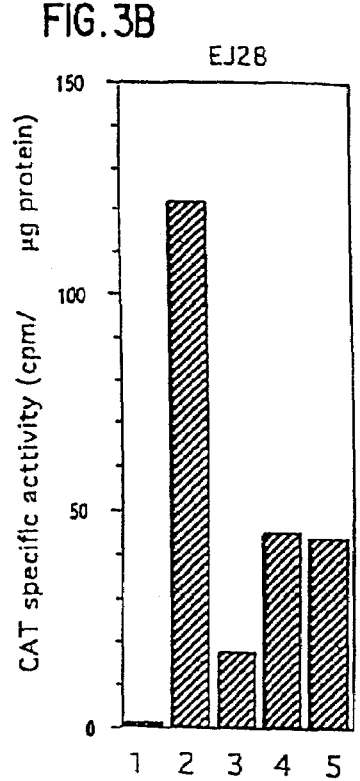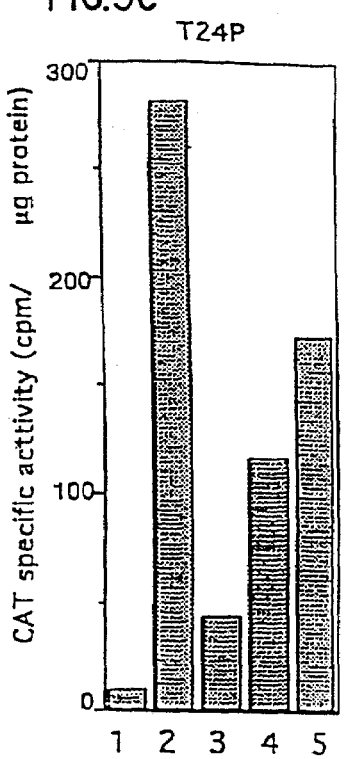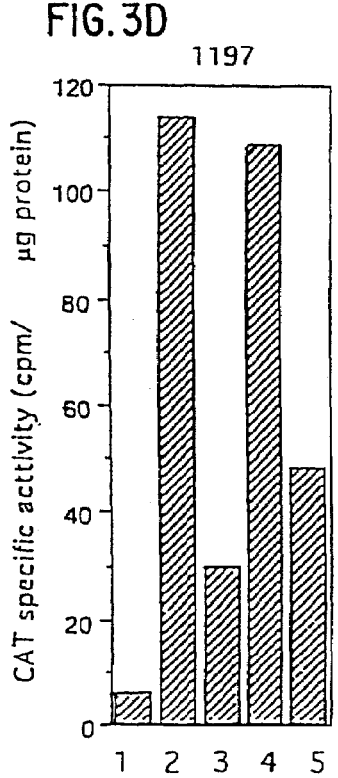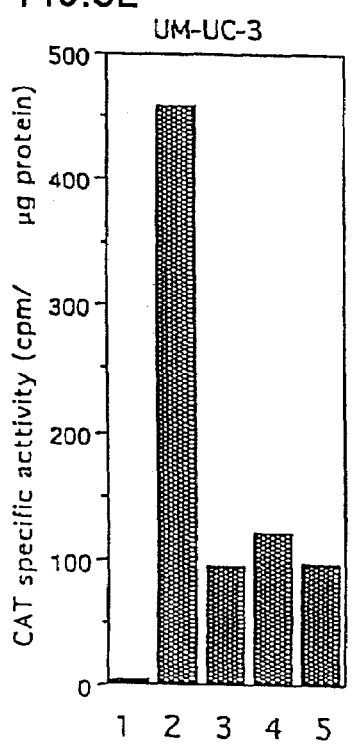

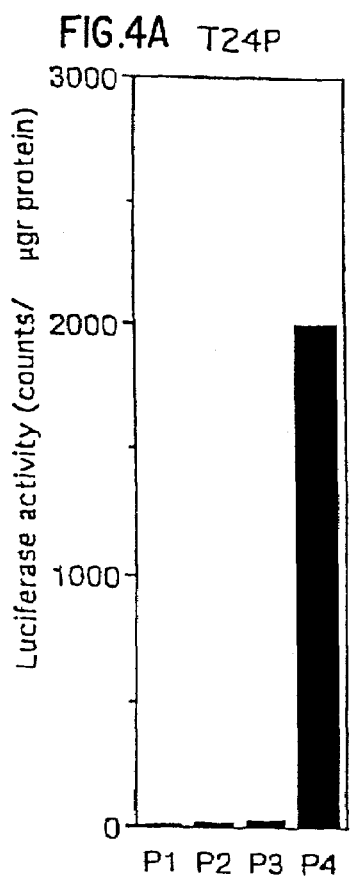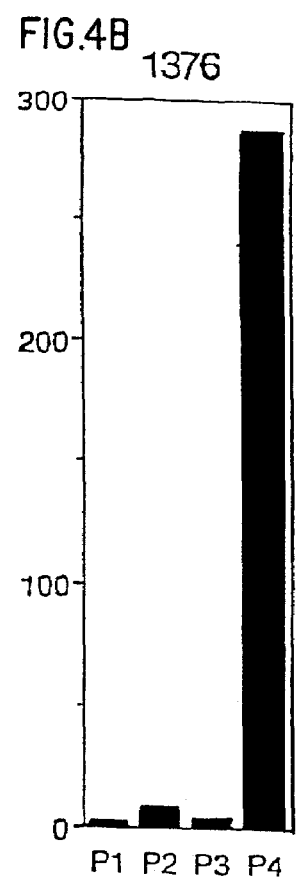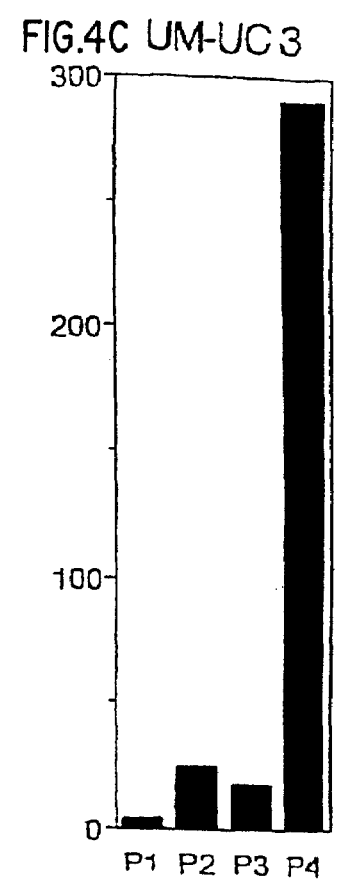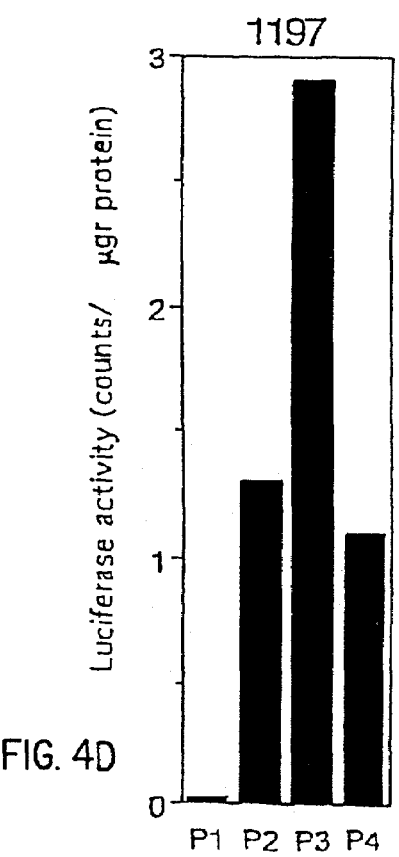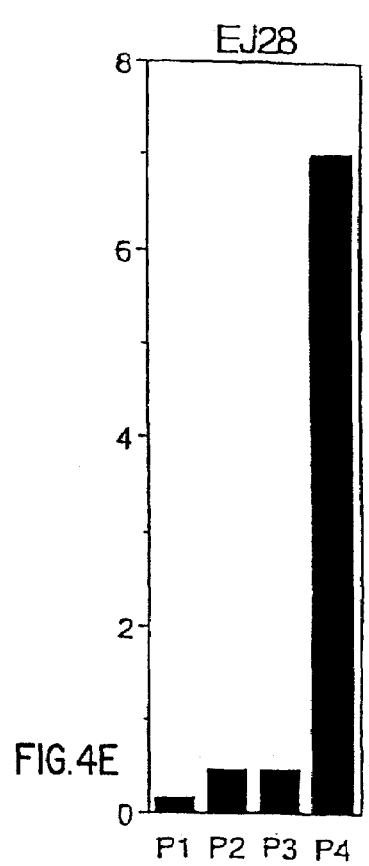

1   GACAACCCTC ACCAAGGGCC AAGGTGGTGA CCGACGGACC CACAGCGGGG
51  TGGCTGGGGG AGTCGAAACT CGCCAGTCTC CACTCCACTC CAACCGTGG
101 TGCCCCACGC GGGCCTGGGA GAGTCTGTGA GGCCGCCCAC CGCTTGTCAG
151 TAGAGTGCGC CCGCGAGCCG TAAGCACAGC CCGGCAACAT GCGGTCTTCA
201 GACAGGAAAG TGGCCGCGAA TGGGACCGGG GTGCCCAGCG GCTGTGGGGA
251 CTCTGTCCTG CGGAAACCGC GGTGACGAGC ACAAGCTCGG TCAACTGGAT
301 GGGAATCGGC CTGGGGGGCT GGCACCGCGC CACCAGGGG GTTTGCGGCA
351 CTTCCCTCTG CCCCTCAGCA CCCCACCCCT ACTCTCCAGG AACGTGAGTT
401 CTGAGCCGTG ATGGTGGCAG GAAGGGGCCC TCTGTGCCAT CCGAGTCCCC
451 AGGGACCCGC AGCTGGCCCC CAGCCATGTG CAAAGTATGT GCAGGGCGCT
501 GGCAGGCAGG GAGCAGCAGG CATGGTGTCC CCTGAGGGGA GACAGTGGTC
551 TGGGAGGGAG AAGTCCTGGC CCTGAGGGAG GTGATGGGGC AATGCTCAGC
601 CCTGTCTCCG GATGCCAAAG GAGGGGTGCG GGGAGGCCGT CTTTGGAGAA
651 TTCCAGGATG GGTGCTGGGT GAGAGAGACG TGTGCTGGAA CTGTCCAGGG
701 CGGAGGTGGG CCCTGCGGGG GCCCTCGGGA GGGCCCTGCT CTGATTGGCC
751 GGCAGGGCAG GGGCGGGAAT TCTGGGCGGG GCCACCCCAG TTAGAAAAAG
801 CCCGGGCTAG GACCGAGGAG CAGGGTGAGG GAG

FIG. 5

1   CAAGGACATG GAATTTCGGA CCTTCTGTCC CCACCCTCTC TGCTGAGCCT

51  AGGAACCTCT GAGCAGCAGG AAGGCCTTGG GTCTAGAGCC TAGAAATGGA

101 CCCCCACGTC CACCTGCCCA GCCTAGACCC CCAGCATTGA AGGGTGGTCA

151 GACTTCCTGT GAGAGGAAGC CACTAAGCGG GATGGACACC ATCGCCCACT

201 CCACCCGGCC CTGCCCAGCC CTGCCCAGTC CAGCCCAGTC CAGCCCAGCC

251 CTGCCCTTCC CAGCCCTGCC CAGCCCAGCT CATCCCTGCC CTACCCAGCC

301 CAGCCCTGTC CTGCCCTGCC CAGCCCAGCC CAGCCCAGCC CTGCCCTGCC

351 CTGCCCTGCC CTTCCCAGCC CTGACCTTCC CAGCCCTGCC CAGCCCAGCT

401 CATCCCTGCC CTACCCAGCT CAGCCCTGCC CTGCCCTGCC CTGCCCTGCC

451 CAGCCCTACC CAGCCCAGCC CTGCCCTGCC CTGCCCAGCT CAGCCCTGCC

501 CACCCCAGCC CAGCCCAGCC CAGCATGCGT TCTCTGGATG GTGAGCACAG

551 GCTTGACCTT AGAAAGAGGC TGGCAACGAG GGCTGAGGCC ACCAGGCCAC

601 TGGGTGCTCA CGGGTCAGAC AAGCCCAGAG CCTGCTCCCC TGCCACGGGT

651 CGGGGCTGTC ACCGCCAGCA TGCTGTGGAT GTGCATGGCC TCAGGGCTGC

701 TGGCTCCAGG CTGCCCCCGC CCTGGCTCCC GAGGCCACCC CTCTTATGCC

751 ATGAACCCTG TGCCACACCC ACCTCTGAGC TGTCCCCGCT CCTGCCGCCT

801 GCACCCCCTG AGCAGCCCCC TGTGTGTTTC ATGGGAGTCT TAGCAAGGAA

851 GGGGAGCTCG AATTCCTGCA GCCCGGG

FIG. 6

1   CCGGGTACCG AGCTCCCAGG AAGATAAATG ATTTCCTCCT CTCTAGAGAT

51  GGGGGTGGGA TCTGAGCACT CAGAGCCAAG GGCGCAGTGG GTCCGGGCGG

101 GGGCCCTCCT CGGCCCTCCC AACATGGGGG CCAGGAGGTC AGCCCCTCAA

151 CCTGGACCCC GGCTGGGTCT CAGGGAATGG TCTCCCCCAG TGGCCCAGCT

201 TGCTTGTGTT TTCAGATGGG TGTGCATGGG TGTGTGTGTG TGTGTGTGTG

251 TGTGTGTGTG TGTGTGTGTG TGTGATGCCT GACAAGCCCC AGAGAGCCAA

301 AGACCTGAGT GGAgATCTTG TGACTTCTCA AAAGGGGGAT TGGAAGGTTC

351 GAGAAAGAGC TGTGGTCAGC CTTGCTCTCC CTTAAGGCTG TGGTAACCAC

401 ACTAGGCATA GCATAGGCCT GCGCCCCGTC CCTCCTTCCC TCCTCCGCGC

451 CTCTCCTTTC TCTTTCTCCC CCCTCTACCC CGCTCCCTGG CCTGCTCCTG

501 GTGACACCGT TGGCCCCCTT CCAGGGCTGA GGGAAGCCAG CGGGGGCCCC

551 TTCCTGAAAG CCCACCTGCA GGCCGGCTTG CTGGGAAGGG GCTGCTCTCG

601 CAgAGGCTCC CGCCCGCCCT GCAGCCGTTT CCTGgAAGCA GTCGCTGTGG

651 GTATTCTGTT CCTTGTCAGC ACTGTGCTTG CAAAgAAAGC AgACACTGTG

701 CTCCTTGTCC TTAGGGAGCC CCGCTCCATC ACCCAACACC TGGCTGGACA

751 CAGGCGGGAG GCCGGGTCCG CGGGGAgCGG CGCGGGGCTG GGCCGGACC

801 ATTAAACACA CACGGGCGCC AGGCACTGCA GGCTCCTCCT CCTCCTCCTG

851 CCCAGCGCCT CTGCTCACAG GCACGTGCCA AgCCCCTAGG CCAggAgGCC

901 AgCAgTGGGT GCAgAACAAG CTCCTGGGAA GGGGGTGCAg GGcGGACCCC

951 CGGGGAgAAG GGCTGGCAGG GCTGTGGGGG ACGCTGACCG TGGGCCCCAC

FIG. 7A

1001 GTTGCAgAAA ACTGGNTGCC TGgCTGGAAG ATGGGGGAGA TGCCAAGCCT

1051 CTGAGGCAGC ACGAgCAGGG TGCATGGAGG CCGGGGCGCG GGGAGGCTGC

1101 ACTGCAGCAT GCACCCCAAA GCCCANAGGG AGTGGAgACC AGGCCCTGGA

1151 ATCgAGAAGT AgAAAGGCGG CTTGGAGGCC TCGGAACCGG CTGACCTCCA

1201 ACAGAgTGGG TCTCCAGCCT GgcTCTGCCC TGCCGCAGGT CCCCTCCCcT

1251 CATTACCAGG CCTAGAGCCT CCAGTCCCGG TGGCCCCCAG CCcGAGGGTG

1301 AACGGCCTCA CCCTGGGTcG TGGGACAGAG GGCACGTTCA TCAAGAGTGG

1351 CTCCCAAGGG ACAcGTGGCT GTTTGCAGTT CACAGGAAGC ATTcGAGATA

1401 AGGAGcTTGT TTTCCCAGTG GGCAcGGAGC CAGCAGGGGG GCTGTGGGGC

1451 AGCCCAGGGT GCAAGGcCAG GcTGTGGGGC TGCAGcTGCc TTGGGCCCCA

1501 CTCCCAGGCC TTTGCGGGAG GTGGGAGGCG gGAGGCGGCA GCTGCACAGT

1551 GGCCCCAGGC GAGGCTCTCA GCCCCAGTCG CTCTCCGGGT GGGCAGCCCA

1601 AGAGGGTCTG GCTGAGCCTC CCACATCTGG GACTCCATCA CCCAACAACT

1651 TAATTAAGGC TGAATTTCAC GTGTCCTGTG ACTTGGGTAG ACAAAGCCCC

1701 TGTCCAAAGG GGCAGCCAGC CTAAGGCAGT GGGGACGGCG TGGGTGGCGG

1751 GCGACGGGGG AGATGGACAA CAGGACCGAG GGTGTGCGGG CGATGGGGGA

1801 GATGGACAAC AGGACCGAGG GTGTGCGGGC GATGGGGGAG ATGGACAACA

1851 GGACCGAGGG TGTGCGGGAC ACGCATGTCA CTCATGCACG CCAATGGGGG

1901 GCGTGGGAGG CTGGGGAGCA GACAGACTGG GCTGGGCTGG GCGGGAAGGA

1951 CGGGCAGATG

FIG. 7B

```
   1 CCGGGTACCG AGCTCCCAGG AAGATAAATG ATTTCCTCCT CTCTAGAGAT
  51 GGGGGTGGGA TCTGAGCACT CAGAGCCAAG GGCGCAGTGG GTCCGGGCGG
 101 GGGCCCTCCT CGGCCCTCCC AACATGGGGG CCAGGAGGTC AGCCCCTCAA
 151 CCTGGACCCC GGCTGGGTCT CAGGGAATGG TCTCCCCCAG TGGCCCAGCT
 201 TGCTTGTGTT TTCAGATGGG TGTGCATGGG TGTGTGTGTG TGTGTGTGTG
 251 TGTGTGTGTG TGTGTGTGTG TGTGATGCCT GACAAGCCCC AGAGAGCCAA
 301 AGACCTGAGT GGAgATCTTG TGACTTCTCA AAAGGGGGAT TGGAAGGTTC
 351 GAGAAAGAGC TGTGGTCAGC CTTGCTCTCC CTTAAGGCTG TGGTAACCAC
 401 ACTAGGCATA GCATAGGCCT GCGCCCCGTC CCTCCTTCCC TCCTCCGCGC
 451 CTCTCCTTTC TCTTTCTCCC CCCTCTACCC CGCTCCCTGG CCTGCTCCTG
 501 GTGACACCGT TGGCCCCCTT CCAGGGCTGA GGGAAGCCAG CGGGGGCCCC
 551 TTCCTGAAAG CCCACCTGCA GGCCGGCTTG CTGGGAAGGG GCTGCTCTCG
 601 CAgAGGCTCC CGCCCGCCCT GCAGCCGTTT CCTGgAAGCA GTCGCTGTGG
 651 GTATTCTGTT CCTTGTCAGC ACTGTGCTTG CAAAgAAAGC AgACACTGTG
 701 CTCCTTGTCC TTAGGGAGCC CCGCTCCATC ACCCAACACC TGGCTGGACA
 751 CAGGCGGGAG GCCGGGTCCG CGGGGAgCGG CGCGGGGCTG GGGCCGGACC
 801 ATTAAACACA CACGGGCGCC AGGCACTGCA GGCTCCTCCT CCTCCTCCTG
 851 CCCAGCGCCT CTGCTCACAG GCACGTGCCA AgCCCCTAGG CCAggAgGCC
 901 AgCAgTGGGT GCAgAACAAG CTCCTGGGAA GGGGGTGCAg GGcGGACCCC
 951 CGGGGAgAAG GGCTGGCAGG GCTGTGGGGG ACGCTGACCG TGGGCCCCAC
1001 GTTGCAgAAA ACTGGNTGCC TGgCTGGAAG ATGGGGGAGA TGCCAAGCCT
1051 CTGAGGCAGC ACGAgCAGGG TGCATGGAGG CCGGGGCGCG GGGAGGCTGC
1101 ACTGCAGCAT GCACCCCAAA GCCCANAGGG AGTGGAgACC AGGCCCTGGA
1151 ATCgAGAAGT AgAAAGGCGG CTTGGAGGCC TCGGAACCGG CTGACCTCCA
1201 ACAGAgTGGG GCCGGCCCTG GAGGCAAAGA GGTGCCCGGG GTCCGGCCCT
1251 GCCTGGGGGA GCTATGTGTC ATGGGCAAGC CACAGGATAT GTagCCCGCT
1301 CTGagCCTAT GGACCCagGG CAGGGCTGCA AGGCAGGGCA GGGGAGACAG
1351 CACGGGGGAG CAAGGAGCAG AGAGGGGGCC TCAGGCTCTC CCAGGAGGAA
1401 CATTCTCCCG ACAGGAGGAA GAGACGGCCC AGGGGTGACT GTGGGGAGCC
1451 ATGGTGGCAG CTGGGGTCGT GGCAGATGGG AGAGAGGCTG GCGAGGTGAA
1501 GGTGCAGGGG TCAGGGCTCT GGGGCCCACA TGCCTGTGGG AGCAGGCAGG
```

FIG.8A

1551 CCCAGGGCTC TCCGCCACTC CCCACTCCCG CTTGGCTCAT AGGCTGGGCC

1601 CAAGGGTGGG GTGGGATGAG CAGGAGATGG GGCCCAGGGG GCAAGCAGGG

1651 CCCCAAAGAC ATTTAGAAAA ACCGGTTTAT GCAGGCAGCA TTCAGAGCAG

1701 GCGGCGTGCG TGGCGGGGGC CCTGGGAGCA CAGAGAGGCA CACGTAGGGC

1751 CCCCGAGGGG CTCCCCATTG GCCGGCAGTG ACATCACCCC TGTGTCAACA

1801 GTGATGTCTG CAGCTCCGGC CAGCCAGGGT TTATGGAGCG AGACCCAGCC

1851 CGGCCTGGGC CCTCACTCCC CAGGCCCACA CACTAGCCCA CTGTTCAGGG

1901 TCCGGGGTGG CGGCATGGCC TGGGGGTCCT GGCACCGCTG CTCCTCTGCC

1951 CACCCTAACT TCCCGGCATG GCGGCTGCCC CCTCTGAGCG TCCCCAACCA

2001 GTAAGTGTGG GGCCCAGCAG gCCTGCcGTC CTCcTCcTCT TCCCCTcTAG

2051 AGAGAAACGT GGAGGTCCTG GGGCTGGGGG CGCTCATAGC CcTGTGACAC

2101 AGGTGCATGG GGTCAGGGGT CCCAGAATGG CCCCTGGGAA GGACCTCAGC

2151 TGGGCCGGCG GCTcTAGGCT TCAGGGGTCT GTCTGCACAG GGGNTAGCCC

2201 CTCCCAGACC TCTGTGAAGC CAGTACGGGC CTCCCCTCCC TGCCCCGTGC

2251 TCTGTCCGGT GCTTCCTGGA CTGCACTGCG GGCCACTGGT GAGAGGGTGG

2301 ACAGGGAAGG GCCGCCGTGG TGCCTGTTCC TGCCCACCTG GCTGTGTGGT

2351 CCCCTCCAAG TAGGGACAAC CCTTCTGAGG GCTTGGGGGC ACCCTGGGGT

2401 TGCCAGGGCC TCCCAGAGCC CTGTGAGCCC CTGGGGGGTC TGGCCTGATG

2451 CCCCCCTCCA CGTCCAGGGC CGGCTGTGGC CCAGAACCCC AGCTTCCCAG

2501 CAGGCCGGTG TGCGGTGGTG ACCCAGGAGA GGCCTCGCCT CCACTGAGGG

2551 GCCACCGACC TCTGTCAGAC CACAGAGACC CCCAAGGAgT cTGAAGGCTG

2601 GAGACCCGGG GCTGGGACCA GGTGGGAcTT TCCCACGGAG CCGTCCCCAG

2651 GCCCAGCTGG GGACAcGTCC CCcTTcTcTC CAGACACACC CTGCcTGCCA

2701 CCAGGACACA CCGGCCTGTT GGGGGTcTcT TTTAAGTGCT TGCCACTCTG

2751 AGGTGAcTGT CCCTTTCCAA AGAGGTTTcT GGGGCCCAGG TGGGAtGCGT

2801 CGGCCTGAGC AGGAGGATcT GGGCCGCCAG GGGCTGGGGA CTGTcTCCTG

2851 GGGAAGGAAG CGCCTGGGAG CGTGTGTGCT GACCCAGGAC CATCCAGGGA

2901 GGCCCGTcTG TGGGGCAAGC GGGAAGGGAG CGGCTGGAGA GGCTTGGCCG

2951 CCCCCGCCCT GCCTCCCATT CCTTAGcTCC ATGCCTGTCA ACCTcTGTCA

FIG.8B

3001 CCCAGTGAGT GATGTCCAGG GGCCCTGGAA AGGTCACAGC ATGTTTGAGC

3051 GGGGTGAGAG AGAGGGGAAA GGCGGGGGCG GGGAAAAGTA cGTGGAGGAA

3101 GCTTTAGGCC CAAGGAAGGA GACAGGGTTc TGGGAGGGAG GGAGCCACTG

3151 GGGCCGCCGG GAAGGTCCCT GCTTGCTGCT GCCACCCAGA ACCCTCGCCT 3201 cTTAGcTAGC CCCcGCAGCC CCAGCcTTTc TGGCNTGTGg CCCTCTCCCC

3251 CATCCCCAGG TGTCcTgTGC AACCAGGCcT TGGACCCAAA CCCTCcTGCC

3301 CCCTCcTCTC CCTCCTCACC CTCCCAATGC AGTGGTCTCC AGCCTGGcTC

3351 TGCCCTGCCG CAGGTCCCCT CCCcTCATTA CCAGGCCTAG AGCCTCCAGT

3401 CCCGGTGGCC CCCAGCCcGA GGGTGAACGG CCTCACCCTG GGTcGTGGGA

3451 CAGAGGGCAC GTTCATCAAG AGTGGCTCCC AAGGGACAcG TGGCTGTTTG

3501 CAGTTCACAG GAAGCATTcG AGATAAGGAG cTTGTTTTCC CAGTGGGCAc

3551 GGAGCCAGCA GGGGGGCTGT GGGGCAGCCC AGGGTGCAAG GcCAGGcTGT

3601 GGGGCTGCAG cTGCcTTGGG CCCCACTCCC AGGCCTTTGC GGGAGGTGGG

3651 AGGCGgGAGG CGGCAGCTGC ACAGTGGCCC CAGGCGAGGC TCTCAGCCCC

3701 AGTCGCTCTC CGGGTGGGCA GCCCAAGAGG GTCTGGCTGA GCCTCCCACA

3751 TCTGGGACTC CATCACCCAA CAACTTAATT AAGGCTGAAT TTCACGTGTC

3801 CTGTGACTTG GGTAGACAAA GCCCCTGTCC AAAGGGGCAG CCAGCCTAAG

3851 GCAGTGGGGA CGGCGTGGGT GGCGGGCGAC GGGGGAGATG GACAACAGGA

3901 CCGAGGGTGT GCGGGCGATG GGGGAGATGG ACAACAGGAC CGAGGGTGTG

3951 CGGGCGATGG GGGAGATGGA CAACAGGACC GAGGGTGTGC GGGACACGCA

4001 TGTCACTCAT GCACGCCAAT GGGGGGCGTG GGAGGCTGGG GAGCAGACAG

4051 ACTGGGCTGG GCTGGGCGGG AAGGACGGGC AGATG

FIG. 8C

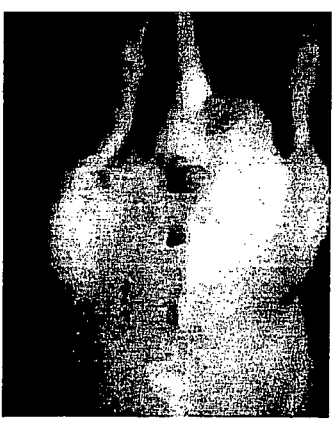
FIG. 12A
INFECTION IN VIVO
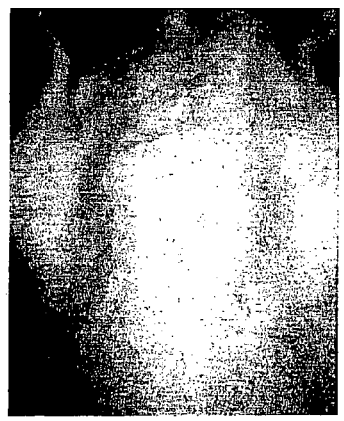
FIG. 12B
TRANSFECTION IN VIVO

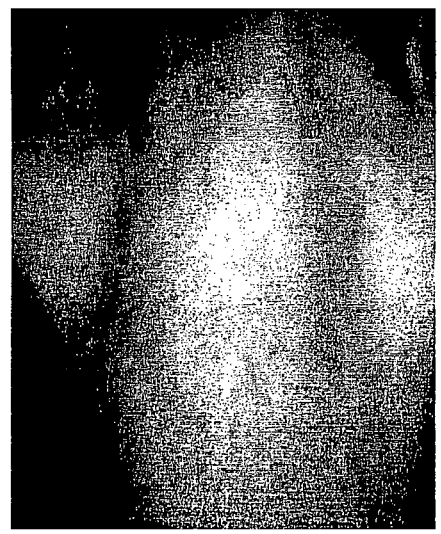
pH19 Luc transfected Bladder 52 h after inoculation
TRANSFECTION IN VIVO
FIG. 12C

METHODS AND COMPOSITIONS FOR INDUCING TUMOR-SPECIFIC CYTOTOXICITY

The present application is a continuation-in-part of U.S. application Ser. No. 09/568,059 filed May 10, 2000, now U.S. Pat. No. 6,306,833, which is a divisional of application Ser. No. 09/165,240 filed Oct. 1, 1998, now U.S. Pat. No. 6,087,164, issued Jul. 11, 2000, which is a continuation-in-part of application Ser. No. 08/943,608, filed Oct. 3, 1997, now abandoned. Each application is incorporated by reference herein in its entirety.

1. FIELD OF THE INVENTION

The present invention is in the field of tumor cell biology, in particular cancer treatment, and relates to the specific expression of heterologous polynucleotides in tumor cells. More specifically, the invention relates to methods for treating or preventing cancer comprising administering a polynucleotide encoding a cytotoxic product operably linked to a transcriptional regulatory sequence.

2. BACKGROUND OF THE INVENTION

2.1 The H19 Gene

The H19 gene is one of several genes known to be imprinted in humans (Hurst et al., 1996, Nature Genetics 12:234–237). At the very beginning of embryogenesis, H19 is expressed from both chromosomal alleles (DeGroot et al., 1994, Trophoblast 8:285–302). Shortly afterwards, silencing of the paternal allele occurs, and only the maternally inherited allele is transcribed.

H19 is abundantly expressed during embryogenesis, and was first identified as a gene that was coordinately regulated with alpha-fetoprotein in liver by the trans-acting locus raf (Pachnis et al., 1984, "Locus unlinked to alpha-fetoprotein under the control of the murine raf and Rif genes", Proc Natl Acad Sci. 81:5523–5527). Additionally, H19 has been independently cloned by several groups using screens aimed at isolating genes expressed during tissue differentiation. For example, the mouse homolog of H19 was identified in a screen for genes that are active early during differentiation of C3H10T1/2 cells (Davis et al., 1987, "Expression of a single transfected cDNA converts fibroblasts to myoblasts", Cell 51:987–1000). Similarly, murine H19 was shown to be expressed during stem cell differentiation and at the time of implantation (Poirier et al., 1991, "The murine H19 gene is activated during embryonic stem cell differentiation in vitro and at the time of implantation in the developing embryo", Development 113:1105–1114). Transcription of the human H19 gene was also discovered in differentiating cytotrophoblasts from human placenta (Rachmilewitz et al., 1992, Molec. Reprod. Dev. 32:196–202).

While transcription of H19 RNA occurs in many different embryonic tissues throughout fetal life and placental development, H19 expression is downregulated postnatally, although low levels of H19 transcription have been reported, for example, in murine adult muscle and liver (Brunkow and Tilghman, 1991, "Ectopic expression of the H19 gene in mice causes prenatal lethality", Genes Dev. 5:1092–1101).

Interestingly, H19 transcription can be re-activated postnatally in cancer cells as demonstrated in tumors derived from tissues expressing H19 prenatally (Ariel et al., 1997, "The product of the imprinted H19 gene is an oncofetal RNA", Mol Pathol. 50:34–44). Additionally, H19 RNA is postnatally expressed in some tumors, in particular astrocytoma and ganglioneuroblastoma, which are derived from neural tissues not known to express H19 (Ariel et al. supra). Given that H19 RNA is expressed in many types of tumors and cancers, Ariel et al. speculated that H19 RNA was an oncofetal RNA, and proposed investigating H19 as a tumor marker for human neoplasia.

Both human and murine H19 genes have been cloned and sequenced (Brannan et al., 1990, "The product of the H19 gene may function as an RNA", Mol Cell Biol. 10:28–36). Comparison of the human and murine H19 genes revealed an overall 77% nucleotide sequence identity. Despite this conservation of nucleotide homology between the species, very low deduced amino acid sequence identity could be predicted from the open reading frames of the two genes (Brannan et al. supra). Further, although H19 RNA was transcribed, spliced, and polyadenylated, the RNA did not appear to be translated. Instead, H19 RNA was found to associate with the 28S cytoplasmic RNA, leading to speculation that H19 RNA may function as an RNA component of a ribonucleoprotein (Brannan et al. supra).

H19 can act as a dominant lethal gene. For example, high ectopic expression of an H19 transgene causes lethality in mice shortly before birth (Brunkow and Tilghman, 1991, "Ectopic expression of the H19 gene in mice causes prenatal lethality", Genes Dev. 5:1092–1101). This lethal period coincides with the developmental period when H19 transcription normally becomes repressed.

Disruption of H19 expression (e.g., by knockout) does not appear to produce physical defects, as demonstrated by mice that are heterozygous or homozygous for an H19 knockout allele, however (Leighton et al., 1995, "Disruption of imprinting caused by deletion of the H19 gene region in mice", Nature 375:34–39). A knockout of the maternally inherited H19 allele does interfere with imprinting of the genetically linked, and oppositely imprinted, insulin-like growth factor 2 ("IGF-2") gene. In such knockouts, the resulting mice are larger at birth than their wild-type littermates probably due to increased prenatal expression of IGF-2 (Leighton et al. supra). Since these two oppositely imprinted genes share cis-acting regulatory sequences, Leighton et al. speculated that H19 may be involved in imprinting the IGF-2 gene.

The H19 gene product may act as a tumor suppressor RNA. For example, transfection of two embryonal tumor cell lines (RD and G401) with an H19 expression construct resulted in cell growth retardation, morphological changes, and reduced tumorigenicity in nude mice (Hao et al., 1993, "Tumour-suppressor activity of H19 RNA", Nature 365: 764–767). Such tumor suppressor activity has been noted as consistent with the observed lethality of ectopic expression in mice (Hao et al., supra) as well as the increased size of mice in which the maternal H19 allele is knocked out (Leighton et al., supra).

The proposal that H19 is a tumor suppressor has been controversial, however. Some of the published results were reportedly not reproduced, and other candidate tumor suppressor genes closely linked to H19 may exist (Ariel et al., supra). Moreover, the proposed role of H19 as a tumor suppressor runs counter to the fact that H19 is activated in many different types of tumor cells (See, e.g., Lustig-Yariv et al., 1997, "The expression of the imprinted genes H19 and IGF-2 in choriocarcinoma cell lines. Is H19 a tumor suppressor gene?", Oncogene 15:169–177).

2.2 The Insulin-Like Growth Factor Genes

IGF-2 is another imprinted gene whose expression depends upon its parental origin. However in contrast to H19, IGF-2 is maternally imprinted in both mice and humans, and is therefore expressed from the paternally inherited allele (Rainier et al., 1993, "Relaxation of imprinted genes in human cancer", Nature 362:747–749). The human IGF-2 gene exhibits a complex transcriptional pattern. There are four IGF-2 promoters that are activated in a tissue-specific and developmentally specific manner. Only three of the IGF-2 promoters (i.e., P2, P3 and P4) are imprinted and active during fetal development and in cancer tissues. The P3 promoter of the IGF-2 gene has been implicated in the progression of liver cirrhosis and hepatocellular carcinoma (Seo et al., 1998, "Different protein-binding patterns in the P3 promoter region of the human insulin-like growth factor II gene in the human liver cirrhosis and hepatocellular carcinoma tissues", J Korean Med Sci.13:171–178).

The fourth IGF-2 promoter, (i.e., P1) is not imprinted, and is activated only in the adult liver and choroid plexus (See Holthuizen et al., 1993, "Transcriptional regulation of the major promoters of the human IGF-II gene", Mol Reprod Dev. 35:391–393).

Loss of imprinting of IGF-2 has been implicated in Wilm's tumor (Ogawa et al., 1993, "Relaxation of insulin-like growth factor II gene imprinting implicated in Wilms' tumour", Nature 362:749–751). This observation led many investigators to speculate that the loss of imprinting and biallelic expression of imprinted genes may be involved in growth disorders and the development of cancer (See, e.g., Rainier et al., 1993, Nature 362:747–749; Glassman et al., 1996, "Relaxation of imprinting in carcinogenesis", Cancer Genet Cytogenet. 89:69–73).

2.3 Tumor-Specific Gene Therapy

Regulatory sequences from tumor-associated genes have been used to selectively target expression of a suicide gene in tumor-derived cells. For example, alpha-fetoprotein expression has been induced in hepatocellular carcinoma by using control (i.e., regulatory) sequences from the albumin gene or the alpha-fetoprotein gene to target expression in hepatoma cells of coding sequences from the varicella-zoster virus thymidine kinase ("VZV TK") gene (Huber et al., 1991, "Retroviral-mediated gene therapy for the treatment of hepatocellular carcinoma: an innovative approach for cancer therapy", Proc Natl Acad Sci. 88:8039–8043). Hepatoma cells that were infected in vitro with a retroviral vector containing one of these VZV TK expression constructs became sensitive to the normally non-toxic prodrug 6-methoxypurine arabinonucleoside ("araM").

An adenoviral vector engineered to express Herpes simplex virus thymidine kinase ("HSV TK") under the control of alpha-fetoprotein regulatory sequences was directly injected into hepatocellular carcinoma-derived tumors, generated in athymic nude mice, and subsequent intraperitoneal injections with ganciclovir demonstrated regression of the tumors (Kaneko et al., 1995, "Adenovirus-mediated gene therapy of hepatocellular carcinoma using cancer-specific gene expression", Cancer Res. 55:5283–5287).

Ganciclovir sensitivity of A549 lung carcinoma cells that were transfected with an expression construct containing regulatory sequences of the lung carcinoembryonic antigen ("CEA") gene operatively linked to the coding sequence of the HSV TK gene has also been demonstrated (Osaki et al., 1994, "Gene therapy for carcinoembryonic antigen-producing human lung cancer cells by cell type-specific expression of herpes simplex virus thymidine kinase gene", Cancer Res. 54:5258–5261). In addition, repeated intraperitoneal injections of ganciclovir inhibited tumor growth in nude mice that were subcutaneously injected with transfected cells. However, the CEA gene is expressed in normal colonic mucosa, thus limiting the usefulness of CEA transcriptional regulatory sequences as tumor-specific regulatory regions (Osaka et al., 1994, supra).

Thus, there remains a need for the development of gene therapy vectors that express gene products specifically in target cells, particularly in tumor cells.

3. SUMMARY OF THE INVENTION

The invention relates to methods and compositions for inducing selective expression of heterologous polynucleotides in target cells, particularly tumor cells. Such methods and compositions are useful for the treatment of a wide variety of disorders, particularly cancer.

In particular, the present invention relates to a vector comprising a heterologous polynucleotide operatively linked to one or more transcriptional regulatory sequences, which results in cancer-specific expression of the heterologous polynucleotide. More particularly, the transcriptional regulatory sequence is derived from a H19 enhancer, IGF-2 P3 promoter, IGF-2 P4 promoter or IGF-1 promoter and the heterologous polynucleotide encodes a cytotoxic or cytostatic product.

In one embodiment, the transcriptional regulatory sequence directs selective expression of the heterologous polynucleotide in target cells to prevent or treat a disease or disorder, such as cancer.

In a preferred embodiment, the vector comprises one or more transcriptional regulatory sequences operatively linked to a heterologous polynucleotide that results in tumor-specific expression of the heterologous polynucleotide. The transcriptional regulatory sequence can be derived from a genomically imprinted gene, which transcriptional regulatory sequence is more active, or is specifically active, in tumor cells, as compared with non-tumor cells. Preferably, the transcriptional regulatory sequence is H19 promoter or H19 enhancer, or variant thereof. Alternatively, the transcriptional regulatory sequence can be an IGF-2 P3 promoter, IGF-2 P4 promoter, IGF-1 promoter, or a variant thereof.

Transcriptional regulatory sequences can direct gene expression in several different cancerous cell types. Moreover, expression of the heterologous polynucleotide can damage, inhibit the growth of, or kill the host cancer cell by producing a cytotoxic or cytostatic product. Alternatively, if the vector is a replicative virus, and expression of the polynucleotide results in an gene product that permits viral replication, the therapeutic effect can be achieved by the lytic effect of the replicating virus on the host cancer cell.

In a preferred embodiment, a transcriptional regulatory sequence comprises an H19 transcriptional regulatory sequence (e.g., H19 promoter, H19 enhancer sequence), and variants thereof.

In another preferred embodiment, a transcriptional regulatory sequence comprises a promoter region of IGF-2 P3, IGF-2 P4 or IGF-1, or a variant thereof. In a specific embodiment, an IGF-1 promoter, or variant thereof, is operatively linked to a heterologous polynucleotide to result in tumor-specific expression of the heterologous polynucleotide.

In a further embodiment, the transcriptional regulatory sequence comprises an enhancer region, or a variant thereof. Enhancers are preferably derived from the same genes as the promoter. In one embodiment, the transcriptional regulatory sequence comprises an enhancer region of the H19 gene, IGF-1 gene or IGF-2 gene, or a variant thereof. In a specific embodiment, an H19 enhancer, or variant thereof, can be used in any combination with a transcriptional regulatory sequence comprising an H19 promoter, IGF-2 P3 promoter, IGF-2 P4 promoter or IGF-1 promoter.

In one aspect of the invention, expression vectors comprising transcriptional regulatory sequences, that are operatively linked to heterologous polynucleotides ("vectors of the invention"), are used to deliver the heterologous polynucleotide into target cells.

The present invention also relates to host cells having one or more of such vectors.

The present invention also provides for methods of using such vectors to express heterologous polynucleotides in tumor cells. In a specific embodiment, a first expression construct containing a heterologous polynucleotide controlled by an H19 promoter, with or without an H19 enhancer, can be co-introduced into a cell with a second expression construct containing the same or different heterologous polynucleotide controlled by an IGF-1 promoter, IGF-2 P3 promoter, or IGF-2 P4 promoter, optionally in combination with an H19 enhancer.

The present invention also relates to a vector of the invention that is administered by gene therapy to prevent or treat a proliferative disorder, particularly cancer.

In one embodiment, the present invention provides a method for treating or preventing cancer, comprising administering to a subject in need thereof an effective amount of a vector comprising a heterologous polynucleotide operably linked to one or more transcriptional regulatory sequences, wherein the regulatory sequence is preferably derived from an H19, IGF-1 or IGF-2 transcriptional regulatory sequence. In a particular further embodiment, the regulatory sequence is preferably derived from an H19, IGF-1, IGF-2 P3 or IGF-2 P4 promoter sequence.

In a specific embodiment, the vector is administered by direct injection into the tumor or cancerous tissue. In another specific embodiment, the vector is administered by systemic administration (e.g., intravenous infusion). In yet another specific embodiment, the vector is administered into the lumen of a tissue or organ (e.g., intravesically). In a further specific embodiment, the vector comprises a heterologous polynucleotide that encodes a cytostatic product. In yet a further specific embodiment, the vector comprises a heterologous polynucleotide that encodes a cytotoxic product.

In another embodiment, the present invention provides a method of reducing cell growth comprising the step of contacting a cell with an effective amount of a vector comprising a heterologous polynucleotide operably linked to one or more regulatory sequences, wherein the regulatory sequence is preferably derived from an H19, IGF-1 or IGF-2 transcriptional regulatory sequence. In a particular further embodiment, the regulatory sequence is preferably derived from an H19, IGF-1, IGF-2 P3 or IGF-2 P4 promoter sequence. In a further embodiment, the regulatory sequence comprises an enhancer sequence that is more active, or specifically expressed, in cancer cells. In a further specific embodiment, the vector comprises a heterologous polynucleotide that encodes a cytostatic product. In yet a further specific embodiment, the vector comprises a heterologous polynucleotide that encodes a cytotoxic product. In a specific embodiment, the cell is a cancer cell.

In another embodiment, the present invention provides a method for treating or preventing cancer, comprising administering to a subject in need thereof an effective amount of a replicative virus, wherein the replicative virus comprises a polynucleotide (the expression of which permits viral replication) operably linked to one or more regulatory sequences, and wherein the regulatory sequence is preferably derived from an H19, IGF-1 or IGF-2 transcriptional regulatory sequence. In a particular further embodiment, the regulatory sequence is preferably derived from an H19, IGF-1, IGF-2 P3 or IGF-2 P4 promoter sequence. In a particular embodiment, expression of the polynucleotide comprises a sequence encoding a product important for viral replication. In another particular embodiment, expression of the polynucleotide comprises a sequence encoding a product essential for viral replication. In yet another particular embodiment, the polynucleotide is a heterologous polynucleotide.

In a specific embodiment, the replicative virus is administered by direct injection into the tumor or cancerous tissue. In another specific embodiment, the replicative virus is administered by systemic administration (e.g., intravenous infusion). In yet another specific embodiment, the replicative virus is administered into the lumen of a tissue or organ (e.g., intravesically).

In a further embodiment, said replicative virus is administered in combination with an effective amount of a heterologous polynucleotide operably linked to one or more transcriptional regulatory sequences, wherein the heterologous polynucleotide encodes a cytotoxic or cytostatic product.

In another embodiment, the present invention provides a method of reducing cell growth comprising the step of contacting a cell with an effective amount of a replicative virus, wherein the replicative virus comprises a polynucleotide (the expression of which permits viral replication) operably linked to one or more regulatory sequences, and wherein the regulatory sequence is more active, or specifically expressed, in cancer cells. In a particular embodiment, the regulatory sequence is derived from an H19, IGF-1 or IGF-2 transcriptional regulatory sequence. In a particular further embodiment, the regulatory sequence is preferably derived from an H19, IGF-1, IGF-2 P3 or IGF-2 P4 promoter sequence. In another particular further embodiment, the transcriptional regulatory sequence comprises an enhancer sequence that is more active, or specifically expressed, in cancer cells. In a particular embodiment, expression of the polynucleotide comprises a sequence encoding a product important for viral replication. In another particular embodiment, expression of the polynucleotide comprises a sequence encoding a product essential for viral replication. In yet another particular embodiment, the polynucleotide is a heterologous polynucleotide.

The present invention also relates to a method for treating or preventing cancer, comprising administering to a subject in need thereof an effective amount of a vector comprising a heterologous polynucleotide operably linked to one or more transcriptional regulatory sequences, wherein the transcriptional regulatory sequence is preferably derived from an H19, IGF-1, IGF-2 P3 or IGF-2 P4 promoter sequence; and one or more therapeutic agents. The therapeutics agent(s) can be delivered before, after or concurrently with a vector of the invention.

The present invention also relates to a method for treating or preventing cancer, comprising administering to a subject in need thereof an effective amount of a replicative virus, wherein the replicative virus comprises a polynucleotide operably linked to one or more regulatory sequences, and wherein the regulatory sequence is derived from an H19, IGF-1 or IGF-2 transcriptional regulatory sequence. In a particular further embodiment, the regulatory sequence is preferably derived from an H19, IGF-1, IGF-2 P3 or IGF-2 P4 promoter sequence. In another particular further embodiment, the transcriptional regulatory sequence comprises an enhancer sequence that is more active, or specifically expressed, in cancer cells. In a particular embodiment, expression of the polynucleotide comprises a sequence encoding a product important for viral replication. In another particular embodiment, expression of the polynucleotide comprises a sequence encoding a product essential for viral replication. In yet another particular embodiment, the polynucleotide is a heterologous polynucleotide. The therapeutics agent(s) can be delivered before, after or concurrently with a vector of the invention.

In a further embodiment, the replicative virus is administered in combination with an effective amount of a vector comprising a heterologous polynucleotide operably linked to one or more transcriptional regulatory sequences, wherein the transcriptional regulatory sequence comprises an enhancer sequence that is more active, or specifically expressed, in cancer cells, and wherein the heterologous polynucleotide encodes a cytotoxic or cytostatic product.

The additional therapeutic agent(s) can be co-administered or, alternatively, administered at different intervals in a manner consistent with typical administration of the therapeutic agent.

The present invention also relates to a method for increasing a subject's sensitivity to a therapeutic agent, comprising administering to a subject in need thereof an effective amount of: (a) a vector comprising a heterologous polynucleotide operably linked to one or more regulatory sequences, wherein the regulatory sequence is preferably derived from an H19, IGF-1 or IGF-2 transcriptional regulatory sequence; and another therapeutic agent; or (b) a replicative virus, wherein the replicative virus comprises a polynucleotide operably linked to one or more regulatory sequences, and wherein the regulatory sequence is preferably derived from an H19, IGF-1 or IGF-2 transcriptional regulatory sequence.

In one embodiment, the heterologous polynucleotide comprises a sequence encoding a cytotoxic or cytostatic product (e.g., thymidine kinase, diphtheria toxin, Pseudomonas toxin, ricin, cholera toxin, retinoblastoma gene, p53).

In another embodiment, the heterologous polynucleotide comprises a sequence encoding a gene product that permits viral replication. In a preferred embodiment, the heterologous polynucleotide comprises a sequence encoding a product essential for viral replication. In another preferred embodiment, the replicative virus is an adenovirus.

In a preferred embodiment, the transcriptional regulatory sequence comprises an H19 promoter, an H19 enhancer, or both an H19 promoter and enhancer. In another preferred embodiment, the H19 enhancer is placed 3' to the heterologous polynucleotide.

3.1 Definitions

As used herein, the phrase "operatively linked" means that a polynucleotide is linked to a regulatory sequence in a manner which allows expression of the polynucleotide to be directed by the regulatory sequence.

As used herein, the phrase "heterologous polynucleotide" refers to a sequence or a plurality of sequences that is/are not normally operatively linked to the regulatory sequences of the invention. The heterologous polynucleotide can comprise any nucleotide sequence useful for disrupting, damaging, or killing tumor or cancer cells. In one embodiment, a heterologous polynucleotide comprises a sequence encoding a cytostatic or cytotoxic product. In another specific embodiment, a polynucleotide comprises a sequence encoding a product required for viral replication, i.e., a product without which the virus cannot normally replicate. For example, the product can be the E1a gene product where the virus is an adenovirus.

As used herein, the term "expression" refers to the transcription of the DNA of interest, and optionally, the splicing, processing, stability, and/or translation of the corresponding mRNA transcript. Depending on the structure of the DNA molecule delivered, expression may be transient, continuous, inducible, or constitutive.

As used herein, the term "vector" refers to a construct, comprising a regulatory sequence operatively linked to a heterologous polynucleotide, that is administered to target cells. The vector can be a viral expression vector, a plasmid or a construct of naked DNA, and, optionally, can include additional sequences required for construction, selection, stability, penetration, etc.

As used herein, the term "variant" refers to a pharmaceutically acceptable salt, homologue, analogue, or fragment of a nucleotide sequence useful for the invention (e.g., vector sequences, transcriptional regulatory sequences, cloned polynucleotides of interest, etc.). Encompassed within the term "variant" are chemically modified natural and synthetic nucleotide molecules. Also encompassed within the term "variant" are conservative substitutions within the nucleotide sequence of the molecule. In addition, non-conservative substitutions within the nucleotide sequence of the molecule are encompassed within the term "variant" as used herein.

As used herein, the term "subject" is an animal, such as, but not limited to, a cow, monkey, horse, sheep, pig, chicken, turkey, quail, cat, dog, mouse, rat, rabbit, and guinea pig, and is more preferably a mammal, and most preferably a human. A subject can be a human patient.

As used herein, the phrase "therapeutic agent" refers to any molecule, compound, or treatment that assists in the treatment of a disease, especially a cell-proliferative disorder. As such, a therapeutic agent includes, but is not limited to, radiation therapy, chemotherapy, dietary therapy, physical therapy, and psychological therapy.

As used herein, the phrases "treating cancer" and "treatment of cancer" mean to inhibit the replication of cancer cells, inhibit the spread (formation of metastases) of cancer, decrease tumor size, lessen or reduce the number of cancerous cells in the body, prevent recurrence of cancer after surgical removal or other anti-cancer therapies, or ameliorate or alleviate the symptoms of the disease caused by the cancer. The treatment is considered therapeutic if there is a decrease in mortality and/or morbidity, or a decrease in disease burden manifest by reduced numbers of malignant cells in the body.

As used herein, the phrases "preventing cancer" and "prevention of cancer" mean to prevent the occurrence or recurrence of the disease state of cancer. As such, a treatment that impedes, inhibits, or interferes with metastasis, tumor growth, or cancer proliferation has preventive activity.

As used herein, the phrase "regulatory sequence derived from an H19, IGF-1 or IGF-2 transcriptional regulatory sequence" refers to a sequence "derived" (see below) from a region of the gene that regulates and/or controls the expression of the H19, IGF-1 or IGF-2 coding sequences. As such, a regulatory sequence includes, without limitation, a sequence derived from a promoter or enhancer of the H19, IGF-1 or IGF-2 genes.

The term "derived" refers to the fact that a transcriptional regulatory sequence (for example, a promoter or enhancer) can be the complete native regulatory sequence of the gene, a portion of the native regulatory sequence, a chimeric construction of the native regulatory sequence, a combinatorial construction of one or more native regulatory sequences, or a variant of the native regulatory sequence obtained by, for example, deletion, addition or replacement of at least one nucleotide. A variant regulatory sequence can comprise modified nucleotides. The derived sequence preferably demonstrates properties of control/regulation (e.g., increase/decrease) of the expression of coding sequences operably linked thereto.

4. BRIEF DESCRIPTION OF THE FIGURES

FIGS. 1A–1C. The nucleotide sequence of human H19 promoter region. The promoter region from nucleotide position −837 to −7 (relative to the start of transcription) is shown (SEQ ID NO:1).

FIG. 2. Schematic diagram of vectors used to express a heterologous polynucleotide under the control of H19 transcriptional regulatory sequences.

FIGS. 3A–3E. H19 Transcriptional Regulatory Sequences Direct Expression Of A Heterologous Gene in Bladder Cancer Cell Lines. For the five different indicated cell lines, CAT-specific activity (cpm/μg protein) is plotted as a function of the vector used for transfection. FIG. 3A: HT-1376 cells. FIG. 3B: EJ28 cells. FIG. 3C: T24P cells. FIG. 3D: 1197 cells. FIG. 3E: UM-UC-3 cells. The following vectors are described more fully below in Section 6: (1) pCAT-basic; (2) pCAT-control; (3) pH19E; (4) pH19EH19D; and (5) pH19EH19R.

FIGS. 4A–4E. The IGF-2 P3 and IGF-2 P4 Promoters Direct Expression Of A Heterologous Gene In Bladder Cancer Cell Lines. For the five different cell lines shown, luciferase-specific activity (counts per g of protein) is plotted as a function of the IGF-2 promoter used in the transfected construct to direct expression of luciferase. FIG. 4A: T24P cells. FIG. 4B: 1376 cells. FIG. 4C: UM-UC3 cells. FIG. 4D: 1197 cells. FIG. 4E: EJ28 cells. The vectors are described more fully below in Section 10.

FIG. 5: Nucleotide sequence of a human H19 promoter fragment (SEQ ID NO:2).

FIG. 6: Nucleotide sequence of a 0.9-kb H19 enhancer fragment (SEQ ID NO:3).

FIGS. 7A and 7B: Nucleotide sequence of a 2-kb H19 enhancer fragment (SEQ ID NO:4).

FIGS. 8A–8C: Nucleotide sequence of a 4-kb H19 enhancer fragment (SEQ ID NO:5).

Figures 9A, 9B, 9C:
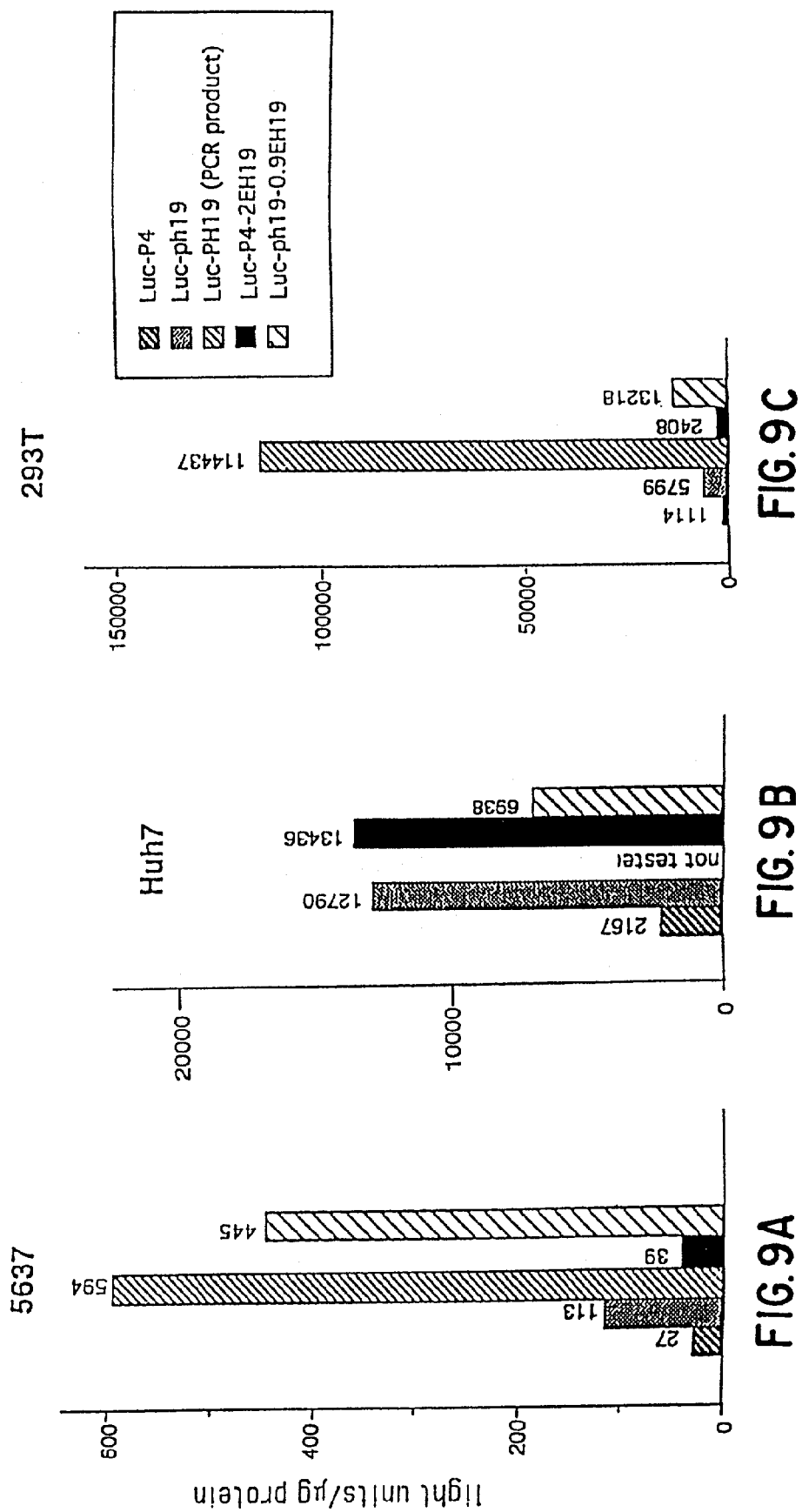

FIGS. 9A–9C: Transfection of tumor cells with vectors containing various combinations of a H19 regulatory sequence and IGF-2 P4 promoter directs luciferase expression in the tumor cells. FIG. 9A: 5637 cells. FIG. 9B: Huh7 cells. FIG. 9C: 293T cells.

Figure 10A:
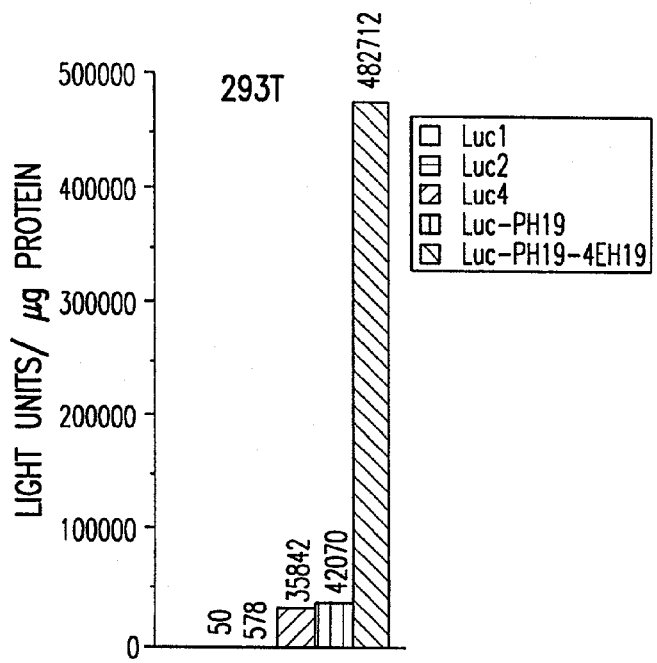
Figure 10B:
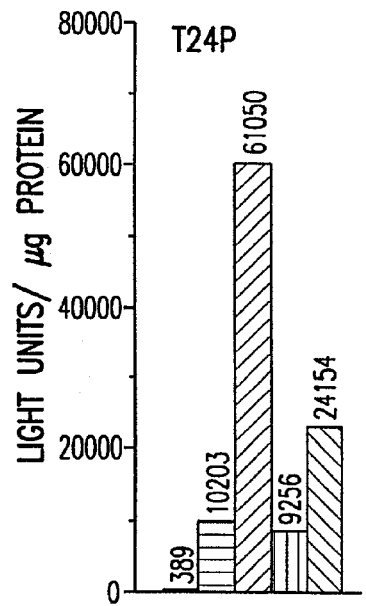
Figure 10C:
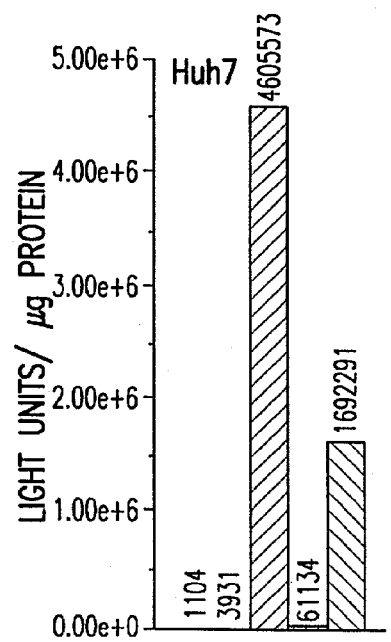
Figure 10D:
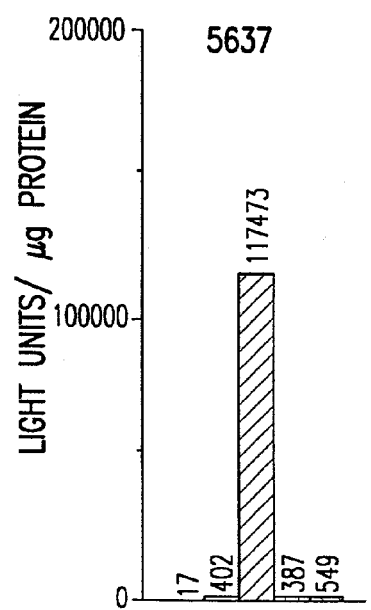
Figure 10E:
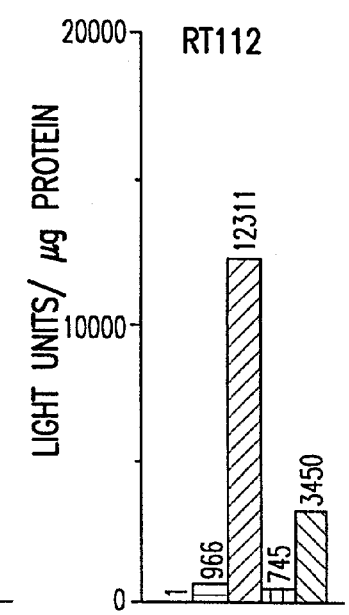

FIGS. 10A–10E: Transfection with vectors containing H19 transcriptional regulatory regions direct luciferase expression in tumor cells. FIG. 10A: 293T cells. FIG. 10B: T24P cells. FIG. 10C: Huh7 cells. FIG. 10D: 5637 cells. FIG. 10E: RT112 cells.

Figure 11:
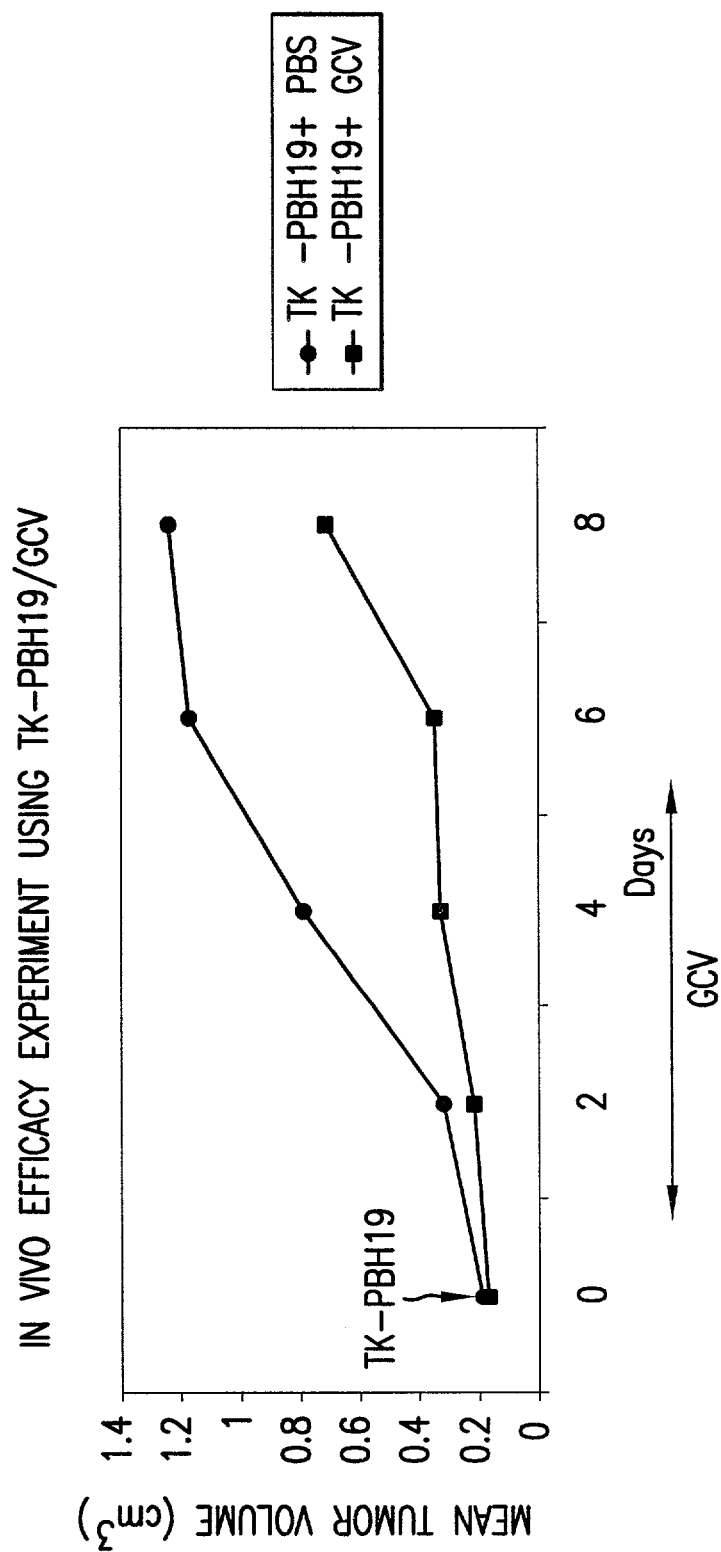

FIG. 11: shows the mean tumor size, as a function of time, of animals administered with Tk-PBH19 plasmid in the presence of PBS (circles) or GVC (squares).

FIGS. 12A–12C: shows fluorescence emission from bladder of a rat (center: bladder only; right: abdomen). FIG. 12A shows bladder intravesically administered with SV40-Luc vector. FIG. 12B shows bladder intravesically administered with pH19-Luc vector. FIG. 12C shows the bladder of FIG. 12B approximately 52 hours after inoculation.

Figure 13:
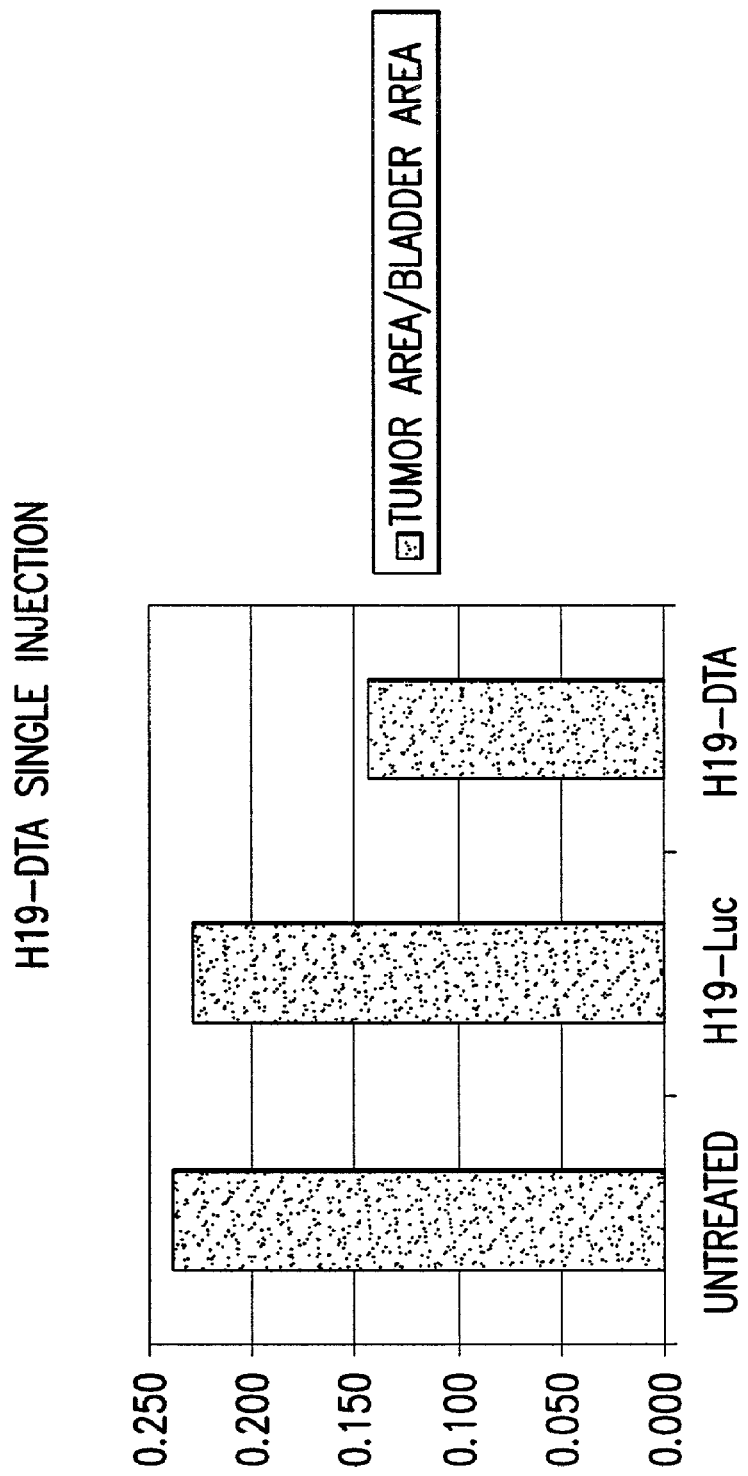

FIG. 13: shows the ratio of tumor surface area to total bladder surface area in BBN-induced untreated animals ("Untreated"), in animal treated with a construct comprising a control, non-cytotoxic gene under the control of an H19 promoter ("H19-Luc") and a construct comprising a cytotoxic gene (diphtheria toxin) under the control of an H19 promoter ("H19-DTA").

5. DETAILED DESCRIPTION OF THE INVENTION

The present invention is based, in part, on the discovery that regulatory regions can be used to target the expression of coding sequences of interest in cancer cells. For example, several genomically imprinted genes are highly expressed in cancer cells, but generally not in non-cancerous tissues. Accordingly, a vector of the invention can comprise one or more transcriptional regulatory sequences operatively linked to a heterologous polynucleotide that results in tumor-specific expression of the heterologous polynucleotide. The transcriptional regulatory sequence can be derived from a genomically imprinted gene, which transcriptional regulatory sequence is more active, or is specifically active, in tumor cells, as compared with non-tumor cells. Many genomically imprinted genes are known in the art and may be useful for the methods of the invention. Preferably, the transcriptional regulatory sequence is H19 promoter, H19 enhancer, IGF-2 P3 promoter, IGF-2 P4 promoter, or a variant thereof.

In one embodiment, the invention relates to a method for treating or preventing cancer, comprising administering to a subject in need thereof an effective amount of a vector comprising a heterologous polynucleotide operably linked to one or more regulatory sequences, wherein the heterologous polynucleotide comprises a sequence encoding a cytotoxic or cytostatic product, and wherein the regulatory sequence is derived from a transcriptional regulatory sequence of an imprinted human gene.

In another embodiment, the invention relates to a method for treating or preventing cancer, comprising administering into a tumor of a subject in need thereof an effective amount of a vector comprising a heterologous polynucleotide operably linked to one or more regulatory sequences, wherein the heterologous polynucleotide comprises a sequence encoding a cytotoxic or cytostatic product, and wherein the regulatory sequence is derived from a transcriptional regulatory sequence of an imprinted human gene.

In another embodiment, the invention relates to a method for reducing cell growth comprising the step of contacting a cell with an effective amount of a vector comprising a heterologous polynucleotide operably linked to one or more regulatory sequences, wherein the heterologous polynucleotide comprises a sequence encoding a cytotoxic or cytostatic product, and wherein the regulatory sequence is derived from a transcriptional regulatory sequence of an imprinted human gene.

In another embodiment, the invention relates to a method for treating or preventing cancer, comprising administering to a subject in need thereof an effective amount of a replicative virus comprising a heterologous polynucleotide operably linked to one or more regulatory sequences, wherein the heterologous polynucleotide comprises a sequence encoding a product essential for viral replication, and wherein the regulatory sequence is derived from a transcriptional regulatory sequence of an imprinted human gene.

In another embodiment, the invention relates to a method for treating or preventing cancer, comprising administering into a tumor of a subject in need thereof an effective amount of a replicative virus comprising a polynucleotide operably linked to one or more regulatory sequences, wherein the polynucleotide comprises a sequence encoding a product essential for viral replication, wherein the regulatory sequence is derived from a transcriptional regulatory sequence of an imprinted human gene.

In another embodiment, the invention relates to a method for reducing cell growth comprising the step of contacting a cancer cell with an effective amount of a replicative virus comprising a polynucleotide operably linked to one or more regulatory sequences, wherein the polynucleotide comprises a sequence encoding a product essential for viral replication, and wherein the regulatory sequence is derived from a transcriptional regulatory sequence of an imprinted human gene.

In particular, H19 expression is activated in a wide array of carcinomas, including but not limited to bladder carcinoma, hepatocellular carcinoma, hepatoblastoma, rhabdomyosarcoma, ovarian carcinoma, cervical carcinoma, lung carcinoma, breast carcinoma, squamous cell carcinoma in head and neck, esophageal carcinoma, thyroid carcinoma, astrocytoma, ganglioblastoma, and neuroblastoma. Also, it has been discovered that constructs containing an H19, IGF-2 P3, IGF-2 P4 or IGF-1 promoter sequence operatively linked to a heterologous polynucleotide, or a construct containing such a promoter sequence in combination with a downstream H19 enhancer, are specifically activated in tumor cells.

Accordingly, in one of its aspects, the invention provides methods and compositions for altering the phenotype of, reducing the growth of, or selectively killing, cancerous cells. In one embodiment, this objective is accomplished by delivering to the cells a vector comprising a heterologous polynucleotide operably linked to one or more transcriptional regulatory sequences, or variants thereof, that are expressed in cancer cells such that the expression of the heterologous polynucleotide results in an altered phenotype or death of the cancer cell. In a particular embodiment, the heterologous polynucleotide can encode a cytostatic or a cytotoxic agent (e.g., a toxin, an antisense RNA, or a ribozyme). In another embodiment, where the vector is a replicative virus, the transcriptional regulatory sequence is operably linked to a viral gene required for replication, i.e., a gene which must be expressed for the virus to replicate normally. Thus, the virus becomes replicative, and hence lytic, upon tumor-specific activation of the transcriptional regulatory sequence.

In a preferred embodiment, a transcriptional regulatory sequence is an H19 promoter, an H19 enhancer, an IGF-2 P3 promoter, an IGF-2 P4 promoter, an IGF-1 promoter, and/or a variant thereof.

5.1 Regulatory Sequences of the Invention

Described herein are regulatory sequences that can be used to direct the preferential expression of a heterologous polynucleotide in tumor cells. For example, sequences comprising transcriptional regulatory sequences (e.g., promoters, enhancers), or variants thereof, of an imprinted, human gene can be useful to direct expression of a heterologous nucleotide in tumor cells.

Sequences derived from the H19 gene can be operatively linked to a heterologous polynucleotide to confer preferential expression of the heterologous polynucleotide in tumor cells. Accordingly, in one embodiment, the H19 transcriptional regulatory sequence comprises an upstream H19 promoter region or a variant thereof. In another embodiment, the H19 transcriptional regulatory sequence comprises an H19 enhancer in a non-coding region of the heterologous polynucleotide. In another embodiment, the H19 transcriptional regulatory sequence comprises a downstream H19 enhancer region. Alternatively, the H19 enhancer region is upstream of the heterologous polynucleotide.

The nucleotide sequence of an H19 promoter region is shown in FIGS. 1A–1C (SEQ ID NO: 1). This 830 nucleotide sequence extends from −837 to −7 nucleotides from the cap site (as described in Brannan et al., supra). A consensus TATA sequence occurs at nucleotides −27 to −35. Two consensus AP2 binding sites (8/9 matches) occur at approximately −500 and −40 nucleotides upstream from the transcription initiation site.

When placed upstream of the coding region for a heterologous polynucleotide, as discussed in more detail below, approximately 830 base pairs of the regulatory region is sufficient to direct expression of an operatively linked heterologous polynucleotide in cancer cells expressing endogenous H19. Additionally, another H19 promoter region between nucleotides −819 to +14 (FIG. 5, SEQ ID NO:2) is also sufficient to direct expression of an operatively linked heterologous polynucleotide in cancer cells. The invention also contemplates using approximately 400, 500, 600, or 700 base pairs of an H19 promoter region to direct expression of an operatively linked heterologous polynucleotide.

A nucleotide sequence comprising an enhancer region of the human H19 gene, or a variant thereof, can optionally be added to a construct comprising an H19 promoter and a heterologous polynucleotide. Such constructs can increase the level of expression in a tumor cell. One or more H19 enhancers can be placed upstream and/or downstream to the heterologous polynucleotide. As described more fully below and illustrated by way of example in Section 6, a downstream H19 enhancer region is encompassed on a SacI restriction fragment extending from +6 kb to +11 kb relative to the start site of transcription. As expected from an enhancer sequence, the enhancer is able to exert its effect when placed in either reverse or direct orientation (relative to the orientation of the H19 enhancer in the endogenous H19 gene) of a heterologous polynucleotide under the control of the H19 promoter. Additionally, variants of the enhancer comprising the sequences as shown in FIGS. 6, 7A–7B and 8A–8C (SEQ ID NOS:3–5) can also be used to facilitate gene expression.

IGF-1 gene expression has been associated with lung cancer and breast cancer. The IGF-1 promoter can comprise about 1000, 1100, 1200, 1300, 1400, 1500, or 1600 base pairs of the human IGF-1 gene sequence between nucleotides 1 to 1630 (Genbank accession number M12659 M77496 incorporated herein by reference; Rotwein et al., 1986, J. Biol. Chem. 261:4828–4832).

An IGF-2 gene product is expressed using any of four different promoter regions. Three of these four promoters are expressed in embryonic tissues. Promoter P1, however, is activated in adult tissues only (Sussenbach et al., 1992, Growth Reg. 2:1–9). IGF-2 gene expression, driven by the P3 promoter, has been implicated in hepatocarcinoma.

Moreover, the P4 promoter (nucleotide sequence −546 to +102 of the IGF-2 gene) and P3 promoter (nucleotide sequence −1229 to +140 of IGF-2 gene) are activated in human bladder cancer cells. Accordingly, the IGF-2 P3 and IGF-2 P4 promoter sequences, or variants thereof, can be used to direct expression of an operatively linked heterologous polynucleotide to cancer or tumor cells. In a further embodiment, the IGF-2 P3 and P4 promoters, or variants thereof, can be used in combination with an H19 enhancer, or variant thereof.

Any of the regulatory sequences of the invention can be altered by additions, substitutions or deletions and assayed for the degree of regulatory tumor-specific expression, or the level of expression of sequences operably linked thereto, in cancer cells. Variants of an H19 enhancer can be tested individually for the ability to enhance transcription under the control of the H19 promoter. Similarly, various positives of the H19 enhancer, or variants thereof relative to the heterologous polynucleotide, can be assayed for its enhancer function.

Alterations in the regulatory sequences can be generated using a variety of chemical and enzymatic methods known to those skilled in the art. For example, regions of the sequences defined by restriction sites can be deleted. Oligonucleotide-directed mutagenesis can be employed to alter the sequence in a defined way and/or to introduce restriction sites in specific regions within the sequence. Additionally, deletion mutants can be generated using DNA nucleases such as Bal31 or ExoIII and S1 nuclease. Progressively larger deletions in the regulatory sequences are generated by incubating the DNA with nucleases for longer periods of time (See, e.g., Ausubel et al., 1989, *Current Protocols for Molecular Biology* for a review of mutagenesis techniques).

Sequence diversity can be introduced by a variety of mutagenesis schemes known in the art. Random, non-specific methods of introducing mutations include classical in vivo mutagenesis techniques, such as exposure of entire organisms to radiation or chemical mutagens, or use of transposons. More localized mutations in microorganisms in vivo can be performed by using mutator strains of bacteria, transducing phages, episomes, or homologous recombination.

Mutations can be induced in vitro by many other methods in addition to homologous recombination and random mutagenesis, which include deletion analysis, linker mutations, reporter gene fusion, restriction/ligation assembly, oligonucleotide-directed mutagenesis, and cassette mutagenesis. PCR-based methods that can introduce sequence diversity are also available such as error-prone PCR and assembly PCR (also known as parallel PCR). Furthermore, various combinations of the above techniques have led to specialized methods which include sexual PCR (also known as DNA shuffling), recursive ensemble mutagenesis and exponential ensemble mutagenesis.

Homologous recombination occurs naturally in living cells. In eucaryotes, homologous recombination occurs at meiosis, and is thought to be one of the inherent evolutionary mechanisms. A number of patents describe the use of in vivo homologous recombination to manipulate DNA sequences (See, e.g., Gray, U.S. Pat. No. 5,093,257 entitled "Hybrid Prokaryotic Polypeptides Produced By In Vivo Homologous Recombination"; Kucherlapati et al., U.S. Pat. No. 5,413,923, entitled "Homologous Recombination for Universal Donor Cells and Chimeric Mammalian Hosts"; Khosla et al., U.S. Pat. No. 5,521,077, entitled "Method of Generating Multiple Protein Variants and Populations of Protein Variants Prepared Thereby"; Fell, Jr. et al., U.S. Pat. No. 5,202,238, entitled "Production of Chimeric Antibodies by Homologous Recombination"; Zarling et al., U.S. Pat. No. 5,763,240, entitled "In Vivo Homologous Sequence Targeting in Eukaryotic Cells"; and Sherwin et al., U.S. Pat. No. 6,015,708, entitled "Gene Manipulation and Expression Using Genomic Sequences").

Means of performing random, or localized random, in vitro mutagenesis are essentially similar to those that can be used for in vivo mutagenesis, e.g., irradiation, chemical mutagens, transposon mutagenesis. Aside from random mutagenesis methods, any of various techniques by which specific mutations can be made in vitro can be considered to be a form of site-directed mutagenesis (Kendrew, J., 1994, in *The Encyclopedia of Molecular Biology*, Blackwell Science Inc., London). Non-PCR-based in vitro approaches to site-directed mutagenesis can be grouped generally into the categories of oligonucleotide-directed mutagenesis, methods that restructure fragments of DNA (e.g., cassette mutagenesis, gene assembly), and localized random mutagenesis (Botstein and Shortle, 1985, Science 229, 1193–1201).

All oligonucleotide-directed mutagenesis is based on the same concept—an oligonucleotide encoding the desired mutation(s) is annealed to one strand of the DNA of interest and serves as a primer for initiation of DNA synthesis to produce a strand containing the mutation. Various forms of the basic technique, including single or multiple substitutions, insertions or deletions, are described by Kramer et al., 1982, Nucleic Acids Res. 10:6475–6485; Zoller and Smith, 1982, Nucleic Acids Res.10:6487–6500; Smith et al., 1982, "Site-Directed Mutagenesis", Trends in Biochem. Sci., 7:440–442; and Norris et al., 1983, Nucleic Acids Res. 11:5103–5112.

Cassette mutagenesis is characterized by replacement, typically by restriction/ligation, of a portion of the endogenous gene with a "cassette", which often is a synthetic oligonucleotide (See, e.g., Estell et al., 1985, "Engineering an enzyme by site-directed mutagenesis to be resistant to chemical oxidation", J. Biol. Chem. 260(11):6518–6521; Wells et al., 1985, "Cassette mutagenesis: an efficient method for generation of multiple mutations at defined sites", Gene 34:315–323; Beck von Bodman et al.,1986, "Synthesis, bacterial expression, and mutagenesis of the gene coding for mammalian cytochrome b5", Proc Natl Acad Sci. 83:9443–9447; Reidhaar-Olson and Sauer, 1988, "Combinatorial cassette mutagenesis as a probe of the informational content of protein sequences", Science 241: 53–57; Ratzkin et al., U.S. Pat. No.4,894,331, entitled "Partial Marker Cassette Mutagenesis of Xylose Isomerase"; Estell et al., U.S. Pat. No. 5,155,033, entitled "Subtilisins Modified at Position 225 Resulting in a Shift in Catalytic Activity"; Estell et al., U.S. Pat. No. 5,182,204, entitled "Non-Human Carbonyl Hydrolase Mutants, Vectors Encoding Same and Hosts Transformed with Said Vectors").

Gene assembly entails the use of oligonucleotides, which can be a mixture of synthetic oligomers and fragmented native sequences. Stochastic polymerization of the oligonucleotide pool by treatment with a DNA ligase results in the assembly of novel polynucleotide sequences (See, e.g., Kauffman et al., U.S. Pat. No. 5,723,323, entitled "Method of Identifying a Stochastically-generated Peptide, Polypeptide, or Protein Having Ligand Binding Property and Compositions Thereof").

Error-prone PCR is a means of randomly introducing several point mutations in a PCR product as a result of using a DNA polymerase that demonstrates low fidelity (See, e.g., Leung et al., 1989, "A method for random mutagenesis of a defined DNA segment using a modified polymerase chain reaction", Technique 1:11–15, 1989; U.S. Pat. No. 5,223, 408, entitled "Method for Making Variant Secreted Proteins with Altered Properties").

Assembly PCR describes a process whereby, using a pool of oligonucleotides, many different PCR reactions occur in parallel in the same reaction mixture, with the products of one PCR reaction priming the products of another reaction (Stemmer et al., 1995, "Single-step assembly of a gene and entire plasmid from large numbers of oligodeoxyribonucleotides", Gene164:49–53). The method relies on DNA polymerase, rather than DNA ligase, to build increasingly longer DNA fragments during the assembly process (See, e.g., Stemmer, U.S. Pat. No. 5,605,793, entitled "Methods for in Vitro Recombination"; Short, U.S. Pat. No. 5,830,696, entitled "Directed Evolution of Thermophilic Enzymes").

In sexual PCR, also called DNA shuffling, related but not identical DNA sequences are randomly fragmented, after which the fragments are reassembled by assembly PCR under conditions that permit homologous recombination (Stemmer, 1994, "Rapid evolution of a protein in vitro by DNA shuffling", Nature 370:389–391). Repeated cycles of point mutagenesis, recombination, and selection produces in vitro molecular evolution. This process is repeated for as many cycles as necessary to obtain a desired property or function (Stemmer, 1994, "DNA shuffling by random fragmentation and reassembly: in vitro recombination for molecular evolution", Proc Natl Acad Sci. 91:10747–10751).

Recursive Ensemble Mutagenesis ("REM") is a protein engineering method that employs multiple cycles of cassette mutagenesis to identify "optimal" amino acids at targeted positions in a given protein. REM uses information gained from previous iterations of combinatorial cassette mutagenesis to search sequence space more efficiently. Through multiple rounds of optimized point mutation and recombination, rapid evolution of DNA sequences is achieved (Arkin and Youvan, 1992, "An Algorithm for Protein Engineering: Simulations of Recursive Ensemble Mutagenesis", Proc Natl Acad Sci. 89:7811–7815; Delagrave et al., 1993, "Recursive Ensemble Mutagenesis", Protein Engineering 6:327–33 1).

In exponential ensemble mutagenesis, several nucleotides are randomized in parallel to identify amino acids, at each altered position, that lead to functional proteins. The method thereby generates combinatorial libraries with a high percentage of optimized proteins. Exponential ensemble mutagenesis can be advantageous when it is desirable to change many residues simultaneously. With the greater frequency of functional mutants which is obtained by this method, entire proteins can be mutagenized combinatorially (Delagrave and Youvan, 1993, "Searching Sequence Space to Engineer Proteins: Exponential Ensemble Mutagenesis", Biotechnology 11:1548–1552; Khosla et al., U.S. Pat. No. 5,521,077, entitled "Method of Generating Multiple Protein Variants and Populations of Protein Variants Prepared Thereby").

The altered sequences created by use of any technique known in the art to introduce sequence diversity, including those disclosed herein, are evaluated for their ability to direct tumor-specific expression of heterologous polynucleotides in appropriate host cells, particularly H19-expressing carcinoma-derived cells (e.g., bladder carcinoma cells, to name an example). It is within the scope of the present invention to use any altered regulatory sequence that can direct tumor-specific expression to create a recombinant expression vector.

A wide variety of heterologous polynucleotides can be expressed under the control of the transcriptional regulatory sequences useful for the methods of the invention such as, but not limited to, genes encoding toxic gene products, potentially toxic gene products, anti-proliferative gene products, cytostatic gene products, and gene products essential for viral replication. Also encompassed by heterologous gene products useful for the invention are antisense and ribozyme RNAs that have a cytotoxic or cytostatic effect on the target cell. The heterologous polynucleotide can also be a marker gene such as, but not limited to, an enzyme (e.g., CAT, beta-galactosidase, luciferase), fluorescent protein (e.g., green fluorescent protein), or antigenic marker.

Cytotoxic products are broadly defined to include toxins and apoptosis-inducing agents. Cytotoxic agents produce a toxic effect on cells, preferably killing the target cell. Examples of cytotoxic products that can be used in methods of the invention include, but are not limited to, thymidine kinase, diphtheria toxin, Pseudomonas toxin, ricin, cholera toxin, PE40, tumor suppressor genes (e.g., the retinoblastoma gene and p53), and variants thereof.

Additionally, sequences encoding polypeptides that induce cell apoptosis can be used. Such polypeptides include, but are not limited to, the Alzheimer's Abeta peptide (See, e.g., LaFerla et al., 1995, Nat. Genet. 9:21–30), atrial natriuretic peptide (See, e.g., Wu et al., 1997, J. Biol. Chem.72:14860–14866), calcitonin gene-related peptide (See, e.g., Sakuta et al., 1996, J. Neuroimmunol. 67:103–109), tumor necrosis factor, transforming growth factor-beta, Fas, and variants thereof. Other apoptosis-inducing polypeptides useful for the invention include Bcl-x, Bak, Ced-4, Mch6, ICE family of cell death proteases, and variants thereof.

Polynucleotides encoding a proapoptotic polypeptide are useful for the methods of the invention. Several proapoptotic polypeptides are known in the art and include, but are not limited to, p75, androgen receptor, BID, DCC, huntingtin interacting protein (HIP-1), Bcl-2/Bcl-XL-associated death promoter (Bad), Machado-Joseph disease gene product, SCA1, SCA2, SCA6, atrophin-1 polypeptide, PUMA (Nakano and Vusden, 2001, "PUMA, a novel proapoptotic gene, is induced by p53:, Mol Cell. 7:683–694), SATLDAL-LAALRRI (SEQ ID NO:12), .Q14, SATLDALLAALGGI (SEQ ID NO:13), SATLDALLAALRGI (SEQ ID NO:14), SATLQALLAALRRI (SEQ ID NO:14), and variants thereof.

Further, agents that promote apoptosis by, for example, reducing the activity of certain growth factors, affecting cellular attachment to the extracellular matrix, lowering intracellular calcium, or increasing glucocorticoid levels can also be used in accordance with the methods of the invention.

Additionally, for purposes of the present invention, a cytotoxic product includes a drug-metabolizing enzyme which converts a pro-drug into a cytotoxic product. Drug metabolizing enzymes that convert a pro-drug into a cytotoxic product include, but are not limited to, thymidine kinase (from herpes simplex virus or varicella zoster virus), cytosine deaminase, nitroreductase, cytochrome p-450 2B1, thymidine phosphorylase, E. coli guanine phosphoribosyl transferase, purine nucleoside phosphorylase, alkaline phosphatase, carboxypeptidases A and G2, linamarase, β-lactamase, xanthine oxidase, and variants thereof (See, e.g., Pandha et al., 1999, "Genetic prodrug activation therapy for breast cancer: A phase I clinical trial of erbB-2-directed suicide gene expression", J Clin Oncol. 17:2180–2189; Rigg and Sikora, 1997, "Genetic prodrug activation therapy", Mol Med Today. 3:359–366).

Polynucleotides encoding cytostatic agents (i.e., agents that suppresses cell growth and multiplication) are useful for the methods of the invention. Cytostatic agents known to block the cell cycle and arrest cell proliferation include, but are not limited to, gene products derived from p21 (Waf1), p27 (Kip1), p53, p53175P, p57 (Kip2), p15 (INK4b), p16 (INK4a), p18(INK4c), p19(Arf), p73, GADD45, APC1, p73RB1, WT1, NF1, VHL, and variants thereof (Koga et al., 2001, "Involvement of p21(WAF1/Cip1), p27(Kip1), and p18(INK4c) in troglitazone-induced cell-cycle arrest in human hepatoma cell lines", Hepatology. 33:1087–1097; Huang et al., 2001, "p53/p21(CIP1) cooperate in enforcing rapamycin-induced G(1) arrest and determine the cellular response to rapamycin", Cancer Res. 61:3373–3381; Li et al., 2001, "Pharmacological inhibition of fatty acid synthase activity produces both cytostatic and cytotoxic effects modulated by p53", Cancer Res. 61:1493–1499; Mazur et al., 1998, "Higher productivity of growth-arrested Chinese hamster ovary cells expressing the cyclin-dependent kinase inhibitor p27", Biotechnol Prog. 14:705–713; Tsugu et al., 2000, "Expression of p57(KIP2) potently blocks the growth of human astrocytomas and induces cell senescence. Am J Pathol. 157:919–932; Dyer et al., 2001, "p27Kip1 and p57Kip2 regulate proliferation in distinct retinal progenitor cell populations", J Neurosci. 21:4259–4571; Kovalev et al., 2001, "An Important Role of CDK Inhibitor p18(INK4c) in Modulating Antigen Receptor-Mediated Cell Proliferation", J Immunol. 167:3285–3292; Modesitt et al., 2001, "In vitro and in vivo adenovirus-mediated p53 and p16 tumor suppressor therapy in ovarian cancer. Clin Cancer Res. 7:1765–1772; Wong et al., 2001, "Differential expression of p16/p21/p27 and cyclin D1/D3, and their relationships to cell proliferation, apoptosis, and tumour progression in invasive ductal carcinoma of the breast", J Pathol.194: 35–42; Shapiro et al., 2000, "The physiology of p16 (INK4A)-mediated G1 proliferative arrest", Cell Biochem Biophys. 33:189–197; Fuxe et al., 2000, "Adenovirus-mediated overexpression of p15INK4B inhibits human glioma cell growth, induces replicative senescence, and inhibits telomerase activity similarly to p16INK4A", Cell Growth Differ. 11:373–384; Latres et al., 2000, "Limited overlapping roles of P15(INK4b) and P18(INK4c) cell cycle inhibitors in proliferation and tumorigenesis", EMBO J. 19:3496–3506; Weber et al., 2000, "p53-independent functions of the p19(ARF) tumor suppressor", Genes Dev. 14:2358–2365; Sasaki et al., 2001, "Adenovirus-mediated transfer of the p53 family genes, p73 and p51/p63 induces cell cycle arrest and apoptosis in colorectal cancer cell lines: potential application to gene therapy of colorectal cancer", Gene Ther. 8:1401–1408; Zhu et al., 1998, "The potential tumor suppressor p73 differentially regulates cellular p53 target genes.", Cancer Res. 58:5061–5065; Mullan et al., 2001, "BRCA1 and GADD45 mediated G2/M cell cycle arrest in response to antimicrotubule agents", Oncogene. 20:6123–6131; Velasco-Miguel et al., 1999, "Protein PA26, a novel target of the p53 tumor suppressor and member of the GADD family of DNA damage and growth arrest inducible genes", Oncogene. 18:127–137; Jorgensen et al., 2001, "Characterisation of the human APC1, the largest subunit of the anaphase-promoting complex", Gene. 262: 51–59; Kurasawa and Todokoro, 1999, "Identification of human APC10/Doc1 as a subunit of anaphase promoting complex", Oncogene 18:5131–5137; Basu et al., 1999, "Tumor suppressor protein WT1 inhibits autonomous DNA replication directly, as well as indirectly by causing loss of replicated DNA as a consequence of cell death induced by the protein", Int J Oncol. 15:701–708; Yamagami et al., 1998, "Suppression of Wilms' tumor gene (WT1) expression induces G2/M arrest in leukemic cells", Leuk Res. 22:383–384; Murata et al., 1997, "The Wilms tumor suppressor gene WT1 induces G1 arrest and apoptosis in myeloblastic leukemia M1 cells", FEBS Lett. 409:41–45; Uhlmann et al., 2001, "Tumor suppressor gene regulation of cell growth: recent insights into neurofibromatosis 1 and 2 gene function", Cell Biochem Biophys.34:61–78; Zhang et al., 1998, "Nf1 regulates hematopoietic progenitor cell growth and ras signaling in response to multiple cytokines. J Exp Med. 187:1893–1902; Norton et al., 1996, "Expression of the neurofibromatosis 1 (NF1) gene during growth arrest", Neuroreport. 7:601–604; Baba et al., 2001, "Tumor suppressor protein VHL is induced at high cell density and mediates contact inhibition of cell growth", Oncogene. 20:2727–2736; Davidowitz et al., 2001, "VHL induces renal cell differentiation and growth arrest through integration of cell-cell and cell-extracellular matrix signaling", Mol Cell Biol. 21:865–874).

Any of the herein described cytostatic compound, or any other compound known in the art that the skilled artisan can recognize to be useful as a cytostatic agent, can be useful for the methods of the present invention. The use of polynucleotides encoding cytostatic agents can be particularly advantageous for sensitizing a cancer cell or tumor to subsequent challenge with another cancer therapeutic agent, for example.

Polynucleotides encoding agents that stimulate a cytostatic or cytotoxic response can also be useful for the methods of the invention. Such agents include, but are not limited to, thymidine kinase, interferons (e.g., alpha-interferon, beta-interferon, gamma-interferon), interferon inducers (e.g., *Brucella abortus*, and various viral agents), thymic factors (e.g., thymosin fraction 5, thymosin alpha-1), and variants thereof. Further, agents that stimulate an immune response can be useful for the methods of the invention. Examples of such agents include, but are not limited to, lymphokines (e.g., IL-1, IL-2, IL-3, IL-4), colony stimulating factors (e.g., G-CSF, GM-CSF, and M-CSF), and variants thereof.

Although the present invention relates to cell-specific expression of heterologous polynucleotides to target cancer cells, greater specificity of treatment can be achieved by using cancer-specific delivery of the vectors of the invention. For example, antibodies that recognize cell surface antigens unique to cancer cells, or more prevalent on cancer cells, compared to normal cells are known in the art, and can be used together with a vector of the invention to specifically target and kill tumor cells (See, e.g., Dillman, "Antibody Therapy: Principles of Cancer" Oldham (ed.), Raven Press, Ltd., New York, 1987).

Additionally, the present invention contemplates the use of an antisense, antigene, or aptameric oligonucleotide as a heterologous sequence. These sequences can then be delivered to cancer cells using the presently described expression constructs. Ribozymes or single-stranded RNA can be expressed in a cancer cell to inhibit the expression of a particular gene of interest. The target genes for these antisense or ribozyme molecules preferably encode gene products involved in cell maintenance or maintenance of the cancerous cell phenotype. Such target genes include, but are not limited to, cdk2, cdk8, cdk21, cdc25A, cyclindD1, cyclinE, cyclinA and cdk4.

For example, vectors comprising heterologous polynucleotides encoding antisense RNAs or ribozymes specific for the transcripts of oncogenic forms of p53, c-fos, c-jun, Kr-ras and/or Her2/neu operably linked to transcriptional regulatory sequences of the invention are introduced into cells to down regulate expression of the endogenous genes. Tumor cells that express H19, and can activate an H19 transcriptional regulatory sequence (or which specifically activate an IGF-1, IGF-2 P3, or IGF 2 P4 promoter) can be specifically targeted for expression of an antisense RNA or ribozyme RNA.

Antisense approaches involve the design of oligonucleotides (in this case, mRNA) that are complementary to the target mRNA. The antisense oligonucleotides will bind to the complementary target mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the target message, e.g., the 5' untranslated sequence up to and including the AUG initiation codon, can efficiently inhibit translation. Sequences complementary to the 3' untranslated sequences of mRNAs can also effectively inhibit translation as well (See, e.g., Wagner, 1994, Nature 372:333–335). Thus, oligonucleotides complementary to either the 5'n or 3'-un-translated, non-coding regions of the target gene transcripts can be used in an antisense approach to inhibit translation of endogenous genes. Oligonucleotides complementary to the 5' untranslated region of the mRNA preferably include the complement of the AUG start codon. Antisense oligonucleotides complementary to mRNA coding regions may be less efficient inhibitors of translation but can be used in accordance with the invention. Whether designed to hybridize to the 5', 3' or coding region of the target mRNA, antisense nucleic acids preferably are at least six nucleotides in length, more preferably ranging from 6 to about 50 nucleotides in length. In specific aspects, the oligonucleotide is at least 10 nucleotides, at least 17 nucleotides, at least 25 nucleotides or at least 50 nucleotides in length.

Regardless of the choice of target sequence, it is preferred that in vitro studies are first performed to assess the ability of the antisense oligonucleotide to inhibit gene expression. These studies preferably utilize controls that distinguish between antisense gene inhibition and nonspecific biological effects of oligonucleotides. It is also preferred that these studies compare levels of the target RNA or protein with that of an internal control RNA or protein.

Ribozyme molecules designed to catalytically cleave an essential target gene can also be used to prevent translation of target mRNA (See, e.g., PCT International Publication WO90/11364, published Oct. 4, 1990; Sarver et al., 1990, Science 247:1222–1225). When the ribozyme is specific for a gene transcript encoding a protein involved in cancer cell growth, such ribozymes can cause reversal of a cancerous cell phenotype. While ribozymes that cleave mRNA at site-specific recognition sequences can be used to destroy target mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. Construction and production of hammerhead ribozymes is known in the art (See, e.g., Haseloff and Gerlach, 1988, Nature, 334:585–591). Preferably the ribozyme is engineered so that the cleavage recognition site is located near the 5' end of the target mRNA; i.e., to increase efficiency and minimize the intracellular accumulation of non-functional mRNA transcripts.

Ribozymes for use in the present invention also include RNA endoribonucleases (hereinafter "Cech-type ribozymes") such as the one which occurs naturally in *Tetrahymena thermophila* (also known as the IVS, or L-19 IVS RNA) (See, e.g., Zaug et al., 1984, Science, 224: 574–578; Zaug and Cech, 1986, Science, 231:470–475; Zaug et al., 1986, Nature, 324:429–433; published International Patent Application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention contemplates the use of those Cech-type ribozymes which target eight base-pair active site sequences that are present in target genes.

Where the vector of the polynucleotide is a replicative virus, the lytic effect of the replicating virus can have therapeutic benefit by placing a gene product that permits viral replication under the control of a regulatory sequence of the invention. Preferably, the gene product is essential for viral replication. Examples of viruses and suitable gene products that can be placed under the control of a regulatory sequence of the invention are provided by Alemany et al., (2000, "Replicative adenoviruses for cancer therapy", Nature Biotechnology, 18:723–727). A particularly preferred virus is the adenovirus.

While most gene therapy studies involve the use of replication-deficient viruses to deliver the expression construct, several recent studies have investigated the feasibility of using replicative viruses, in particular replicative adenoviruses, as the oncolytic agent in gene therapy. The concept is based on the use of the virus' intrinsic lytic properties, alone or in combination with a cytotoxic product, for the destruction of the tumor.

In one embodiment, viral genes that are dispensable in tumor cells, or viral genes such as those responsible for activation of cell cycle through p53 or Rb binding, are completely or partially deleted. In another embodiment, transcription of viral genes is controlled by replacing the viral promoter with a promoter that is more active in tumor cells as compared to healthy cells (See, e.g., Balague et al., 2001, "Human papillomavirus e6e7-mediated adenovirus cell killing: selectivity of mutant adenovirus replication in organotypic cultures of human keratinocytes", J Virol. 75:7602–7611; Yamamoto et al., 2001, "Characterization of the cyclooxygenase-2 promoter in an adenoviral vector and its application for the mitigation of toxicity in suicide gene therapy of gastrointestinal cancers", Mol Ther. 3:385–394; Suzuki et al., 2001, "A conditionally replicative adenovirus with enhanced infectivity shows improved oncolytic potency", Clin Cancer Res. 2001 January;7:120–126; Alemany et al., 2000, Nature Biotechnology, 18: 723–727). In a preferred embodiment, a native transcriptional regulatory sequence of a viral gene involved in viral replication is replaced with a transcriptional regulatory sequence derived from an imprinted gene, such that the gene product is preferentially expressed in tumor cells. The advantages of using a transcriptional regulatory sequence derived from an imprinted gene, in accordance with the present invention, are described herein.

5.2 Activation of Genes in Tumor Cells

Expression driven by H19, IGF-2 P3, and IGF-2 P4 in tumors and cell lines can be determined using the techniques of RNA analysis, in situ hybridization, or reporter gene constructs. In addition, tumor cells with activated IGF-1 gene expression can be similarly determined and targeted in gene therapy using the IGF-1 promoter to direct expression of a heterologous polynucleotide.

For most RNA analysis applications, a labeled probe that specifically hybridizes to the gene transcript of interest is prepared using any number of techniques well known in the art. The labeled probe can contain at least 15–30 bases complementary to the H19 nucleotide sequence, and more preferably contains at least 50 to 150 bases complementary to the H19 transcript. A particularly preferred hybridization probe for H19 expression is a polynucleotide complementary to the 3' end of the H19 message from approximately 800 base pairs upstream of the poly A site to the poly A site.

In a specific embodiment of the invention illustrated below by way of working example, a labeled antisense RNA probe is generated in vitro using a T7 or T3 expression plasmid. H19 probes can also be labeled by random priming in the presence of labeled nucleotide, for example, using the Prime-It kit (Stratagene™, La Jolla, Calif.; Catalog No. 300392). Alternatively, labeled probes can be generated in a PCR reaction using a cDNA clone of the H19 coding region and primers designed to amplify a region of the coding region, or by a standard nick translation reaction.

Labels appropriate for polynucleotide probes include nucleotides incorporating radioactive isotopes (such as $^{35}$S and $^{32}$P), fluorescent, luminescent and color tags, and enzymatic moieties.

The labeled probe is hybridized in situ to a cell or tissue sample using standard techniques such as described below by way of working example, and in co-pending U.S. patent application Ser. No. 08/704,786, incorporated herein by reference. Alternatively, if a sufficient quantity of the appropriate cells can be obtained, standard RNA analysis (e.g., Northern analysis, RNase protection, or primer extension) can be performed to determine the level of mRNA expression of the gene of interest.

Additionally, such gene expression assays can be performed "in situ", i.e., directly upon tissue sections (fixed and/or frozen) of patient tissue obtained from biopsies or resections, such that no nucleic acid purification is necessary. Nucleic acid reagents such as those described above can be used as probes and/or primers for such in situ procedures (See, e.g., Nuovo, 1992, "PCR In Situ Hybridization: Protocols And Applications", Raven Press, NY).

An alternative method to determine if a cell type or tumor will be capable of specifically activating expression constructs containing the particular transcriptional regulatory sequences operatively linked to a heterologous polynucleotide is to actually transfect such expression constructs into the cell. For these purposes, the heterologous polynucleotide is preferably a marker gene product. A positive result in an assay for the marker gene product reveals that the cell or cell line is capable of activating expression from the transcriptional regulatory sequences.

Using these techniques, exemplary tumor types with activated H19 expression are as follows:
A. Pediatric solid tumors
1. Wilm's tumor
2. Hepatoblastoma
3. Embryonal rhabdomyosarcoma
B. Germ cell tumors and trophoblastic tumors
1. Testicular germ cell tumors
2. Immature teratoma of ovary
3. Sacrococcygeal tumor
4. Choriocarcinoma
5. Placental site trophoblastic tumors
C. Epithelial adult tumors
1. Bladder carcinoma
2. Hepatocellular carcinoma
3. Ovarian carcinoma
4. Cervical carcinoma
5. Lung carcinoma
6. Breast carcinoma
7. Squamous cell carcinoma in head and neck
8. Esophageal carcinoma
9. Thyroid carcinoma
D. Neurogenic tumors
1. Astrocytoma
2. Ganglioblastoma
3. Neuroblastoma Accordingly, the cancers listed in the above nonexclusive list are treatable by the methods of the invention. In fact, any tumors which activate H19 expression can be treated by the methods of the invention.

Moreover, the aforementioned techniques can be applied to determine tumors that activate the IGF-1, IGF-2 P3, and IGF-2 P4 promoters. Such tumors are also treatable by the methods of the invention. For example, IGF-2 is activated in childhood tumors, such as, for example, Wilm's tumors, rhabdomyosarcomas, neuroblastomas, and hepatoblastomas.

The invention described herein encompasses a method for preventing or treating cancer comprising administering to a subject in need of such therapy a therapeutically effective amount of a vector of the invention. Accordingly, the vectors of the invention can be used to modulate the development and progression of cancer, which includes, but is not limited to, neoplasms, tumors, carcinomas, sarcomas, adenomas, myeloid lymphomas, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leimyosarcoma, rhabdotheliosarcoma, colon carcinoma, pancreatic cancer, liver cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependynoma, pinealoma, hemangioblastoma, retinoblastoma, leukemia (e.g. acute lymphocytic leukemia), acute myelocytic leukemia (myelolastic, promyelocytic, myelomonocytic, monocytic and erythroleukemia), chronic leukemia (chronic myelocytic (granulocytic) leukemia and chronic lymphocytic leukemia), polycythemia vera, lymphoma (Hodgkin's disease and non-Hodgkin's diseases), multiple myeloma, Waldenström's macroglobulinemia, rectal carcinoma, head and neck cancer, brain cancer, cancers of unknown primary site, cancers of the peripheral nervous system, cancers of the central nervous system, acoustic neuroma, oligodendroglioma, meningioma, neuroblastoma, heavy chain disease, metastases, and any disease or disorder characterized by uncontrolled or abnormal cell growth.

Accordingly, in one embodiment, the present invention provides a method for treating or preventing cancer, comprising administering to a subject in need thereof an effective amount of a vector comprising a heterologous polynucleotide operably linked to one or more transcriptional regulatory sequences, wherein the transcriptional regulatory sequence is preferably derived from an H19, IGF-1, IGF-2 P3 or IGF-2 P4 promoter sequence. In a specific embodiment, the vector is administered by direct injection into the tumor or cancerous tissue. In another specific embodiment, the vector is administered by systemic administration (e.g., intravenous infusion). In yet another specific embodiment, the vector is administered into the lumen of a tissue or organ (e.g., intravesically).

In another embodiment, the present invention provides a method of reducing cell growth comprising the step of contacting a cell with an effective amount of a vector comprising a heterologous polynucleotide operably linked to one or more transcriptional regulatory sequences, wherein the transcriptional regulatory sequence is preferably derived from an H19, IGF-1, IGF-2 P3 or IGF-2 P4 promoter sequence. Cells are preferably hyperproliferative or cancerous (e.g., tumor cells). Reducing growth of the cells is intended to encompass inhibition of cell growth, inhibition of cell division, and cell damage, including damage leading to cell death.

In another embodiment, the present invention provides a method for treating or preventing cancer, comprising administering to a subject in need thereof an effective amount of a replicative virus, wherein the replicative virus comprises a polynucleotide, the expression of which is essential to viral replication, operably linked to one or more transcriptional regulatory sequences, and wherein the transcriptional regulatory sequence is preferably derived from an H19, IGF-1, IGF-2 P3 or IGF-2 P4 promoter sequence.

In a specific embodiment, the replicative virus is administered by direct injection into the tumor or cancerous tissue. In another specific embodiment, the replicative virus is administered by systemic administration (e.g., intravenous infusion). In yet another specific embodiment, the replicative virus is administered into the lumen of a tissue or organ (e.g., intravesically). In a further embodiment, the replicative virus is administered in combination with an effective amount of a heterologous polynucleotide operably linked to one or more transcriptional regulatory sequences, wherein the heterologous polynucleotide encodes a cytotoxic or cytostatic product.

In another embodiment, the present invention provides a method of reducing cell growth comprising the step of contacting a cell with an effective amount of a replicative virus, wherein the replicative virus comprises a polynucleotide, the expression of which is essential for viral replication, operably linked to one or more transcriptional regulatory sequences, and wherein the transcriptional regulatory sequence is preferably derived from an H19, IGF-1, IGF-2 P3 or IGF-2 P4 promoter sequence.

The present invention also relates to a method for increasing a subject's sensitivity to a therapeutic agent, comprising administering to a subject in need thereof an effective amount of a vector comprising a heterologous polynucleotide operably linked to one or more regulatory sequences, wherein the regulatory sequence is preferably derived from an H19, IGF-1 or IGF-2 transcriptional regulatory sequence; and another therapeutic agent. The other therapeutic agent can be administered prior to, concurrently, or subsequent to administration of the vectors of the invention. In one further embodiment, the regulatory sequence is preferably derived from an H19, IGF-1, IGF-2 P3 or IGF-2 P4 promoter sequence. In a further embodiment, the regulatory sequence comprises an enhancer sequence that is more active, or specifically expressed, in cancer cells. In a further specific embodiment, the vector comprises a heterologous polynucleotide that encodes a cytostatic product. In yet a further specific embodiment, the vector comprises a heterologous polynucleotide that encodes a cytotoxic product.

The present invention also relates to a method for increasing a subject's sensitivity to a therapeutic agent, comprising administering to a subject in need thereof an effective amount of a replicative virus, wherein the replicative virus comprises a polynucleotide operably linked to one or more regulatory sequences, and wherein the regulatory sequence is preferably derived from an H19, IGF-1 or IGF-2 transcriptional regulatory sequence. The other therapeutic agent can be administered prior to, concurrently, or subsequent to administration of the vectors of the invention. In one further embodiment, the regulatory sequence is preferably derived from an H19, IGF-1, IGF-2 P3 or IGF-2 P4 promoter sequence. In another further embodiment, the transcriptional regulatory sequence comprises an enhancer sequence that is more active, or specifically expressed, in cancer cells. In a particular embodiment, expression of the polynucleotide comprises a sequence encoding a product important for viral replication. In another particular embodiment, expression of the polynucleotide comprises a sequence encoding a product essential for viral replication. In yet another particular embodiment, the polynucleotide is a heterologous polynucleotide.

The present invention also provides for a method of increasing a cell's sensitivity to a therapeutic agent, comprising the step of contacting the cell with an effective amount of a vector comprising a heterologous polynucleotide operably linked to one or more regulatory sequences, wherein the regulatory sequence is more active, or specifically expressed, in a cancer cell. In a particular embodiment, the regulatory sequence is preferably derived from an H19, IGF-1 or IGF-2 transcriptional regulatory sequence. In a particular further embodiment, the regulatory sequence is preferably derived from an H19, IGF-1, IGF-2 P3 or IGF-2 P4 promoter sequence. In a further embodiment, the regulatory sequence comprises an enhancer sequence that is more active, or specifically expressed, in cancer cells. In a further specific embodiment, the vector comprises a heterologous polynucleotide that encodes a cytostatic product. In yet a further specific embodiment, the vector comprises a heterologous polynucleotide that encodes a cytotoxic product. In a specific embodiment, the cell is a cancer cell.

The present invention also provides for a method of increasing a cell's sensitivity to a therapeutic agent comprising the step of contacting a cell with an effective amount of a replicative virus, wherein the replicative virus comprises a polynucleotide operably linked to one or more regulatory sequences, and wherein the regulatory sequence is more active, or specifically expressed, in a cancer cell. In a particular embodiment, the regulatory sequence is preferably derived from an H19, IGF-1 or IGF-2 transcriptional regulatory sequence. In a particular further embodiment, the regulatory sequence is preferably derived from an H19, IGF-1, IGF-2 P3 or IGF-2 P4 promoter sequence. In another particular further embodiment, the transcriptional regulatory sequence comprises an enhancer sequence that is more active, or specifically expressed, in cancer cells. In a specific embodiment, expression of the polynucleotide comprises a sequence encoding a product important for viral replication. In another specific embodiment, expression of the polynucleotide comprises a sequence encoding a product essential for viral replication. In yet another particular embodiment, the polynucleotide is a heterologous polynucleotide.

In one embodiment, the heterologous polynucleotide comprises a sequence encoding a cytotoxic or cytostatic product (e.g., thymidine kinase, diphtheria toxin, Pseudomonas toxin, ricin, cholera toxin, retinoblastoma gene, p53).

In another embodiment, the polynucleotide comprises a sequence encoding a product involved in viral replication. In another embodiment, the replicative virus is an adenovirus.

In one embodiment, the transcriptional regulatory sequence comprises a promoter from an imprinted gene. In a preferred embodiment, the transcriptional regulatory sequence comprises an H19 promoter, an H19 enhancer, or both an H19 promoter and enhancer. In another preferred embodiment, the H19 enhancer is placed 3' to the heterologous polynucleotide.

5.3 Methods of Introducing Polynucleotides Under the Control of Regulatory Sequences into Host Cells The invention also pertains to a host cell transfected with vectors comprising a transcriptional regulatory sequence operatively linked to a heterologous polynucleotide. Such host cells can be maintained in culture or found within an animal, preferably a mammal. A wide range of vectors, some of which are exemplified herein, can be used in accordance with the presently disclosed methods and materials. Such vectors can be produced using well established molecular biology techniques (See generally, Sambrook et al., 1989, *Molecular Cloning* Vols. I–III, Cold Spring Harbor Laboratory Press, Cold Spring Harbor, N.Y.; *Current Protocols in Molecular Biology* (1989) John Wiley & Sons, all Vols. and periodic updates thereof, herein incorporated by reference). Typically, where translation is desired, the heterologous polynucleotides of interest will also be engineered to comprise a suitable 3' polyadenylation sequence if necessary.

5.3.1 Cultured Cells

Host cells transfected with vectors containing heterologous polynucleotides of the invention operatively linked to a transcriptional regulatory sequence can be any prokaryotic or eukaryotic cell. Transforming or transfecting the vector into host cells, either eukaryotic (e.g., yeast, avian, insect or mammalian) or prokaryotic (e.g., bacterial cells) are standard procedures used widely in the microbial or tissue-culture technologies.

Vectors suitable for cultivation of the subject polynucleotides in bacterial cells (e.g., *E. coli*), include, but are not limited to, plasmids of the types: pBR322-derived plasmids, pEMBL-derived plasmids, pEX-derived plasmids, pBTac-derived plasmids, and pUC-derived plasmids. For replication in yeast, cloning and expression vehicles useful for introducing genetic constructs in *S. cerevisiae* include, but are not limited to, the YEP24, YIP5, YEP51, pYES2 and YRP17 plasmids (See, e.g., Broach et al., 1993, in *Experimental Manipulation of Gene Expression*, ed. M. Inouye, Academic Press, p. 83). These vectors can replicate in *E. coli* due to the presence of the pBR322 ori, and in yeast due to the replication determinant of the yeast 2 µm circle plasmid. In addition, drug-resistant markers such as ampicillin can be used.

Similarly, preferred mammalian vectors for the polynucleotides of the invention comprise prokaryotic sequences to facilitate the propagation of the vector in bacteria. Such vectors, when transfected into mammalian cells, can be designed to integrate into the mammalian chromosome for long-term stability using a linked selectable marker gene. Alternatively, derivatives of viruses such as the bovine papillomavirus (BPV-1) or Epstein-Barr virus can be used for transient expression. The various methods employed in the preparation of plasmid transformation of host organisms are well known in the art. For other suitable vector systems, as well as general recombinant procedures, see Sambrook et al., supra.

The term "vector" as explained above may also concern a polynucleotide construct comprising "naked" DNA.

5.3.2 Gene Therapy

Gene therapy approaches can be used in accordance with the present invention to prevent or treat cancer. Gene therapy refers to therapy performed by the administration to a subject of an expressed or expressible nucleic acid.

Any of the methods for gene therapy available in the art can be used in accordance with the present invention (See, e.g., Goldspiel et al., 1993, Clinical Pharmacy 12:488–505; Grossman and Wilson, 1993, Curr Opin Genet Devel. 3:110–114; Salmons and Gunzberg, 1993, Human Gene Therapy 4:129–141; Morgan and Anderson, 1993, Ann. Rev. Biochem. 62:191–217; Mulligan, 1993, Science 260:926–932; Tolstoshev, 1993, Ann. Rev. Pharmacol. Toxicol. 32:573–596; and Clowes et al., 1994, J. Clin. Invest. 93:644–651; Kiem et al., 1994, Blood 83:1467–1473, each of which is incorporated herein by reference).

Long-term effective use of a gene therapy vector to ameliorate disease in large mammals has been demonstrated. For example, administration of an adeno-associated virus ("AAV") containing a wild-type gene to dogs suffering from Leber congenital amaurosis, a condition that results in blindness due to a mutation of a gene (RPE65) in the retinal pigment epithelium, has successfully corrected the genetic defect (Ackland et al., 2001, Nature Genetics 28:92). Expression of the wild-type RPE65 gene was confirmed by RT PCR. Furthermore, restoration of function was demonstrated by electrophysiological studies of the retina, as well as by unbiased observations of the treated animals. The treatment was shown to be effective for at least four months.

Treatment of dogs suffering from hemophilia by intramuscular administration of AAV has also been reported (Herzog et al., 1999, Nature Medicine 5:56). Administration of an AAV encoding factor IX was shown to significantly reduce clotting time in treated dogs for 17 months. Thus, such examples demonstrate that gene therapy can be used to restore lost genetic function in a large animal model using treatment methods known in the art.

Several studies have demonstrated the usefulness of gene therapy in treating diseases in humans. In particular, a combination of gene therapy and chemotherapy can be successfully used to treat head and neck cancer. In a trial involving patients with recurrent head and neck cancer, ONYX-015, a replication-selective adenovirus, was used to deliver therapeutic genes to sites of recurrent cancer (Khuri et al., 2000, Nat Med. 6:862–3). ONYX-015 was administered in combination with the chemotherapeutic agents, cisplatin and 5-fluorouracil. Administration of ONYX-015 was by intratumoral injection. In 19 of 30 patients, the tumors shrank by 50%. In eight of these patients, the tumors disappeared altogether. By six months, none of the responding tumors had progressed, whereas all non-injected tumors treated with chemotherapy alone had progressed. Tumor biopsies obtained after treatment showed tumor-selective viral replication and necrosis induction. Other studies of ONYX-015 on recurrent head and neck cancer have demonstrated similar results (Nemunaitis et al., J. Clin. Oncol., 2001, 19:289–298; Lamont et al., Ann. Surg. Oncol., 2000, 7:588–592).

Gene therapy has also proven useful in treatment of a complication of diabetes. A phase III study comparing intramuscular delivery of ANG1 (a Vascular Endothelial Growth Factor gene containing plasmid) with placebo in diabetic patients with critical limb ischemia was carried out on thirteen patients. A total dose of 4000 ug ANG1 was administered into the femoral and calf muscles of the ischemic limb. After the follow-up period of 100 days, of six of thirteen patients improved. Ischemic ulcers improved in three patients, pain regressed in two patients, and hemodynamic improvement was significant in three patients (Kusumanto et al., Molecular Therapy 3:S73).

Gene therapy has also been used to treat an inherited disorder of the X-chromosome. Two infants with severe combined immunodeficiency (SCID) were treated with gene therapy. The treatment provided a normal copy of the defective gene that causes SCID (Cavazzana-Calvo et al., 2000, Science 288:669–672). The gene encodes a gamma c cytokine receptor subunit of interleukin-2, -4, -7, -9, and -15 receptors that signal the parents of T and NK cells to grow or spread. Bone marrow was harvested from the two patients. The stem cells were infected repeatedly for three days with a retrovirus carrying the replacement gene after which the bone marrow was restored to the patients. New cells with the correct version of the gene could be detected. Both children have cell counts comparable to those of normal children of the same age.

In another study, recombinant human adenovirus encoding p53 was administered, via the hepatic artery, to colorectal cancer patients with metastatic disease in the liver. Patients received injections in 1–3 monthly cycles. Transgene expression increased with dose and was detected more frequently in liver than in tumor specimens. Laser scanning cytometry detected apoptosis in tumor, but not normal tissues. Therefore, in humans, systemic vector delivery has successfully resulted in transgene expression in normal and malignant tissues (Atencio et al., 2001, Molecular Therapy 3:S309). One of skill in the art can appreciate use of the vectors of the invention, and variants of such vectors, for administration in humans to treat the variety of disorders described herein. Moreover, the skilled artisan can appreciate means of administration and expression of the vectors of the invention via multiple modes of administration including, without limitation, by systemic delivery (e.g., via the bloodstream).

Accordingly, gene therapy approaches using the vectors of the invention, which comprise a heterologous polynucleotide operatively linked to a transcriptional regulatory sequence, can be used to prevent or treat cancer and hyperproliferative diseases. For gene therapy purposes, vectors of the invention (comprising expression gene constructs) can be administered in any biologically effective carrier, e.g., any formulation or composition capable of effectively delivering the recombinant gene to cells in vivo. Gene constructs of the invention, comprising a polynucleotide of interest, can be inserted into a viral vector, such as, but not limited to, a retrovirus, adenovirus, adeno-associated virus, or herpes simplex virus-1, or can be inserted into a bacterial plasmid or eukaryotic plasmid, or maybe administered as naked DNA.

Viral vectors can be used to transfect cells directly. Plasmid DNA can be delivered into a cell with the help of, for example, cationic polymers, cationic liposomes (e.g., lipofectin, cholesterol derivatives such as D.D.A.B., cationic phospholipids), polylysine conjugates, gramicidin S, artificial viral envelopes or other such intracellular carriers. Alternatively, plasmid DNA can be derivatized (e.g., antibody conjugated). Plasmid DNA can also be administered by direct injection of the naked gene construct, by electroporation, or by calcium phosphate ("$CaPO_4$") precipitation carried out in vivo. Gene transfer and expression systems for treating cancer have been reported (See, e.g., Cooper et al., 1997, "Safety-modified episomal vectors for human gene therapy", Proc Natl Acad Sci. 94:6450–6455; Cooper, 1996, "Noninfectious gene transfer and expression systems for cancer gene therapy", Semin Oncol. 23:172–187).

It will be appreciated by the skilled artisan that because transduction of appropriate target cells represents an important first step in gene therapy, choice of the particular gene delivery system will depend on such factors as the phenotype of the intended target and the route of administration, e.g., locally or systemically. Furthermore, it will be recognized that gene constructs for transduction of expression constructs in vivo are also useful for in vitro transduction of cells, such as for use in the ex vivo tissue culture systems described herein.

A preferred approach for in vivo introduction of nucleic acid into a cell is by use of a viral vector comprising a polynucleotide of interest. In a preferred embodiment, the vector comprises an H19 transcriptional regulatory sequence operatively linked to a heterologous polynucleotide comprising sequences that encode a cytotoxic product, such that expression of the heterologous polynucleotide is under the control of the H19 transcriptional regulatory sequence.

Alternatively, the vector can comprise an H19 transcriptional regulatory sequence operatively linked to a heterologous polynucleotide comprising sequences that encode a gene product essential for viral replication or that can enhance viral replication.

Accordingly, in another embodiment, introduction of nucleic acid into a cell is achieved by using a replicative virus, such that expression of a gene required for viral replication is under the control of the H19 transcriptional regulatory sequence. In a specific embodiment, activation of the H19 transcriptional regulatory sequence induces expression of a product which is essential for viral replication, and causes lysis of the cell.

Use of a heterologous polynucleotide that encodes a cytotoxic, cytostatic, or replication-promoting products can be particularly advantageous because a high expression of the product is unnecessary to demonstrate an amelioration effect. For example, minute expression of a potent cytotoxic agent or of a product that enables viral replication (and concomitant lysis) can be sufficient to reduce tumor cell growth and can demonstrate clinically relevant improvement.

Viral vectors can be used for gene therapy approaches in accordance with the invention. Infection of cells with a viral vector has the advantage that a large proportion of the targeted cells can receive the polynucleotide of interest. Additionally, molecules encoded within the viral vector, e.g., by a heterologous cDNA contained in the viral vector, are expressed efficiently in cells that have taken up viral vector.

Suitable vectors that can be delivered using the presently disclosed methods and compositions include, but are not limited to, herpes simplex virus vectors, adenovirus vectors, adeno-associated virus vectors, retroviral vectors, pseudorabies virus vectors, and alpha-herpes virus vectors. A thorough review of viral vectors, particularly viral vectors suitable for modifying nonreplicating cells, and how to use such vectors to express a polynucleotide of interest can be found in *Viral Vectors: Gene Therapy and Neuroscience Applications*, Caplitt and Loewy (eds.), Academic Press, San Diego (1995).

The infection spectrum of viruses (and viral-based vectors) can be limited by modifying the viral packaging proteins on the surface of the viral particle (See, e.g., PCT publications WO93/25234 and WO94/06920). Strategies for modifying the infection spectrum of retroviral vectors include, but are not limited to, coupling antibodies specific for cell surface antigens to the viral env protein (Roux et al., 1989, Proc. Nat. Acad. Sci. USA 86:9079–9083; Julan et al., 1992, J. Gen. Virol. u3:3251–3255; Goud et al., 1983, Virology 163:251–254) or coupling cell surface receptor ligands to the viral env proteins (Neda et al., 1991, J. Biol. Chem 266:14143–14146). Coupling can be in the form of chemical crosslinking with a protein or other compound (e.g., lactose to convert the env protein to an asialogycoprotein), or in the form of fusion proteins (e.g., single-chain antibody/env fusion proteins). Accordingly, cancer cells can be targeted to the surface of a recombinant virus by using, for example, coupling antibodies that are directed against tumor-associated molecules, or by using cancer cell surface proteins. Such techniques, while useful for limiting, or otherwise directing, the infection to certain tissue types, can also be used to convert an ectotropic vector into an amphotropic vector.

A preferred viral gene delivery system useful in the present invention utilizes adenovirus-derived vectors. The genome of an adenovirus can be manipulated such that it encodes and expresses a gene product of interest, but is inactivated in terms of its ability to replicate in a normal lytic viral life cycle (See, e.g., Berkner et al., 1988, BioTechniques 6:616; Rosenfeld et al., 1991, Science 252:431–434; Rosenfeld et al., 1992, Cell 68:143–155). Suitable adenoviral vectors derived from the adenovirus strain AD type 5 d1324 or other strains of adenovirus (e.g., Ad2, Ad3, Ad7, etc.), are well known to those skilled in the art.

Recombinant adenoviruses can be advantageous in certain circumstances in that they can be used to infect a wide variety of cell types, including airway epithelium (Rosenfeld et al., 1992, Cell 68:143–155), endothelial cells (Lemarchand et al., 1992, Proc Natl Acad Sci. 89:6482–6486), hepatocytes (Herz and Gerard, 1993, Proc Natl Acad Sci. 90:2812–2816), and muscle cells (Quantin et al., 1992, Proc Natl Acad Sci. 89:2581–2584). Furthermore, the virus particle is relatively stable, amenable to purification and concentration, and can be modified so as to affect the spectrum of infectivity.

Additionally, introduced adenoviral DNA (and foreign DNA contained therein) is generally not integrated into the genome of a host cell but remains episomal, thereby avoiding potential problems (e.g., insertional mutagenesis) that can occur when introduced DNA (e.g., retroviral DNA) becomes integrated into the host genome.

Moreover, the carrying capacity of the adenoviral genome for foreign DNA is large (up to 8 kilobases) relative to other gene delivery vectors (Berkner et al., 1988, BioTechniques 6:616; Haj-Ahmand and Graham, 1986, J. Virol. 57:267). Preferably, a replication-defective adenoviral vector useful for the methods of the invention have all or part of the viral E1 and E3 genes deleted, but retain as much as 80% of the adenoviral genetic material (See, e.g., Jones et al., 1979, Cell 16:683; Berkner et al., supra; Graham et al. in *Methods in Molecular Biology*, Vol.7, E. J. Murray (ed.), Humana, Clifton N.J. (1991) pp. 109–127).

Adeno-associated virus ("AAV") can also be used in accordance with the gene therapy approaches of the present invention (See, e.g., Walsh et al., 1993, Proc. Soc. Exp. Biol. Med. 204:289–300; U.S. Pat. No. 5,436,146). Adeno-associated virus is a naturally occurring defective virus that requires another virus, such as an adenovirus or a herpes virus, as a helper virus for efficient replication and a productive life cycle (See, e.g., Muzyczka et al., 1992, "Use of adeno-associated virus as a general transduction vector for mammalian cells", Curr Top Microbiol Immunol. 158:97–129). Also, AAV is one of the few viruses that can integrate its DNA into non-dividing cells, and exhibits a high frequency of stable integration (See, e.g., Flotte et al., 1992, Am J Respir Cell Mol Biol. 7:349–354; Samulski et al., 1989, J. Virol. 63:3822–3828; McLaughlin et al., 1989, J. Virol. 63:1963–1973).

Vectors containing as few as 300 base pairs of AAV can be packaged and can integrate. Space for the insertion of exogenous DNA is limited to about 4.5 kb. An AAV vector such as that described in Tratschin et al. (1985, Mol. Cell. Biol. 5:3251–3260) can be used to introduce DNA into cells. A variety of nucleic acids have been introduced into different cell types using AAV vectors (See, e.g. Hermonat et al., 1984, Proc Natl Acad Sci. 81:6466–6470; Tratschin et al., 1985, Mol. Cell. Biol. 4:2072–2081; Wondisford et al., 1988, Mol. Endocrinol. 2:32–39; Tratschin et al., 1984, J. Virol. 51:611–619; Flotte et al., 1993, J. Biol. Chem. 268: 3781–3790).

Preferred targets for adenovirus-based delivery systems are the liver, central nervous system, endothelial cells, respiratory epithelia, and muscle cells. Moreover, adenoviruses are able to infect non-dividing cells (See, e.g., Rosenfeld et al., 1991, Science 252:431–434; Rosenfeld et al., 1992, Cell 68:143–155; Mastrangeli et al., 1993, J. Clin. Invest. 91:225–234; Kozarsky and Wilson, 1993, Curr. Opin. Genetics Develop. 3:499–503; Bout et al., 1994, Human Gene Therapy 5:3–10; PCT Publication No. WO 94/12649; and Wang et al., 1995, Gene Therapy 2:775–783).

An effective amount of a vector of the invention can be administered to a tumor by a plurality of modes. For example, vectors in liposomes have been administered systemically for the treatment of lung cancers (Ramesh et al., 2001, Molecular Therapy, 3: 337–350). Adenovirus vectors containing tumor-suppressor genes have been administered intravesically for the treatment of bladder cancer (Pagliaro, 2000, World J. Urol, 18: 148–151). Another clinical study reported the intravenous administration of a herpes vector for treating bladder cancer (Oyama et al., 2000, Human Gene Therapy 11:1683–1693). The Fourth-Annual Meeting of the American Society of Gene Therapy (Molecular Therapy, 3(5) 2001, Academic Press) reported several successful gene therapy trials involving the intra-arterial administration of adenovirus for treating colorectal tumors (Atencio et al. ibid. Abstract No. 871), intramuscular delivery for treating diabetes (Kusumanto et al. ibid. Abstract No. 205), and systematic delivery of an IL-2-based plasmid for treating lung tumors (Sayre et al. ibid. Abstract No. 1095).

The recipient subject's cells can be engineered to express one or more of the vectors of the invention, or combinations of vectors of the invention, or combinations of vectors of the invention with another therapeutic agent. Accordingly, in one embodiment, a target cell in a subject expresses a cytotoxic gene product, a cytostatic gene product, and/or a gene product involved in viral regulation.

Gene therapy involves introducing a gene construct to cells. Accordingly, the vectors of the invention can be delivered in vivo or ex vivo to target cells. A variety of techniques are known in the art for introducing vectors (included in this definition is "naked" DNA constructs) in vitro into cells including, but not limited to, calcium phosphate-DNA precipitation, DEAE-Dextran transfection, electroporation, microinjection, infection with a recombinant viral or bacteriophage vector, liposome-mediated DNA transfer, cell fusion, chromosome-mediated gene transfer, microcell-mediated gene transfer, and spheroplast fusion (See, e.g., Maniatis et al., 1989; Current Protocols, 2000; Loeffler and Behr, 1993, Meth. Enzymol. 217:599–618; Cohen et al., 1993, Meth. Enzymol. 217:618–644; Cline, 1985, Pharmacol. Ther. 29:69–92 Bell et al., 1983, Nature 304: 5924).

Alternatively, one can use gene therapy to transfect a recipient's cells in vivo. In a specific embodiment, a vector of the invention is administered directly in vivo, where the cloned polynucleotide of interest is expressed, and optionally expresses the encoded protein (e.g., a cytotoxic or cytostatic polypeptide). Such vectors can be internalized by using, for example, a defective or attenuated retroviral vector or other viral vectors that can infect mammalian cells (See, e.g., U.S. Pat. No. 4,980,286).

Methods of administering vectors that transfect cells in vivo are known in the art (See, e.g., Sayre et al., 2001, Mol Ther. 3(5):S384; Atencio et al., 2001, Mol Ther. 3(5):S309). Formulations of nucleic acid for such in vivo methods can include, but are not limited to, naked DNA, nucleic acid encapsulated into liposomes or liposomes combined with viral envelope receptor proteins (Nicolau et al., 1983, Proc Natl Acad Sci. 80:1068), DNA coupled to a polylysine-glycoprotein carrier complex, and nucleic acid precipitants.

A vector of the invention can be delivered in vivo (i.e., directly into a subject). Accordingly, in one embodiment, a vector of the invention is injected directly into the target tissue or cell derivation site. In another embodiment, a vector of the invention can be introduced into the target tissue as an implant such as, for example, in a polymer formulation (See, e.g., U.S. Pat. No. 5,702,717). In another embodiment, a vector of the invention is targeted to the desired cells or tissues.

In a particular embodiment, a vector is introduced in vivo such that it is taken up by a cell and directs the transcription of a cytotoxic agent, cytostatic agent, or an agent that stimulates a cytotoxic or cytostatic response (e.g., cell cycle arrest, apoptosis). Such a vector can remain episomal or can become chromosomally integrated. Vectors can be plasmid or viral (or others known in the art) that can be used to replicate and/or express a cloned polynucleotide of interest. Alternatively, "naked" DNA constructs can be administered in vivo. In a specific embodiment, the polynucleotide encodes a cytotoxic, cytostatic agent, or an agent that stimulates a cytotoxic or cytostatic response. In a further embodiment, the polynucleotide is expressed in a target mammalian cell.

A variety of expression vectors useful for the methods of the invention are known in the art (e.g., pCI, pVPack, pCMV, pSG5). Vectors that can be introduced into target cells and/or tissues of a subject include, but are not limited to, adenovirus, adeno-associated virus ("AAV"), retrovirus, and herpes virus vectors, as well as other particles that introduce DNA into cells, such as liposomes.

In addition to viral transfer methods, such as those illustrated above, non-viral methods can also be employed to cause directed expression of a desired heterologous polynucleotide in the tissue of an animal. Most nonviral methods of gene transfer rely on normal mechanisms used by mammalian cells for the uptake and intracellular transport of macromolecules. In preferred embodiments, non-viral gene delivery systems used in the methods of the present invention rely on endocytic pathways for the uptake of a vector of the invention by the target cell. Exemplary gene delivery systems of this type include liposomal derived systems, poly-lysine conjugates, and artificial viral envelopes.

A polynucleotide of interest is preferably under the control of a tumor-specific promoter of the invention. In certain instances, use of a tissue-specific promoter (See, e.g., U.S. Pat. No. 6,241,982 to Barber et al.) in combination with a regulatory sequence of the invention can provide further therapeutic benefit.

Nucleic acid preparations can be introduced in vivo using any one of the techniques known in the art such as direct injection, infusion, implantation, electroporation, and particle bombardment. In addition, "gene guns" have been used for gene delivery into cells (Australian Pat. No. 9068389).

Synthetic genes, the transcription and translation of which results in the production of a gene product (e.g., RNA or polypeptide) that interferes with the function, growth, and/or division (e.g., cytotoxic agent, cytostatic agent, agent that stimulates a cytotoxic or cytostatic response), can be constructed using techniques well known in the art (See, e.g., Ausubel et al., 1990, Current Protocols in Molecular Biology p. 8.2.8 to 8.2.13; Ausubel et al., 1995, Short Protocols in Molecular Biology p. 8.8–8.9, John Wiley & Sons Inc.).

An endogenous protein involved in cell division or cell viability (e.g., bcl-2, abl, bax) can be targeted by gene therapy using, for example, antisense, ribozyme, triple helix molecules, and/or recombinant antibodies resulting in a decrease in the respective gene expression and/or protein levels. In accordance with the compositions and methods of the invention, a cytotoxic or cytostatic gene product is intended to encompass RNA, cDNA, as well as polypeptides. Techniques for the production and use of antisense, ribozyme, and/or triple helix molecules are known to those of ordinary skill in the art.

The vector of the invention can be injected directly into a target tissue as naked DNA. In another embodiment, a vector of the invention can be introduced intracellularly using microparticle bombardment, for example, by using a Biolistic gene gun (DuPont). In another embodiment, a vector of the invention can be coated with lipids, or cell-surface receptors, or transfecting agents, such that encapsulation in liposomes, microparticles, or microcapsules facilitates access to target tissues and/or entry into target cells. In yet another embodiment, a vector of the invention is linked to a polypeptide that is internalized in a subset of cells or is targeted to a particular cellular compartment and thus ensure specificity of expression by means of selective delivery and selective expression in target cells. In a further embodiment, the linked polypeptide is a nuclear targeting sequence that targets the vector to the cell nucleus. In another further embodiment, the linked polypeptide is a ligand that is internalized by receptor-mediated endocytosis in cells expressing the respective receptor for the ligand (See, e.g., Wu and Wu, 1987, J. Biol. Chem. 262:4429–4432).

In another embodiment, vector-ligand complexes can be formed such that the ligand comprises a fusogenic viral peptide, which disrupts endosomes, thereby allowing the nucleic acid to avoid lysosomal degradation. In another embodiment, a vector of the invention can be targeted in vivo via a cell-specific receptor resulting in cell-specific uptake and expression (See, e.g., International Patent Publications WO 92/06180, WO 92/22635, WO 92/20316, and WO 93/14188). In yet another embodiment, a vector of the invention is introduced intracellularly and, by homologous recombination, can transiently or stably incorporate within the host cell DNA, which then allows for its expression, (Koller and Smithies, 1989, Proc Natl Acad Sci. 86:8932–8935; Zijlstra et al., 1989, Nature 342:435–438).

In one embodiment, viral vectors are used that contain nucleic acids encoding compounds that activate cytokine receptors (i.e., cytokines or antibodies), or compounds that activate molecules expressed on activated immune cells (See, e.g., Miller et al., 1993, Meth. Enzymol. 217:581–599). In a specific embodiment, a viral vector that contains nucleic acid sequences encoding 4–1BB ligand, or anti-4–1BB immunoglobulin, and/or IL-12 are used. For example, a retroviral vector can be used in which sequences not necessary for packaging of the viral genome and integration into host cell DNA have been deleted, and nucleic acid sequences encoding 4-1BB ligand, or anti-4-1BB immunoglobulin, or IL-12 are cloned into the vector, thereby facilitating delivery of the transgene into a subject. (See, e.g., Boesen et al., 1994, Biotherapy 6:291–302, which describes the use of a retroviral vector to deliver the mdr1 gene to hematopoietic stem cells).

The vector of the invention can include appended groups such as peptides (e.g., for targeting host cell receptors in vivo), or agents for facilitating transport across the cell membrane (See, e.g., Letsinger et al., 1989, Proc Natl Acad Sci. 86:6553–6556; Lemaitre et al., 1987, Proc Natl Acad Sci. 84:648–652; PCT Publication No. WO 88/09810), or across the blood-brain barrier (See, e.g., PCT Publication No. WO 89/10134).

In one embodiment, sequence diversity can be introduced (e.g., by mutagenesis) into a transcriptional regulatory sequence useful for the methods and compositions of the invention. In another embodiment, sequence diversity can be introduced into the heterologous polynucleotide of interest (e.g., a polynucleotide encoding a cytotoxic or cytostatic agent) which is operatively linked to the transcriptional regulatory sequence. Use of automated gene synthesis techniques, for example, provides an opportunity for generating sequence variants. The skilled artisan can appreciate that polynucleotides coding for variants can be generated by substitution of codons for those represented in the naturally occurring polynucleotide sequences. In addition, polynucleotides coding for synthetic variants can be generated which incorporate from 1 to 5, 5 to 10, or 10 to 20 amino acid substitutions, or deletions or additions. In addition, synthetic variants can be generated by introducing domains from heterologous polypeptides.

In a clinical setting, the delivery of a therapeutic vector into a subject can be achieved by several different methods known in the art. For instance, a pharmaceutical preparation comprising a vector of the invention can be introduced systemically, e.g., by intravenous injection. Specific expression of the heterologous polynucleotide in target cells occurs predominantly from the specificity of expression provided by cell-type expression due to the transcriptional regulatory sequences controlling expression of the heterologous polynucleotide. Additional specificity measures confers greater patient safety due to, for example, the delivery vector's targeting of specific cell types, or the use of cancer-specific transcriptional regulatory sequences in combination with a vector that targets particular cell types. In other embodiments, initial delivery of the vector is more limited with introduction into the animal being quite localized. For example, the vector can be introduced by catheter (See, e.g., U.S. Pat. No. 5,328,470) to any lumen of the body (e.g., bladder), or by stereotactic injection (See, e.g., Chen et al., 1994, Proc Natl Acad Sci. 91:3054–3057). A vector of the invention can also be delivered to target cells or tissues by electroporation using techniques known in the art (See, e.g., Dev et al., 1994, Cancer Treat. Rev. 20:105–115). Modes of administration useful for methods of the invention are described more fully below.

A pharmaceutical preparation can comprise a vector of the invention in a pharmaceutically acceptable carrier, an acceptable diluent, or a slow-release matrix in which the vector is embedded. Additionally, where the vector can be produced intact from recombinant cells (e.g., retroviral vector), the pharmaceutical preparation can comprise one or more cells producing the vector. Pharmaceutical compositions of the invention are disclosed more fully below.

5.4 Therapeutic Endpoints and Dosages

One of ordinary skill will appreciate that, from a medical practitioner's or subject's perspective, virtually any alleviation or prevention of an undesirable symptom associated with a hyperproliferative or cancerous condition (e.g., pain, sensitivity, weight loss, and the like) would be desirable. Additionally, any reduction in tumor mass or growth rate is desirable, as is an improvement in the histopathological picture of the tumor. Thus, for the purposes of this Application, the terms "treatment", "therapeutic use", or "medicinal use" used herein shall refer to any and all uses of the claimed compositions which remedy a disease state or disease symptoms, or otherwise prevent, hinder, retard, or reverse the progression of disease, or other undesirable symptoms in any way whatsoever.

An effective dosage and treatment protocol can be determined by routine and conventional means, starting with a low dose in laboratory animals and then increasing the dosage while monitoring the effects, and systematically varying the dosage regimen as well. Animal studies, preferably mammalian studies, are commonly used to determine the maximal tolerable dose ("MTD") of bioactive agent per kilogram weight. Those skilled in the art regularly extrapolate doses for efficacy, while avoiding toxicity, in other species, including humans.

Before human studies of efficacy are undertaken, Phase I clinical studies in normal subjects help establish safe doses. Numerous factors may be taken into consideration by a clinician when determining an optimal dosage for a given subject. Primary among these is the toxicity and half-life of the chosen heterologous gene product. Additional factors include the size of the subject, the age of the subject, the general condition of the subject, the particular disease being treated, the severity of the disease, the presence of other drugs in the subject, the in vivo activity of the gene product, and the like. The trial dosages would be chosen after consideration of the results of animal studies and the clinical literature.

For example, a typical human dose of an adenoviral vector containing an H19 transcriptional regulatory sequence operatively linked to a heterologous polynucleotide encoding a cytotoxic agent such as thymidine kinase is from $1 \times 10^7$ pfu to $1 \times 10^{10}$ pfu injected directly into the tumor mass per day. More preferably, the daily dose of such an adenoviral vector injected directly into a tumor would be from $1 \times 10^8$ pfu to $1 \times 10^{10}$ pfu, depending upon the tumor size. For an adenoviral vector comprising a heterologous polynucleotide encoding a cytotoxic product operatively linked to a transcriptional regulatory sequence, wherein the cytotoxic product has a different level of toxicity, these values would of course be altered accordingly. Similar doses of an adenoviral vector containing an IGF-2 P4 promoter operatively linked to a heterologous polynucleotide encoding a cytotoxic agent such as thymidine kinase can also be used as a suggested starting point.

Particularly where in vivo use is contemplated, the various biochemical components of the present invention are preferably of high purity and are substantially free of potentially harmful contaminants (e.g., at least National Food (NF) grade, generally at least analytical grade, and preferably at least pharmaceutical grade). To the extent that a given compound must be synthesized prior to use, such synthesis or subsequent purification shall preferably result in a product substantially free of any potentially toxic agents that may have been used during the synthesis or purification procedures.

A "low dose" or "reduced dose" refers to a dose that is below the normally administered range, i.e., below the standard dose as suggested by the *Physicians' Desk Reference*, 54$^{th}$ *Edition* (2000) or a similar reference. Such a dose can be sufficient to inhibit cell proliferation, or demonstrates ameliorative effects in a human, or demonstrates efficacy with fewer side effects as compared to standard cancer treatments. Normal dose ranges used for particular therapeutic agents and standard cancer treatments employed for specific diseases can be found in the *Physicians' Desk Reference.* 54$^{th}$ *Edition* (2000) or in *Cancer: Principles & Practice of Oncology*, DeVita, Jr., Hellman, and Rosenberg (eds.) 2nd edition, Philadelphia, Pa.: J. B. Lippincott Co., 1985.

Reduced doses of a vector of the invention and/or combination therapeutic can demonstrate reduced toxicity, such that fewer side effects and toxicities are observed in connection with administering a vector of the invention and one or more cancer therapeutics for shorter duration and/or at lower dosages when compared to other treatment protocols and dosage formulations, including the standard treatment protocols and dosage formulations as described in the *Physicians' Desk Reference.* 54$^{th}$ *Edition* (2000) or in *Cancer: Principles & Practice of Oncology*, DeVita, Jr., Hellman, and Rosenberg (eds.) 2nd edition, Philadelphia, Pa.: J. B. Lippincott Co., 1985.

Other factors to be considered in determining an effective dose of a vector of the invention include whether the vector will be administered in combination with other therapeutics. In such cases, the relative toxicity of the other therapeutics may indicate the use of the vector at low doses. Alternatively, treatment with a high dose of the vector can result in combination therapies with reduced doses of therapeutics. For example, treatment of a subject with a vector of the invention can further increase the sensitivity of a subject to other cancer therapeutics. In a specific embodiment, treatment with a particularly high dose of the vector can result in combination therapies with greatly reduced doses of cancer therapeutics. In such cases, the particularly high dose of the vector is combined with, for example, a greatly shortened radiation therapy schedule. In another example, the particularly high dose of the vector produces significant enhancement of the potency of other cancer therapeutic agents.

Additionally, particularly high doses of a vector of the invention can further shorten the period of administration of a therapeutically effective amount of the vector and/or additional therapeutic, such that the length of a treatment cycle is much shorter than that of the standard treatment.

5.5 Combination Therapy

The administration of a vector of the invention can potentiate the effect of a cancer therapeutic agent. Accordingly, in a preferred embodiment, the invention further encompasses the use of combination therapy to prevent or treat cancer.

Accordingly, the present invention relates to a method for treating or preventing cancer, comprising administering to a subject in need thereof an effective amount of a vector comprising a heterologous polynucleotide operably linked to one or more regulatory sequences useful for the methods of the invention, together with another therapeutic agent. The other therapeutic agent can be administered prior to, concurrently with (or overlapping with), or subsequent to administration of the vector. In one preferred embodiment, the regulatory sequence is derived from an H19, IGF-1, IGF-2 P3 or IGF-2 P4 promoter sequence.

The present invention also relates to a method for treating or preventing cancer, comprising administering to a subject in need thereof an effective amount of a replicative virus, wherein the replicative virus comprises a polynucleotide, which comprises a sequence encoding a product important for viral replication, operably linked to one or more regulatory sequences useful for the methods of the invention, together with another therapeutic agent. The other therapeutic agent can be administered prior to, concurrently with (or overlapping with), or subsequent to administration of the replicative virus. In one preferred embodiment, the regulatory sequence is derived from an H19, IGF-1, IGF-2 P3 or IGF-2 P4 promoter sequence. In a further embodiment, the replicative virus is administered in combination with an effective amount of a vector comprising a heterologous polynucleotide operably linked to one or more regulatory sequences, wherein the heterologous polynucleotide encodes a cytotoxic or cytostatic product, and wherein the regulatory sequence causes expression of the heterologous polynucleotide in cancer cells.

Combination therapies contemplated by the invention can be used to prevent cancer, prevent the recurrence of cancer, or prevent the spread or metastasis or cancer. Combination therapies can also diminish established cancer or ameliorate at least one manifestation or side effect of cancer. As such, combination therapy refers to the administration of a vector of the invention and one or more compounds or treatments that aid in the prevention or treatment of cancer, which compounds or treatments include, but is not limited to, chemoagents, immunotherapeutics, cancer vaccines, antiangiogenic agents, cytokines, hormone therapies, other gene therapies, and radiotherapies.

In one embodiment, one or more chemoagents, in addition to a vector of the invention, is administered to treat a cancer patient. A chemoagent (or "anti-cancer agent" or "anti-tumor agent" or "cancer therapeutic") refers to any molecule or compound that assists in the treatment of tumors or cancer. Examples of chemoagents contemplated by the present invention include, but are not limited to, ganciclovir, cytosine arabinoside, taxoids (e.g., paclitaxel, docetaxel), anti-tubulin agents (e.g., paclitaxel, docetaxel, epothilone B, or its analogues), macrolides (e.g., rhizoxin ) cisplatin, carboplatin, adriamycin, tenoposide, mitozantron, discodermolide, eleutherobine, 2-chlorodeoxyadenosine, alkylating agents (e.g., cyclophosphamide, mechlorethamine, thioepa, chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP) cisplatin, thiotepa), antibiotics (e.g., dactinomycin (formerly actinomycin), bleomycin, mithramycin, anthramycin), antimetabolites (e.g., methotrexate, 6-mercaptopurine, 6-thioguanine, cytarabine, flavopiridol, 5-fluorouracil, fludarabine, gemcitabine, dacarbazine, temozolamide), asparaginase, Bacillus Calmette and Guerin, diphtheria toxin, hexamethylmelamine, hydroxyurea, LYSODREN®, nucleoside analogues, plant alkaloids (e.g., Taxol, paclitaxel, camptothecin, topotecan, irinotecan (CAMPTOSAR, CPT-11), vincristine, vinca alkyloids such as vinblastine), podophyllotoxin (including derivatives such as epipodophyllotoxin, VP-16 (etoposide), VM-26 (teniposide)), cytochalasin B, colchine, gramicidin D, ethidium bromide, emetine, mitomycin, procarbazine, mechlorethamine, anthracyclines (e.g., daunorubicin (formerly daunomycin), doxorubicin, doxorubicin liposomal), dihydroxyanthracindione, mitoxantrone, mithramycin, actinomycin D, procaine, tetracaine, lidocaine, propranolol, puromycin, anti-mitotic agents, abrin, ricin A, pseudomonas exotoxin, nerve growth factor, platelet derived growth factor, tissue plasminogen activator, aldesleukin, allutamine, anastrozle, bicalutamide, biaomycin, busulfan, capecitabine, carboplain, chlorabusil, cladribine, cylarabine, daclinomycin, estramusine, floxuridhe, gamcitabine, gosereine, idarubicin, itosfamide, lauprolide acetate, levamisole, lomusline, mechlorethamine, magestrol, acetate, mercaptopurino, mesna, mitolanc, pegaspergase, pentoslatin, picamycin, riuxlmab, campath-1, straplozocin, thioguanine, tretinoin, vinorelbine, or any fragments, family members, or derivatives thereof, including pharmaceutically acceptable salts thereof. Compositions comprising one or more chemoagents (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone.

In one embodiment, said chemoagent is gemcitabine at a dose ranging from 100 to 1000 mg/m$^2$/cycle. In one embodiment, said chemoagent is dacarbazine at a dose ranging from 200 to 4000 mg/m$^2$/cycle. In a preferred embodiment, said dose ranges from 700 to 1000 mg/m$^2$/cycle. In another embodiment, said chemoagent is fludarabine at a dose ranging from 25 to 50 mg/m$^2$/cycle. In another embodiment, said chemoagent is cytosine arabinoside (Ara-C) at a dose ranging from 200 to 2000 mg/m$^2$/cycle. In another embodiment, said chemoagent is docetaxel at a dose ranging from 1.5 to 7.5 mg/kg/cycle. In another embodiment, said chemoagent is paclitaxel at a dose ranging from 5 to 15 mg/kg/cycle. In yet another embodiment, said chemoagent is cisplatin at a dose ranging from 5 to 20 mg/kg/cycle. In yet another embodiment, said chemoagent is 5-fluorouracil at a dose ranging from 5 to 20 mg/kg/cycle. In yet another embodiment, said chemoagent is doxorubicin at a dose ranging from 2 to 8 mg/kg/cycle. In yet another embodiment, said chemoagent is epipodophyllotoxin at a dose ranging from 40 to 160 mg/kg/cycle. In yet another embodiment, said chemoagent is cyclophosphamide at a dose ranging from 50 to 200 mg/kg/cycle. In yet another embodiment, said chemoagent is irinotecan at a dose ranging from 50 to 75, 75 to 100, 100 to 125, or 125 to 150 mg/m$^2$/cycle. In yet another embodiment, said chemoagent is vinblastine at a dose ranging from 3.7 to 5.4, 5.5 to 7.4, 7.5 to 11, or 11 to 18.5 mg/m$^2$/cycle. In yet another embodiment, said chemoagent is vincristine at a dose ranging from 0.7 to 1.4, or 1.5 to 2 mg/m$^2$/cycle. In yet another embodiment, said chemoagent is methotrexate at a dose ranging from 3.3 to 5, 5 to 10, 10 to 100, or 100 to 1000 mg/m$^2$/cycle.

In a preferred embodiment, the invention further encompasses the use of low doses of chemoagents when administered as part of a treatment regimen using a vector of the invention. For example, initial treatment with a vector of the invention increases the sensitivity of a tumor to subsequent challenge with a dose of chemoagent, which dose is near or below the lower range of dosages when the chemoagent is administered without a vector of the invention. In one embodiment, a vector of the invention and a low dose (e.g., 6 to 60 mg/m$^2$/day or less) of docetaxel are administered to a cancer patient. In another embodiment, a vector of the invention and a low dose (e.g., 10 to 135 mg/m$^2$/day or less) of paclitaxel are administered to a cancer patient. In yet another embodiment, a vector of the invention and a low dose (e.g., 2.5 to 25 mg/m$^2$/day or less) of fludarabine are administered to a cancer patient. In yet another embodiment, a vector of the invention and a low dose (e.g., 0.5 to 1.5 g/m$^2$/day or less) of cytosine arabinoside (Ara-C) are administered to a cancer patient.

The invention, therefore, contemplates the use of one or more vectors of the invention, which is administered prior to, subsequently, or concurrently with low doses of chemoagents, for the prevention or treatment of cancer.

In one embodiment, said chemoagent is gemcitabine at a dose ranging from 10 to 100 mg/m$^2$/cycle.

In one embodiment, said chemoagent is cisplatin, e.g., PLATINOL or PLATINOL-AQ (Bristol Myers), at a dose ranging from 5 to 10, 10 to 20, 20 to 40, or 40 to 75 mg/m$^2$/cycle. In another embodiment, a dose of cisplatin ranging from 7.5 to 75 mg/m$^2$/cycle is administered to a subject with ovarian cancer. In another embodiment, a dose of cisplatin ranging from 5 to 50 mg/m$^2$/cycle is administered to a subject with bladder cancer.

In another embodiment, said chemoagent is carboplatin, e.g., PARAPLATIN (Bristol Myers), at a dose ranging from 2 to 4, 4 to 8, 8 to 16, 16 to 35, or 35 to 75 mg/m$^2$/cycle. In another embodiment, a dose of carboplatin ranging from 7.5 to 75 mg/m$^2$/cycle is administered to a subject with ovarian cancer. In another embodiment, a dose of carboplatin ranging from 5 to 50 mg/m$^2$/cycle is administered to a subject with bladder cancer. In another embodiment, a dose of carboplatin ranging from 2 to 20 mg/m$^2$/cycle is administered to a subject with testicular cancer.

In another embodiment, said chemoagent is docetaxel, e.g., TAXOTERE (Rhone Poulenc Rorer) at a dose ranging from 6 to 10, 10 to 30, or 30 to 60 mg/m$^2$/cycle.

In another embodiment, said chemoagent is paclitaxel, e.g., TAXOL (Bristol Myers Squibb), at a dose ranging from 10 to 20, 20 to 40, 40 to 70, or 70 to 135 mg/kg/cycle.

In another embodiment, said chemoagent is 5-fluorouracil at a dose ranging from 0.5 to 5 mg/kg/cycle.

In another embodiment, said chemoagent is doxorubicin, e.g., ADRIAMYCIN (Pharmacia & Upjohn), DOXIL (Alza), RUBEX (Bristol Myers Squibb), at a dose ranging from 2 to 4, 4 to 8, 8 to 15, 15 to 30, or 30 to 60 mg/kg/cycle.

In one embodiment, breast cancer can be treated with a pharmaceutical composition comprising a vector of the invention in combination with 5-fluorouracil, cisplatin, docetaxel, doxorubicin, Herceptin®, gemcitabine (Seidman A D, 2001, "Gemcitabine as single-agent therapy in the management of advanced breast cancer", Oncology 15:11–14), IL-2, paclitaxel, and/or VP-16 (etoposide).

In another embodiment, prostate cancer can be treated with a pharmaceutical composition comprising a vector of the invention in combination with paclitaxel, docetaxel, mitoxantrone, and/or an androgen receptor antagonist (e.g., flutamide).

In another embodiment, leukemia can be treated with a pharmaceutical composition comprising a vector of the invention in combination with fludarabine, cytosine arabinoside, gemtuzumab (MYLOTARG), daunorubicin, methotrexate, vincristine, 6-mercaptopurine, idarubicin, mitoxantrone, etoposide, asparaginase, prednisone and/or cyclophosphamide.

As another example, myeloma can be treated with a pharmaceutical composition comprising a vector of the invention in combination with dexamethasone.

In another embodiment, melanoma can be treated with a pharmaceutical composition comprising a vector of the invention in combination with dacarbazine.

In another embodiment, colorectal cancer can be treated with a pharmaceutical composition comprising a vector of the invention in combination with irinotecan.

In another embodiment, bladder cancer can be treated with a pharmaceutical composition comprising a vector of the invention in combination with cisplatin, carboplatin, or Exisulind (APTOSYN) (Piazza et al., 2001, "Exisulind, a novel proapoptotic drug, inhibits rat urinary bladder tumorigenesis", Cancer Res 61:3961–3968).

In another embodiment, lung cancer can be treated with a pharmaceutical composition comprising a vector of the invention in combination with paclitaxel, docetaxel, etoposide and/or cisplatin.

In another embodiment, non-Hodgkin's lymphoma can be treated with a pharmaceutical composition comprising a vector of the invention in combination with cyclophosphamide, CHOP, etoposide, bleomycin, mitoxantrone and/or cisplatin.

In another embodiment, gastric cancer can be treated with a pharmaceutical composition comprising a vector of the invention in combination with cisplatin.

In another embodiment, pancreatic cancer can be treated with a pharmaceutical composition comprising a vector of the invention in combination with gemcitabine.

In another embodiment, a vector of the invention is administered in combination with one or more immunotherapeutic agents, such as antibodies and immunomodulators, which includes, but is not limited to, Herceptin®, Retuxan®, OvaRex, Panorex, BEC2, IMC-C225, Vitaxin, Campath I/H, Smart M195, LymphoCide, Smart I D10, and Oncolym, rituxan, rituximab, gemtuzumab, or trastuzumab.

In another embodiment, a vector of the invention is administered in combination with one or more anti-angiogenic agents, which includes, but is not limited to, angiostatin, thalidomide, kringle 5, endostatin, Serpin (Serine Protease Inhibitor) anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51:2077–2083), a 14-amino acid peptide corresponding to a fragment of collagen I (Tolma et al., 1993, J. Cell Biol. 122:497–511), a 19 amino acid peptide corresponding to a fragment of Thrombospondin I (Tolsma et al., 1993, J. Cell Biol. 122:497–511), a 20-amino acid peptide corresponding to a fragment of SPARC (Sage et al., 1995, J. Cell. Biochem. 57:1329–1334), or any family members, or variants thereof, including pharmaceutically acceptable salts thereof.

Other peptides that inhibit angiogenesis and correspond to fragments of laminin, fibronectin, procollagen, and EGF have also been described (See, e.g., Cao, 1998, Prog. Mol. Subcell. Biol. 20:161–176). Monoclonal antibodies and cyclic pentapeptides, which block certain integrins that bind RGD proteins (i.e., possess the peptide motif Arg-Gly-Asp), have been demonstrated to have anti-vascularization activities (Brooks et al., 1994, Science 264:569–571; Hammes et al., 1996, Nature Medicine 2:529–533). Moreover, inhibition of the urokinase plasminogen activator receptor by receptor antagonists inhibits angiogenesis, tumor growth and metastasis (Min et al., 1996, Cancer Res. 56: 2428–33; Crowley et al., 1993, Proc Natl Acad Sci. 90:5021–25). Use of such anti-angiogenic agents is also contemplated by the present invention.

In another embodiment, a vector of the invention is administered in combination with a regimen of radiation.

In another embodiment, a vector of the invention is administered in combination with one or more cytokines, which includes, but is not limited to, lymphokines, tumor necrosis factors, tumor necrosis factor-like cytokines, lymphotoxin-α, lymphotoxin-β, interferon-α, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4–1BBL, endothelial monocyte activating protein or any fragments, family members, or derivatives thereof, including pharmaceutically acceptable salts thereof.

In yet another embodiment, a vector of the invention is administered in combination with a cancer vaccine. Examples of cancer vaccines include, but are not limited to, autologous cells or tissues, non-autologous cells or tissues, carcinoembryonic antigen, alpha-fetoprotein, human chorionic gonadotropin, BCG live vaccine, melanocyte lineage proteins (e.g., gp100, MART-1/MelanA, TRP-1 (gp75), tyrosinase, widely shared tumor-specific antigens (e.g., BAGE, GAGE-1, GAGE-2, MAGE-1, MAGE-3, N-acetylglucosaminyltransferase-V, p15), mutated antigens that are tumor-specific (β-catenin, MUM-1, CDK4), nonmelanoma antigens (e.g., HER-2/neu (breast and ovarian carcinoma), human papillomavirus-E6, E7 (cervical carcinoma), MUC-1 (breast, ovarian and pancreatic carcinoma)). Human tumor antigens can be recognized by lymphocytes, such as T cells (See, e.g., Robbins and Kawakami, 1996, Curr. Opin. Immunol. 8:628–36). Cancer vaccines need not be purified preparations.

In yet another embodiment, a vector of the invention is administered in association with a hormonal treatment. Hormonal therapeutic treatments comprise hormonal agonists, hormonal antagonists (e.g., flutamide, tamoxifen, leuprolide acetate (LUPRON), LH-RH antagonists), inhibitors of hormone biosynthesis and processing, and steroids (e.g., dexamethasone, retinoids, betamethasone, cortisol, cortisone, prednisone, dehydrotestosterone, glucocorticoids, mineralocorticoids, estrogen, testosterone, progestins), antigestagens or antiprogestins (e.g., mifepristone, onapristone), and antiandrogens (e.g., cyproterone acetate (ANDROCUR), leuprolide acetate (LUPRON), flutamide (EULEXIN), nilutamide (NILANDRON), bicalutamide (CASODREX), leuprorelin, finasteride (PROSCAR)).

In yet another embodiment, a vector of the invention is used in association with a gene therapy program in the treatment of cancer. In one embodiment, gene therapy with recombinant cells secreting interleukin-2 is administered in combination with a vector of the invention to prevent or treat cancer, particularly breast cancer (See, e.g., Deshmukh et al., 2001, J Neurosurg. 94:287–92).

In a specific embodiment, a cancer is treated by a method comprising administering to a subject in need thereof an effective amount of a vector comprising a heterologous polynucleotide operably linked to one or more regulatory sequences useful for the methods of the invention, and another therapeutic agent; wherein the heterologous polynucleotide comprises a sequence encoding thymidine kinase. In a specific further embodiment, the other therapeutic agent is ganciclovir.

In one embodiment, a vector of the invention is administered, in combination with at least one cancer therapeutic agent, for a short treatment cycle to a cancer patient to treat cancer. The duration of treatment with the cancer therapeutic agent may vary according to the particular cancer therapeutic agent used. The invention also contemplates discontinuous administration or daily doses divided into several partial administrations. An appropriate treatment time for a particular cancer therapeutic agent will be appreciated by the skilled artisan, and the invention contemplates the continued assessment of optimal treatment schedules for each cancer therapeutic agent.

The present invention contemplates at least one cycle, preferably more than one cycle during which a single therapeutic or sequence of therapeutics is administered. An appropriate period of time for one cycle will be appreciated by the skilled artisan, as will the total number of cycles, and the interval between cycles. The invention contemplates the continued assessment of optimal treatment schedules for each vector of the invention and cancer therapeutic agent.

5.6 Pharmaceutical Compositions

Since expression of a cytotoxic or cytostatic gene can have significant therapeutic responses in a subject with a cell-proliferative disorder, the invention provides useful pharmaceutical compositions, treatment courses, and modes of delivery. The vectors of the invention can be incorporated into pharmaceutical compositions suitable for administration.

Accordingly, in one embodiment, a pharmaceutical composition comprises a vector of the invention. In a further embodiment, the pharmaceutical composition additionally comprises a pharmaceutically acceptable carrier.

The phrase "pharmaceutically acceptable carrier" refers to an agent that does not interfere with the effectiveness of the biological activity of a vector of the invention, and which may be approved by a regulatory agency of the Federal government or a state government, or is listed in the U.S. Pharmacopeia or other generally recognized pharmacopeia for use in animals, more particularly for use in humans. As such, a pharmaceutically acceptable carrier is intended to include, but is not limited to, solvents, dispersion media, coatings, antibacterial and antifungal agents, isotonic and absorption delaying agents compatible with pharmaceutical administration. The use of such media and agents for pharmaceutically active substances is well known in the art. Except insofar as any conventional media or agent is incompatible with a vector of the invention, use thereof in the pharmaceutical compositions of the invention is contemplated.

The carrier can be a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents.

These compositions can take the form of, for example, solutions, suspensions, emulsion, tablets, pills, capsules, powders, and sustained-release formulations. The composition can be formulated as a suppository, with traditional binders and carriers such as triglycerides. Examples of suitable pharmaceutical carriers are described in *Remington's Pharmaceutical Sciences* by E. W. Martin. Examples of suitable pharmaceutical carriers are a variety of cationic lipids, including, but not limited to N-(1(2,3-dioleyloxy) propyl)-N,N,N-trimethylammonium chloride ("DOTMA") and diolesylphosphotidylethanolamine ("DOPE").

Liposomes are also suitable carriers for the vectors of the invention. Such compositions should comprise a therapeutically effective amount of the compound, together with a suitable amount of carrier so as to provide the form for proper administration to the subject. The formulation should suit the mode of administration.

Pharmaceutically acceptable salts are prepared from pharmaceutically acceptable, essentially nontoxic, acids and bases, including inorganic and organic acids and bases. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes. Such compositions should comprise a therapeutically effective amount of the compound, together with a suitable amount of carrier so as to provide an appropriate formulation for administration to a subject. For example, oral administration requires enteric coatings to protect the antagonist from degradation within the gastrointestinal tract. In another example, the antagonist can be administered in a liposomal formulation to facilitate transport in circulatory system, effect delivery across cell membranes to intracellular sites, and shield the antagonist from degradative enzymes.

Accordingly, in one embodiment, a pharmaceutical composition comprises a vector of the invention and one or more therapeutic agents and a pharmaceutically acceptable carrier. In a particular embodiment, the pharmaceutical composition comprises a vector of the invention and one or more cancer therapeutic agents and a pharmaceutically acceptable carrier.

In a further embodiment, a pharmaceutical composition comprising a vector of the invention, with or without other therapeutic agents, and a pharmaceutically acceptable carrier, is at an effective dose.

The compositions of the invention can be formulated as neutral or salt forms. Pharmaceutically acceptable salts include those formed with free amino groups, such as for example, those derived from hydrochloric, phosphoric, acetic, oxalic, and tartaric acids, and those formed with free carboxyl groups such as, for example, those derived from sodium, potassium, ammonium, calcium, ferric hydroxides, isopropylamine, triethylamine, 2-ethylamino ethanol, histidine, and procaine.

In a preferred embodiment, the composition is formulated as a pharmaceutical composition in accordance with routine procedures adapted for subcutaneous injection or intravenous administration to humans. Typically, compositions for subcutaneous injection or intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of vector. Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients can be mixed prior to administration.

Selection of a preferred effective dose can be determined by a skilled artisan based upon the consideration of factors which will be known to one of ordinary skill in the art. Such factors include the particular form of a vector of the invention and its pharmacokinetic parameters such as bioavailability, metabolism and half-life, which is established during the development procedures typically employed in obtaining regulatory approval of a pharmaceutical compound. Further factors that can be used to determine an effective dose include the disease to be treated, the benefit to be achieved in a subject, the subject's body mass, the subject's immune status, the route of administration, whether administration of a vector of the invention and/or combination therapeutic agent is acute or chronic, concomitant medications, and other factors known by the skilled artisan to affect the efficacy of administered pharmaceutical agents.

5.7 Modes of Administration

Administration of the pharmaceutical compositions of the invention includes, but is not limited to, injection, inhalation, topical, parenteral, oral, time-release mode, infusion, intravenous, intramuscular, intraperitoneal, intraorbital, intracapsular, intraspinal, intrasternal, intra-arterial, intradermal, transdermal, transmucosal, rectal, depo injection, implantation, intracavitary, intranasal, intratumor, intravesicle (for example, into the bladder), intraventricular, intraocular, and controlled release. A pharmaceutical composition of the invention is formulated to be compatible with its intended route of administration. The skilled artisan can appreciate the specific advantages and disadvantages to be considered in choosing a mode of administration.

Multiple modes of administration are encompassed by the invention. For example, a vector of the invention can be administered by subcutaneous injection, while a combination therapeutic agent is administered by intravenous infusion.

A vector of the invention can be administered before, during and/or after administration of one or more therapeutic agents. In one embodiment, a vector of the invention is first administered to cancer patient, which increases the tumor's sensitivity to subsequent challenge with another cancer therapeutic agent. In another embodiment, a vector of the invention is administered after administration of another cancer therapeutic agent to reduce tumor expression of BCA, which can deter tumor resistance, and thereby prevent relapse or minimization of response to the cancer therapeutic agent. In yet another embodiment, there is a period of overlap between administration of a vector of the invention and other cancer therapeutic agents.

Moreover, administration of one or more vectors of the invention, with or without other therapeutic agents, can occur simultaneously (i.e., co-administration) or sequentially. In one embodiment, a vector of the invention is first administered to increase sensitivity of a tumor to subsequent administration of another cancer therapeutic agent or irradiation therapy. In another embodiment, the periods of administration of one or more types of vectors of the invention, with or without other therapeutic agents, can overlap. For example, a vector of the invention is administered for 14 days, and a second therapeutic agent is introduced beginning on the seventh day of treatment with a vector of the invention, such that treatment with the second therapeutic agent continues beyond the 14-day treatment with the vector.

The vectors of the invention can be administered by direct introduction (e.g., infusion) into a lumen (such as the bladder), space, or duct of the diseased tissue. Examples of these sites of delivery include, but are not limited to, the ventricles of the brain, central canal of the spinal cord, subarachnoid space, submammary space, placenta, amnion, chambers of the eye, renal capsule, pleural cavity, subcapsular space of lymph node, subcutaneous space, peritoneum, intestinal lumen, tunica vaginalis, lumen of the uterus, uterine (Fallopian) tubes, pelvic, peritoneum, mammillary ducts, cystic duct, bile canaliculi, hepatic duct, bile duct, lymphatic ducts (e.g., thoracic duct), pancreatic duct, ejaculatory duct, salivary gland ducts (e.g., parotid duct), ductus epididymus, and ductus (vas) deferens.

Further, a vector of the invention can be delivered via the bloodstream. Intravenous or intra-arterial administration can be particularly effective for tissues or organs having greater permeability of the blood vessels. For example, because the endothelium is "leaky" in the liver, the vector can be delivered to the cells of the liver via the hepatic artery or portal vein where intimate contact of the blood with the liver cells occurs. Alternatively, the vector can be administered in combination with an agent that increases above normal the permeability of the endothelium.

Solutions or suspensions used for parenteral, intradermal, or subcutaneous application can include the following components: a sterile diluent such as water for injection, saline solution, fixed oils, polyethylene glycols, glycerine, propylene glycol (or other synthetic solvents), antibacterial agents (e.g., benzyl alcohol, methyl parabens), antioxidants (e.g., ascorbic acid, sodium bisulfite), chelating agents (e.g., ethylenediaminetetraacetic acid), buffers (e.g., acetates, citrates, phosphates), and agents that adjust tonicity (e.g., sodium chloride, dextrose). The pH can be adjusted with acids or bases, such as hydrochloric acid or sodium hydroxide, for example. The parenteral preparation can be enclosed in ampules, disposable syringes or multiple dose vials made of glass or plastic.

Pharmaceutical compositions adapted for parenteral administration include, but are not limited to, aqueous and non-aqueous sterile injectable solutions or suspensions, which can contain antioxidants, buffers, bacteriostats and solutes that render the compositions substantially isotonic with the blood of an intended recipient. Such compositions can also comprise water, alcohols, polyols, glycerine and vegetable oils, for example. Extemporaneous injection solutions and suspensions can be prepared from sterile powders, granules and tablets. Such compositions should comprise a therapeutically effective amount of a vector of the invention and/or other therapeutic agent, together with a suitable amount of carrier so as to provide the form for proper administration to the subject. The formulation should suit the mode of administration.

Systemic administration can also be by transmucosal or transdermal means. For transmucosal or transdermal administration, penetrants appropriate to the barrier to be permeated are used in the formulation. Penetrants for transmucosal administration are generally known in the art, and include, for example, detergents, bile salts, and fusidic acid derivatives. Transmucosal administration can be accomplished through the use of nasal sprays or suppositories.

Pharmaceutical compositions adapted for transdermal administration can be provided as discrete patches intended to remain in intimate contact with the epidermis for a prolonged period of time. Pharmaceutical compositions adapted for topical administration can be provided as, for example, ointments, creams, salves, suspensions, lotions, powders, solutions, pastes, gels, sprays, aerosols, or oils. A topical ointment or cream is preferably used for topical administration to the skin (such as, for example, for the treatment of melanoma), mouth, eye or other external tissues. When formulated in an ointment, a vector of the invention can be employed with either a paraffinic or a water-miscible ointment base. Alternatively, a vector of the invention can be formulated in a cream with an oil-in-water base or a water-in-oil base.

Pharmaceutical compositions adapted for topical administration to the eye include, for example, eye drops or injectable compositions. In these compositions, a vector of the invention can be dissolved or suspended in a suitable carrier, which includes, for example, an aqueous solvent with or without carboxymethylcellulose.

Pharmaceutical compositions adapted for topical administration in the mouth include, for example, lozenges, pastilles and mouthwashes.

Pharmaceutical compositions adapted for oral administration can be provided, for example, as capsules, tablets, powders, granules, solutions, syrups, suspensions (in aqueous or non-aqueous liquids), edible foams, whips, or emulsions. Tablets or hard gelatine capsules can comprise, for example, lactose, starch, magnesium stearate, sodium saccharine, cellulose, magnesium carbonate, stearic acid, or salts or variants thereof. Soft gelatin capsules can comprise, for example, vegetable oils, waxes, fats, semi-solid, or liquid polyols. Solutions and syrups can comprise, for example, water, polyols and sugars.

Pharmaceutically compatible binding agents, and/or adjuvant materials can be included as part of the composition. The tablets, pills, capsules, and troches can contain any of the following ingredients, or compounds of a similar nature: a binder (e.g., microcrystalline cellulose, gum tragacanth, gelatin), an excipient (e.g., starch, lactose), a disintegrating agent (e.g., alginic acid, Primogel, corn starch), a lubricant (e.g., magnesium stearate, Sterotes), a glidant (e.g., colloidal silicon dioxide), a sweetening agent (e.g., sucrose, saccharin), or a flavoring agent (e.g., peppermint, methyl salicylate, orange flavoring).

A vector of the invention intended for oral administration can be coated with or admixed with a material (e.g., glyceryl monostearate or glyceryl distearate) that delays disintegration or affects absorption of the vector in the gastrointestinal tract. Thus, for example, the sustained release of the vector can be achieved over many hours and the vector can be protected from being degraded within the gastrointestinal tract. Taking advantage of the various pH and enzymatic conditions along the gastrointestinal tract, pharmaceutical compositions for oral administration can be formulated to facilitate release of the vector at a particular gastrointestinal location.

Pharmaceutical compositions adapted for nasal administration can comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration can comprise liquid carriers such as, for example, nasal sprays or nasal drops. These compositions can comprise aqueous or oil solutions of the vector. Compositions for administration by inhalation can be supplied in specially adapted devices including, but not limited to, pressurized aerosols, nebulizers, or insufflators, which can be constructed so as to provide predetermined dosages of the vector.

Pharmaceutical compositions adapted for rectal administration can be prepared in the form of suppositories (e.g., with conventional suppository bases such as cocoa butter and other glycerides) or retention enemas for rectal delivery.

Pharmaceutical compositions adapted for vaginal administration can be provided, for example, as pessaries, tampons, creams, gels, pastes, foams, or spray formulations.

In a preferred embodiment, a pharmaceutical composition of the invention is delivered by a controlled-release system. Such carriers can be a controlled release formulation, which includes, but is not limited to, implants and microencapsulated delivery systems. For example, the pharmaceutical composition can be administered using intravenous infusion, an implantable osmotic pump, a transdermal patch, liposomes, or hydrogels.

Accordingly, in one embodiment, a pump can be used to administer a vector of the invention to a subject (See, e.g., Langer, 1990, Science 249:1527–33; Sefton, 1987, CRC Crit. Ref. Biomed. Eng. 14:201; Buchwald et al., 1980, Surgery 88:507; Saudek et al., 1989, N. Encl. J. Med. 321:574). In another embodiment, the vector can be delivered in a vesicle, in particular a liposome (See, e.g., Langer, Science 249:1527–33 (1990); Treat et al., 1989, in *Liposomes in the Therapy of Infectious Disease and Cancer*, Lopez-Berestein and Fidler (eds.), Liss, N.Y., pp. 353–65; Lopez-Berestein, ibid., pp. 317–27; International Patent Publication No. WO 91/04014; U.S. Pat. No. 4,704,355). Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In another embodiment, polymeric materials can be used to administer a vector of the invention to a subject (See, e.g., *Medical Applications of Controlled Release*, Langer and Wise (eds.), CRC Press: Boca Raton, Fla., 1974; *Controlled Drug Bioavailability, Drug Product Design and Performance*, Smolen and Ball (eds.), Wiley: N.Y. (1984); Ranger and Peppas, 1953, J. Macromol. Sci. Rev. Macromol. Chem. 23:61; Levy et al., 1985, Science 228:190; During et al., 1989, Ann. Neurol. 25:351; Howard et al., 1989, J. Neurosurg. 71:105).

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In a particular embodiment, a vector of the invention can be administered using a biodegradable polymer having reverse thermal gelatin properties (See, e.g., U.S. Pat. No. 5,702,717).

In yet another embodiment, a controlled release system can be placed in proximity of the target. For example, a micropump can deliver controlled doses directly to a tumor, thereby requiring only a fraction of the systemic dose (See, e.g., Goodson, 1984, in *Medical Applications of Controlled Release*, vol. 2, pp. 115–138).

In one embodiment, it may be desirable to administer a vector of the invention locally to the area in need of treatment. Such administration can be achieved, for example, by local infusion during surgery, topical application (e.g., in conjunction with a wound dressing after surgery), injection, catheter, suppository, or implant. An implant can be of a porous, non-porous, or gelatinous material, which includes membranes (e.g., sialastic membranes) or fibers.

Pharmaceutical compositions suitable for injectable use include sterile aqueous solutions, or dispersions, or sterile powders (for the extemporaneous preparation of sterile injectable solutions or dispersions). For intravenous administration, suitable carriers include physiological saline, bacteriostatic water, Cremophor EL™ (BASF; Parsippany, N.J.) or phosphate buffered saline ("PBS"). The carrier can be a solvent or dispersion medium comprising, for example, water, ethanol, polyol (e.g., glycerol, propylene glycol, liquid polyetheylene glycol), and suitable mixtures thereof.

The proper fluidity can be maintained, for example, by the use of a coating such as lecithin, by the maintenance of the required particle size in the case of dispersion, or by the use of a surfactant. Prevention of the action of microorganisms can be achieved by various antibacterial and antifungal agents, such as for example, parabens, chlorobutanol, phenol, ascorbic acid, and thimerosal. It can be preferable to include in the composition isotonic agents, such as for example, sugars, polyalcohols (e.g., mannitol), sorbitol, and sodium chloride. Prolonged absorption of the injectable compositions can be brought about by including in the composition an agent which delays absorption such as, for example, aluminum monostearate and gelatin.

Sterile injectable solutions can be prepared by incorporating the required amount of a vector of the invention in an appropriate solvent. In the case of sterile powders for the preparation of sterile injectable solutions, compositions containing a vector of the invention can be lyophilized.

For administration by inhalation, the compounds are delivered in the form of an aerosol spray from a pressurized container or dispenser which comprises a suitable propellant, e.g., a gas such as carbon dioxide, or a nebulizer.

Oral or parenteral compositions can be formulated in dosage unit form for ease of administration and uniformity of dosage. Dosage unit form as used herein refers to physically discrete units suited as unitary dosages for the subject to be treated, such that each unit contains a predetermined quantity of a vector of the invention, which is calculated to produce the desired therapeutic effect, and a pharmaceutical carrier. The skilled artisan will appreciate that dosage unit forms are dependent on the unique characteristics of the vector, the particular therapeutic effect to be achieved, and the limitations inherent in the art of compounding such a vector for human administration.

The skilled artisan will appreciate that certain factors may influence the dose necessary to effectively treat a subject, which factors include, but are not limited to, previous treatment regimens, severity of the disease or disorder, general health and/or age of the subject, and concurrent diseases. Moreover, treatment of a subject with a therapeutically effective amount of a vector of the invention can include a single treatment or, preferably, can include a series of treatments. Changes in dosage may result and become apparent from the results of diagnostic assays.

5.8 Kits

The vectors of the invention can be included in a container, pack, or dispenser together with instructions for administration. Accordingly, a kit of the invention can comprise one or more vectors of the invention. Such kits can further comprise, in one or more containers, other cancer therapeutic agents and/or reagents useful for enhancing delivery of the vector to the target tissue.

In a one embodiment, a kit useful for treating cancer in a subject in need of such treatment has, in one or more containers, a vector comprising a heterologous polynucleotide encoding a cytotoxic or cytostatic agent operatively linked to a transcriptional regulatory sequence of the invention. In a particular embodiment, a kit useful for treating cancer in a subject in need of such treatment comprises a package, in the form of a sterile-filled vial or ampule, that contains a vector comprising a heterologous polynucleotide, encoding a product causing a cytotoxic or cytostatic effect in a cancer cell or a vector-releasing cell, operatively linked to a transcriptional regulatory sequence.

Compositions adapted for parenteral administration can be packaged in unit-dose or multi-dose containers (e.g., sealed ampules, sealed vials). These compositions can be stored in a liquid carrier (e.g., sterile saline). Alternatively, these compositions can be stored lyophilized, which may require the addition of a sterile liquid carrier (e.g., sterile saline) prior to use.

In one embodiment, the kit contains a vector comprising a heterologous polynucleotide (the expression of which causes a cytotoxic or cytostatic effect in a cancer cell) operatively linked to a transcriptional regulatory sequence, as an administration-ready formulation, in either unit dose or multi-dose amounts, wherein the package incorporates a label instructing use of its contents for the treatment of cancer.

Alternatively, and according to another embodiment of the invention, the package provides a sterile-filled vial or ampule containing such a vector-releasing cell or cell line. For storage and transport, the vector-releasing cell or cell line should be frozen. Optionally, the package can also contain media and reagents for culturing the vector-releasing cell or cell line.

The invention having been described, the following examples are offered only by way of illustration and not limitation. The present invention may be better understood by reference to the following non-limiting Examples, which are provided only as exemplary of the invention. The following examples are presented to more fully illustrate the preferred embodiments of the invention. They should in no way be construed, however, as limiting the broader scope of the invention.

6. EXAMPLES

6.1 Example 1

H19 Regulatory Sequences Facilitate Expression of a Heterologous Polynucleotide in Tumor Cell Lines This section describes the construction of a variety of expression vectors containing a CAT reporter gene placed under the control of H19 transcriptional regulatory sequences and their transfer into several different bladder cancer cell lines.

6.1.1 Materials and Methods

Cell Lines and Transfections. Bladder cancer cell lines HT-1376, EJ28, T24P, 1197 and UM-UC-3 were obtained from the American Type Culture Collection (ATCC) and maintained according to ATCC recommendations.

Transient transfections were carried out using a calcium phosphate precipitation transfection method. Precipitants (containing 7 μg plasmid) were added in 1 ml of media to $0.3 \times 10^6$ cells in 30 mm dishes. After 16 hours, transfection media was removed and fresh media added. Cells were harvested 24–96 hours after transfection and CAT activity determined using the butyryl-CoA organic phase extraction procedure (Sambrook et al., 1989). An aliquot of the organic upper phase (100 μl) was transferred to a scintillation well containing 3 ml of scintillation fluid and counted.

Construction of Expression Vectors. Plasmids pCAT-basic (containing a CAT reporter gene preceded by a multiple cloning site), pCAT-promoter (containing the CAT reporter gene under the control of an SV40 promoter), pCAT-enhancer (containing the SV40 enhancer downstream of the CAT reporter gene, and a multiple cloning site for insertion of a promoter upstream of the CAT reporter gene) and pCAT-control (containing the CAT reporter gene under control of both the SV40 promoter and enhancer) were all obtained commercially from Promega (Madison, Wis.).

To construct the plasmid pH19E, containing the CAT reporter gene under the control of the H19 promoter, the H19 promoter region (SEQ ID NO:1) was first cloned into pBluescript II SK+ (Promega). A heterologous polynucleotide containing the H19 promoter sequence was amplified from human placenta DNA using primers ESPCR21: CGGTTCCCCACTTCCCCAGTTT (SEQ ID NO:6) and ESPCR22: CGGAAGTCGACAACCCTCACCAAAGGC-CAAGGT (SEQ ID NO:7). The PCR product was end-polished with Klenow enzyme and cloned into the EcoRV site of pBluescript II SK+. The inserted DNA was verified by digestion with the internally cutting enzymes PvuII, EcoRI and ApaI. The orientation of the promoter was opposite that of the lacZ coding region of the vector. The promoter region was then excised by cleavage with HindIII and PstI, and the resulting approximately 0.9 kb fragment was inserted into the HindIII-PstI sites of pCAT-basic to produce pH19E.

Expression plasmids containing the H19 enhancer region inserted in both orientations downstream of the H19 promoter/CAT reporter gene were constructed as follows. A 5 kb SacI fragment containing the H19 downstream enhancer (from +6.0 kb to +11 kb relative to the start of H19 transcription) was cloned into the SacI site of pUC19. This enhancer fragment was then excised with EcoRI and HindIII and ligated into the EcoRI-HindIII sites of pBluescript II SK+ to create pBhH19En-Sa. pBhH19En-Sa was partially digested with BamHI, and the 5 kb fragment containing the H19 enhancer (and an internal BamHI site) was cloned into the BamHI site downstream of the H19 promoter/CAT reporter gene in pH19E. Plasmids containing the H19 enhancer in both the direct (pH19EH19D) and reverse (pH19EH19R) orientations were generated.

6.1.2 Results and Discussion

Five different bladder cancer cell lines HT-1376, EJ28, T24P, 1197 and UM-UC-3 were each transfected with pCAT-basic (designated P-E in FIG. 2), pCAT-control (designated pSV40ESV40 in FIG. 2), pH19E, pH19EH19D and pH19EH19R. The expression results of each construct are presented in FIGS. 3A–3E. In each cell line, the highest level of CAT activity was observed with the pCAT-control plasmid containing both the SV40 enhancer and SV40 promoter. This construct served as a positive control, as SV40 regulatory sequences have been established as inducers of gene expression. However, SV40 regulatory sequences are not tumor cell-specific in their ability to induce gene expression. Cell lines transfected with pH19E, containing the CAT reporter gene under the control of the H19 promoter, also exhibited significantly increased expression of CAT over background. The level of induction of CAT activity by the H19 promoter ranged from five fold in the HT-1376 cell line to ten fold in the UM-UC-3 cell line. Addition of the H19 enhancer to the H19 promoter/CAT reporter gene constructs further increased levels of expression in certain cell lines. For example, in cell lines EJ28, T24P and 1197, the H19 enhancer significantly increased expression from the H19 promoter/CAT reporter gene. However, the orientation of the enhancer gave different results in different cell lines. In cell lines HT-1376 and UM-UC-3, the enhancer had little or no effect on expression.

The results demonstrate that the human H19 promoter region can direct the expression of an operatively linked heterologous reporter gene in a wide variety of bladder cancer-derived cell lines. In some bladder cancer-derived cell lines, the H19 enhancer can further increase expression of a reporter gene under the control of H19.

6.2 Example 2

A Toxin Gene Under the Control of H19 Regulatory Sequences 6.2.1 Materials and Methods The expression constructs described above in Section 6 can be modified to express a sequence encoding a toxic product or a prodrug instead of CAT. For example, the sequence encoding the CAT gene product is removed and replaced with a sequence encoding herpes simplex virus thymidine kinase (HSV-TK) using standard cloning methods that are well known in the art.

The H19/prodrug expression plasmids are transfected into bladder cancer-derived cell lines as described in Section 6. When transfected into bladder cancer cell lines, an H19/HSV-TK expression plasmid induces bladder cancer cell specific cytotoxicity in the presence of ganciclovir.

6.3 Example 3

Expression of H19 in a Mouse Model of Chemically Induced Bladder Carcinoma

6.3.1 Materials and Methods

Seventy-five week old female C3H/He mice (Charles River) were housed at 6 mice per cage and allowed to acclimatize in an air-conditioned room with a 12 hour light/12 hour dark cycle. At 8 weeks of age, the experiment was begun and the mice divided arbitrarily into a control group (10 mice) and experimental group (60 mice). The experimental group of mice were given 0.05% N-butyl-N-(4-hydroxybutyl)nitrosamine (BBM) (Tokyo Kasei Kogyo Co. Ltd., Tokyo, Japan) dissolved in their drinking water ad libitum. Control mice were given tap water. Animals from both groups were killed at 4, 8, 12, 16, 20 and 26 weeks after the start of the experiment. The bladders were excised, fixed, and embedded in paraffin blocks using standard procedures.

Preparation of probe. A 2.1-kb fragment containing the mouse H19 coding region was subcloned into the pBluescript II KS plasmid (Stratagene, La Jolla, Calif.) behind the T7 and T3 RNA polymerase binding sites. [$^{35}$S]-labeled antisense H19 RNA was produced in vitro from HindIII-linearized plasmid DNA using T7 polymerase (Boehringer Mannheim) and an Amersham RPN 2006 kit. In vitro-generated transcripts had a specific activity of $10^7$ cpm/μg. Sense H19 mRNA, prepared with T3 polymerase (Boehringer Mannheim) and EcoRI-linearized template, was used as a control.

In situ hybridization. Paraffin wax sections (5 μM) of formalin fixed tissues were mounted on microscope slides coated with 3-aminopropyltriethoxylane (Tespa, Sigma) and dried overnight at 37° C. Sections were dewaxed with xylene, fixed with 4% paraformaldehyde, and then treated with proteinase K (Sigma). Slides were acetylated to reduce non-specific binding of the probe and dehydrated through an ethanol series.

[$^{35}$S]-labeled RNA probes (specific activity of 50,000 cpu/μl) were hybridized essentially as described by Rangini et al., 1991, Mech. Dev. 35:13–24, omitting the thio-AMP step. Slides were exposed to film for 10 days, and counterstained with hematoxylin and eosin. The slides were examined and photographed using a Polyvar (Reichert Jung) microscope under bright and dark field illumination. Controls included hybridization with sense RNA probe and RNase pre-hybridization treatment. Additionally, sections of bladders from adult healthy mice (which do not express H19) and embryonal mouse bladders (which do express H19) served as negative and positive controls, respectively.

6.3.2 Results and Discussion

By 26 weeks, all of the surviving experimental group mice had developed palpable ladder tumors. Extensive expression of H19 was observed in the chemically induced bladder tumors. In contrast, no expression of H19 was detected in normal adult bladder. Accordingly, this mouse model of chemically induced bladder cancer can be used as an animal model to demonstrate the tumor-specific cytotoxicity in vivo of constructs containing an H19 transcriptional regulatory sequence operatively linked to a toxin gene.

6.4 Example 4

Gene Therapy Using H19 Regulatory Sequences to Express a Heterologous Polynucleotide in a Mouse Model of Bladder Carcinoma The H19/toxin or prodrug expression plasmids are incorporated into liposomes (as described by Takashita et al., 1993, J. Clin. Invest. 93:652–651, incorporated herein by reference) for delivery to mouse bladder in vivo. Mice used for this experiment have chemically induced bladder tumors as described above in Section 8.

Briefly, 50 μg of plasmid DNA, dissolved in 500 μl of Optimen's serum-free medium (BRL Life Technologies, Gaithersburg, Md.) is added to 250 μl of Lipofectamine™ (BRL Life Technologies) previously dissolved in 250 μl of water. The mixture is incubated for 30 minutes at room temperature, then diluted in 10 ml of balanced salt solution (BSS(−): 140 mM NaCl, 5.4 mM KCl, 10 mM Tris-HCl, pH 7.6). After pelleting by centrifuging the solution at 15,000 rpm for 30 minutes, the liposomes are resuspended in 1 ml of BSS(−) containing 1 mM $CaCl_2$.

Approximately 0.2 mls of the concentrated liposomes are administered to mice that have chemically induced bladder tumors via catheter. A control group of mice with bladder tumors receive liposomes with no DNA or with a construct containing an irrelevant gene under the control of the H19 transcriptional regulatory sequences. At defined timepoints, mice from each group are sacrificed and the bladders excised, fixed, and embedded in paraffin blocks using standard procedures.

Alternate sections are processed for in situ hybridization using either the H19 probe, as described above, or a probe to the coding sequence of Pseudomonas toxin gene. Additionally, the size, number, and necrosis of tumors are compared between the control and experimental groups. Expression of Pseudomonas toxin is found to co-localize with expression of H19 in the bladder tumors from the experimental group of mice. Additionally, the bladder tumors in the experimental group of mice are reduced in size and necrotic as compared to the bladder tumors in the control group of mice.

6.5 Example 5

Expression from the IGF-2 P3 and IGF-2 P4 Promoters in Tumor Cell Lines

6.5.1 Materials and Methods

In this experiment, a variety of expression constructs containing the luciferase reporter gene placed under the control of one of the four different IGF-2 promoters were constructed and transferred into several different bladder cancer cell lines. The following human IGF-2 promoter/luciferase constructs were made:

| Plasmid Construct | IGF-2 Gene Nucleotide Sequence | Promoter |
|---|---|---|
| Hup1 | −980 to +54 | Promoter 1 |
| Hup2 | −379 to +271 | Promoter 2 |
| Hup3 | −1229 to +140 | Promoter 3 |
| Hup4 | −546 to +102 | Promoter 4 |

The IGF-2 promoter sequences are described in Sussenbach et al., 1992, Growth Reg. 2:1–9, incorporated herein by reference in its entirety. The luciferase reporter vector is commercially available from Promega, Madison, Wis. (catalog #E1641).

6.5.2 Results and Discussion

The resulting expression plasmids were transfected into human bladder cancer cell lines HT-1376, EJ28, T24P, 1197 and UM-UC-3 as described above in Section 6. Luciferase activity was assayed using a commercial kit (Promega, Madison, Wis., catalog #E1500). The results, shown in FIGS. 4A–4E, demonstrate that the IGF-2 P4 promoter directed the expression of the luciferase reporter gene in each bladder cancer cell line tested. In cell line 1197, the IGF-2 P3 promoter also directed the expression of the luciferase reporter gene. In subsequent experiments, IGF-2 P3 and P4 promoters were shown to direct expression of luciferase gene expression in other tumor cell lines, including choriocarcinoma cells and rhabdomyosarcoma cells.

6.6 Example 6

H19 Promoter and IGF-2 Promoter Function with H19 Enhancer to Facilitate Expression of a Heterologous Polynucleotide 6.6.1 Materials and Methods Four luciferase reporter vectors, pGL3-Basic, pGL3-Promoter, pGL3-Enhancer and pGL3-Control were obtained from Promega. These vectors were transfected into cultured cell lines using several different transfection reagents, including lipofectamine (Gibco/BRL), fugene (Boehringer), the Perfect Transfection Kit of 8 different lipids reagents (Invitrogen), TFX-10, TFX-20, transfast (Promega), and the calcium phosphate method (Gorman et al., 1982, Mol. Cell. Biol. 2:1044–1051).

The H19 promoter cloned into the EcoRV site of pBluescript II SK (pbh19p #1) is described in Section 6.1, supra. The H19 promoter was excised by cleaving with SmaI and HindIII, and the resulting 0.9 kb fragment was inserted into the SmaI-HindIII sites of pGL3-Basic vector to produce the Luc-pbh19 construct.

The H19 promoter region from nt −819 to +14 was amplified by PCR from the pbh19p #1 plasmid, using primers 5'-ATATGGTACCGACAACCCTCACCAAAG-3' (upstream, SEQ ID NO:8) and 5'-ATATAAGCTTCTTCTC-CCTCACCCTGCTC-3' (downstream, SEQ ID NO:9). The resulting PCR product was digested with KpnI and HindIII, and ligated into the KpnI-HindIII sites of pGL3-Basic vector, yielding the Luc-PBH19 construct. This PCR-generated H19 promoter was sequenced in both directions by automated dye-terminator-cycle sequencing (ABT Prism 377 DNA sequencer, Perkin Elmer). FIG. 5 shows the nucleotide sequence of the H19 promoter (SEQ ID NO:2) generated by PCR.

The 5-kb H19 downstream enhancer described in Section 6, supra, was digested with DamH to yield two fragments of 4.1 kb and 0.9 kb at the 3' end. The Luc-PBH19–0.9EH19 and Luc-PBH19–4EH19 constructs were produced by inserting the 0.9-kb and 4.1-kb BamHI fragments of the H19 enhancer into the BamHI site of Luc-PBH19 plasmid, respectively. The enhancer sequences were positioned downstream of the H19 promoter/luciferase reporter gene.

The 0.9-kb BamHI enhancer fragment was ligated into the BamHI site of pGL-Basic vector to produce the Luc-0.9EH19 vector. The H19 promoter of the pbh19p #1 plasmid was excised with KpnI and BamHI, and ligated into the KpnI-BglII sites of the Luc-0.9EH19 construct, yielding the Luc-pbh19–0.9EH19 expression construct which contained the promoter clones as described in Section 6, supra, and the 0.9-kb enhancer downstream of the H19/Luc reporter gene.

Expression vectors, designated Hup-1, Hup-2, Hup-3, and Hup-4, and containing the luciferase gene under the control of the human IGF-2 promoters P1, P2, P3 and P4, respectively, were constructed as described in Sussenbach et al., 1992, Growth Reg. 2:1–9. A 512-bp region of P4 was amplified by PCR from the Hup-4 construct using primers 5'-ACAGGTACCTCTAGAGTCGACCT-3' (upstream, SEQ ID NO:10) and 5'-ATATAAGCTTGCTCCCATCCTGCA-3' (downstream, SEQ ID NO:11). The resulting PCR product was digested with KpnI and Hind III, and ligated into the KpnI-Hind III site of the reporter gene vector pGL3-Basic to produce the Luc-P4 reporter gene vector.

Expression vectors comprising the IGF-2 P4 promoter and an H19 enhancer were also prepared. A 2-kb BamHI enhancer fragment derived from the 4.1-kb fragment previously described was cloned into the BamHI site of the Luc-P4 construct, producing the Luc-P4–2EH19 expression vector.

H19 enhancers of 0.9 kb, 2 kb and 4.1 kb were sequenced using automated DNA sequencing. The nucleotide sequence of the 0.9-kb enhancer is shown in FIG. 6 (SEQ ID NO:3). The nucleotide sequence of the 2-kb enhancer is shown in FIGS. 7A and 7B (SEQ ID NO:4). The nucleotide sequence of the 4.1-kb enhancer is shown in FIGS. 8A–8C (SEQ ID NO:5).

6.6.2 Results and Discussion

When several transfection reagents were used to introduce four luciferase gene-containing vectors into cultured cell lines, calcium phosphate precipitation produced the highest transfection efficiency for most of the cell lines tested. Therefore, calcium precipitation was subsequently used to transfect various expression vectors. In addition, increased concentration of plasmid DNA did not inhibit transfection efficiency, even when plasmid DNA was used at concentrations above the plateau.

The bladder cancer cell line 5637, the hepatocellular carcinoma (HCC) cell line Huh7, and the kidney tumor cell line 293T were each transfected with different constructs comprising the luciferase reporter gene under the control of the H19 promoter or IGF-2 P4 promoter, in combination with an H19 enhancer.

Cells transfected with Luc-ph19 and Luc-PH19 comprising the reporter gene and an H19 promoter exhibited increased gene expression over the background (FIGS. 9A–9C). The construct Luc-PH19 comprising the PCR-generated promoter demonstrated a higher activity than the Luc-ph19 in each cell line tested. Addition of the 0.9-kb H19 enhancer fragment to the Luc-ph19 reporter vector (Luc-ph19–0.9EH19) further increased levels of expression from two fold to four fold in the 5637 and 293T cell lines, respectively.

The IGF-2 P4 promoter also increased over background, luciferase expression in all cell lines over background. Addition of the 2-kb H19 enhancer fragment to the Luc-P4 expression vector enhanced the P4 promoter activity. The level of induction of luciferase activity by the 2-kb enhancer fragment ranged from two fold in the 293T cell line to six fold in the Huh7 cell line, whereas the enhancer only marginally enhanced the promoter activity in 5673 cells.

FIGS. 10A–10E shows expression of the construct Luc-ph19–4EH19 comprising the PCR-generated H19 promoter and the 4.1 kb H19 enhancer fragment. The enhancer greatly increased the activity of the promoter by 3fold to 28 folds in all cell lines (except for the 5637 cell line).

6.7 Example 7

Gene Therapy by Direct Administration to the Tumor using H19 Regulatory Sequences to Express a Diphtheria Toxin—In Vivo Results

6.7.1 Experimental

A model of transplantable mouse bladder was used. Mouse bladder carcinoma cells ($0.2 \times 10^6$ MBT-2-T50) were injected into the subcutaneous space in the dorsa of 6-week-old C3H/H3 female mice. The animals were randomly separated into two groups of the same size (n=15) and a third group of n=3 animals.

Ten days after inoculation with the bladder carcinoma cells, the tumors in mice of group 1 (n=15) were directly injected with 50 μg of a plasmid, containing a diphtheria toxin gene under the control of the human H19 promoter (DTA-PBH19). The plasmid was prepared as described above and was administered as a calcium phosphate precipitate. Tumors from group 2 (n=15) were injected with 50 μg of the plasmid containing the luciferase reporter gene (Luc-PBH19). In each case, after injection of the plasmid into the tumor, the needle was embedded in the tumor for 30 seconds to prevent back diffusion.

Groups 1 and 2 received a total of three injections (i.e., a second injection of the toxin-containing plasmid or reporter-containing plasmid was administered two days after the first injection, and the third injection of the same plasmids was administered two days after the second injection). Group 3 (n=3) served as untreated control. Twenty-one days following inoculation with the cells, all the mice were sacrificed and the subcutaneous tumors were removed. The tumor size was regularly measured before each treatment.

Samples of the tumor tissue were fixed in a 4% buffered formaldehyde solution and processed for histological examination. A sample of the tumors from group 2 was also frozen using liquid nitrogen and stored at −80° C. for later luciferase determination.

6.7.2 Results

Results are shown in Table 1 below.

TABLE 1

| Treatment Group | Number of animals (N) | Mean tumor wet weight (grams) | Reduction of mean tumor weight (%) |
|---|---|---|---|
| DT-A-Luc-PBH19 (control) | 11 | 2.64 ± 1.54 | — |
| DTA-PBH19 | 11 | 1.58 ± 1.0 | 40 |

The results indicate that in mice treated with the toxin-containing plasmid (DT-A-PBH19), the mean weight of the tumor was 40% lower than the mean weight of the tumor of the mice treated with the plasmid containing the reporter gene (DT-A-Luc_PBH19). Histological analysis also showed that tumors treated with the toxin-containing plasmid had a higher degree (50%) of tumor necrosis as compared to control groups.

6.8 Example 8

Gene Therapy by Direct Administration to the Tumor using H19 Regulatory Sequences to Express a Herpes Simplex Virus Thymidine Kinase—In Vivo Results

6.8.1 Experimental

Transplantable mouse bladder carcinoma was induced as described in section 12 above. Twelve to fifteen days after inoculation with the bladder carcinoma cells, a plasmid containing Herpes simplex thymidine kinase under the control of an H19 transcriptional regulatory sequence ("TK-H19") was injected directly into the tumor as a calcium phosphate precipitate. Mice (n=8) were assigned as either treatment or control groups and received daily i.p. injections of either 100 mg/kg ganciclovir (treatment) or saline (control) for the next five days. Animals were inspected daily and tumor size was measured. Twenty-three days after tumor cell injection, the mice were sacrificed. Tumors were removed, weighed and fixed for histological examination as described in section 12.

6.8.2 Results

Results indicated a significant decrease in tumor size for the treated animals as compared to control. Results are shown in Table 2 below and in FIG. 11.

TABLE 2

| Treatment | Number of animals | Mean tumor wet weight (grams) | Reduction of mean tumor weight (1%) |
|---|---|---|---|
| TK-H19 + PBS (control) | 8 | 6.2 ± 3.33 g | — |
| TK-H19 + GCV | 8 | 3.59 ± 1.3 g | 42% |

FIG. 11 shows that the growth rate of tumors in animals receiving ganciclovir treatment was reduced compared to the growth rate of tumors in the control non-treated animals receiving saline.

6.9 Example 9

In Vivo Intralumen Administration using H19 Regulatory Sequences to Express the Luciferase Gene

6.9.1 Experimental

Bladder carcinoma was chemically induced in Wistar rats as described above in Section 8.

One animal, which served as control, was catheterized for intravesicle (intralumenal) delivery of the adenovirus AdGL3Luc ($10^{10}$ viral particles) in which the luciferase (luc) gene is under the control of the SV40 promoter-enhancer from the pGL3Luc control (Promega). Forty-five hours after administration of the substrate luciferin (50 mM, 126 mg/kg) the expression of luc was determined using a Charged Coupled Device ("CCD") camera equipped with a micro-channel plate intensifier system, which is sufficiently sensitive to detect luminescence in a live animal through the overlying tissues.

The other animal received N-butyl-N-(4-hydroxybutyl) nitrosamine ("BBN") for seventeen weeks to induce of bladder cancer. This treated animal was intravesically (intralumenally) administered with 50 μg of a calcium phosphate precipitate of the Luc-PBH19 plasmid, which carries the luc gene under control of an H19 promoter. Thirty hours after transfection with the Luc-PBH19 plasmid and, following administration of luceferin (50 mg, 126 mg/kg), luc expression was detected using a CCD camera as described above. The animal was inspected again 53 hours after inoculation with the Luc-PBH19 plasmid.

6.9.2 Results

The results are shown in FIGS. 12A (control), 12B (treated; assayed 30 hours after inoculation) and 12C (treated; assayed about 52 hours after inoculation). As demonstrated in the figures, intravesicle (intralumenal) administration of the control plasmid wherein the SV40 promoter-enhancer is linked to the luc gene, which does not lead to tumor-specific expression, resulted in non-specific expression of luciferase throughout the bladder (FIG. 12A). In contrast, intravesicle (intralumenal) administration of the plasmid in which the luc gene is under control of an H19 promoter, resulted in luciferase activity only at the site of the tumor (FIG. 12B). The luciferase activity diminished about 52 hours after inoculation with the vector probably due to degradation of the vector (FIG. 12C).

This example clearly indicates that intralumenal administration of a gene therapy vector of the invention effectively targets the cells of interest, and demonstrates tumor-specific expression of a heterologous polynucleotide under the control of a transcriptional regulatory sequence comprising an H19 promoter and/or an H19 enhancer in vivo.

6.10 Example 10

Treatment of Bladder Cancer with a Vector Expressing a Cytotoxic Gene Under the Control of an H19 Regulatory Sequence

6.10.1 Experimental

Sixty 48-week-old Wistar rats were placed in plastic cages in groups of five and were given food and water ad libitum. Bladder carcinoma was chemically induced by BBN (Tokyo Kasai, Tokyo, Japan) administered, for 23 weeks, by dissolvent in the drinking tap water to give a final concentration of 0.05%. Following BBN administration, plain tap water was administered for the last three weeks of the experiment. Twenty rats served as control and were not treated.

The remaining forty rats were anesthetized with an intraperitoneal injection of 4% chloral-hydrate solution (0.8 cc/100 g). A lower abdominal midline incision was performed. The abdominal muscles were divided, and the peritoneal cavity opened. The urinary bladder was identified, and punctured with an insulin syringe (1 cc syringe connected to a 27G needle). Urine was aspirated, and the syringe was disconnected from the needle that was left indwelling. Another syringe containing a total volume of 0.05 cc of either 100 μg constructed plasmid containing diphtheria toxin-A (DTA) under control of H19 promoter ("H19-DTA plasmid") as a CaPi precipitate (20 animals), or 100 μg constructed plasmid containing the luciferase gene under control of H19 promoter ("Luc-DTA plasmid") (20 animals), was connected to the needle. The solution was injected slowly into the bladder, the needle removed, and the puncture site pinched with an anatomic tweezer for two minutes. The abdominal muscles were approximated with a 3–0 Vycril suture (non-cutting needle). Before putting the last suture, 1 mg of the antibiotic ciprofloxacin was poured into the peritoneal cavity. The skin was sutured with a 3–0 Vycril suture (cutting needle).

One week later, the animals were sacrificed with intraperitoneal injection of chloral-hydrate overdose. Laparotomy was performed, the abdominal cavity explored, and the bladder removed. The bladder was emptied, and the perivesical tissue dissected away before weighing the bladder. The bladder was halved along the sagittal plane, and the halves were stretched out on a piece of absorbing paper. A digital photograph of the bladder was taken using a digital camera. The digitized image was processed with the Image-Pro Plus software (Media Cybernetics, USA). The surface area of all the tumors was measured with the same software, using a scale included in the film, and expressed in $m^2$. If several tumor sites were found in the same bladder, their total surface area was considered. The total surface area of the stretched bladder was measured as well, and the percentage of bladder surface covered by tumor was calculated. Bladder weight was correlated with tumor surface area using regression analysis (Microsoft Excel 97). A sample of bladder tissue bearing the tumor was fixed in formalin, processed and embedded in paraffin to verify the presence of malignancy.

6.10.2 Results

The tumor size when calculated either by the ratio of tumor-to-bladder surface area, or by calculation of total bladder weight, was reduced on average by 37% and 38% respectively, indicating the efficacy of the intravesical transfection by the Hi 9-DTA plasmid, and the anti-cancer potency of H19-driven DTA expression in bladder tumor cells.

FIG. 13 shows the ratio of tumor surface area to total bladder surface area in BBN-induced untreated animals ("Untreated"), in animal treated with a construct comprising a control, non-cytotoxic gene under the control of an H19 promoter ("H19-Luc") and a construct comprising a cytotoxic gene (diphtheria toxin) under the control of an H19 promoter ("H19-DTA").

7. DEPOSIT OF CLONE

| Clone | ATCC Accession No. | Date of Deposit |
|---|---|---|
| pH19EH19 | 209322 | Oct. 2, 1997 |

8. EQUIVALENTS

The foregoing written specification is sufficient to enable one skilled in the art to practice the invention. Indeed, various modifications of the above-described means for carrying out the invention which are obvious to those skilled in the field of molecular biology, medicine, or related fields are intended to be within the scope of the following claims.

Those skilled in the art will recognize, or through routine experimentation, will be able to ascertain many equivalents to the particular embodiments of the invention described herein. The claimed invention intends to encompass all such equivalents.

9. INCORPORATION BY REFERENCE

All publications cited herein are incorporated by reference in their entirety. All publications, patents and patent applications mentioned in this specification are herein incorporated by reference into the specification to the same extent as if each individual publication, patent or patent application was specifically and individually indicated to be incorporated herein by reference.

What is claimed is:

1. A method for treating cancer comprising administering to a subject in need thereof an effective amount of a vector comprising a heterologous polynucleotide encoding a cytotoxic or cytostatic gene product operably linked to one or more regulatory sequences, wherein the regulatory sequence is derived from an H19, IGF-1 or IGF-2 P4 transcriptional regulatory sequence.

2. A method for reducing cell growth comprising contacting a cancer cell with an effective amount of a vector comprising a heterologous polynucleotide encoding a cytotoxic or cytostatic gene product, operably linked to one or more regulatory sequences, wherein the regulatory sequence is derived from an H19, IGF-1 or IGF-2 P4 transcriptional regulatory sequence.

3. The method of claim 1 or claim 2, wherein the heterologous polynucleotide comprises a sequence encoding a cytotoxic product.

4. The method of claim 3, wherein the cytotoxic product is selected from the group consisting of thymidine kinase, diphtheria toxin, Pseudomonas toxin, ricin, cholera toxin, retinoblastoma gene and p53.

5. The method of claim 1 or claim 2, wherein the heterologous polynucleotide comprises a sequence encoding a cytostatic product.

6. The method of claim 5, wherein the cytostatic product is selected from the group consisting of p21, p27, p53, p53175P, p57, p15, p16, p18, p19, p73, GADD45, APC1, p73RB1, WT1, NF1, and VHL.

7. The method of claim 1 or claim 2, wherein the regulatory sequence comprises an H19 promoter, an H19 enhancer, or both an H19 promoter and H19 enhancer.

8. The method of claim 7, wherein the H19 promoter comprises nucleotides 1 through 830 of SEQ ID NO:1.

9. The method of claim 7, wherein the H19 promoter comprises the sequence of SEQ ID NO:2.

10. The method of claim 7, wherein the H19 enhancer comprises the sequence of the H19 enhancer cloned in plasmid pH19EH19 (ATCC deposit no. 209322).

11. The method of claim 7, wherein the H19 enhancer comprises the sequence of SEQ ID NO:3.

12. The method of claim 7, wherein the H19 enhancer comprises the sequence of SEQ ID NO:4.

13. The method of claim 7, wherein the H19 enhancer comprises the sequence of SEQ ID NO:5.

14. The method of claim 7, wherein the H19 enhancer is placed 3' to the heterologous polynucleotide.

15. The method of claim 1 wherein the cancer is selected from the group consisting of a hepatocellular carcinoma, hepatoblastoma, rhabdomyosarcoma, esophageal carcinoma, thyroid carcinoma, ganglioblastoma, colon carcinoma, breast carcinoma ovarian carcinoma squamous cell bronchogenic carcinoma, cervical carcinoma testicular tumor, lung carcinoma, small cell lung carcinoma, bladder carcinoma, astrocytoma, neuroblastoma.

16. The method of claim 1 wherein the administering is intravesically.

17. The method of claim 16, wherein the administering is into the bladder and wherein the cancer is bladder carcinoma.

18. A pharmaceutical composition comprising an effective amount of a vector comprising a heterologous polynucleotide operably linked to one or more regulatory sequences, wherein the heterologous polynucleotide comprises a sequence encoding a cytotoxic or cytostatic product, and wherein the regulatory sequence is derived from an H19, IGF-1 or IGF-2 P4 transcriptional regulatory sequence.

19. The pharmaceutical composition of claim 18, further comprising a pharmaceutically acceptable carrier.

20. A method for treating cancer, comprising administering to a subject in need thereof an effective amount of a vector comprising a heterologous polynucleotide operably linked to one or more regulatory sequences, wherein the heterologous polynucleotide comprises a sequence encoding a cytotoxic or cytostatic product, and wherein the regulatory sequence is derived from a transcriptional regulatory sequence of an imprinted human gene, that is specifically expressed in the cancer.

21. A method for treating cancer, comprising administering into a tumor of a subject in need thereof an effective amount of a vector comprising a heterologous polynucleotide operably linked to one or more regulatory sequences, wherein the heterologous polynucleotide comprises a sequence encoding a cytotoxic or cytostatic product, and wherein the regulatory sequence is derived from a transcriptional regulatory sequence of an imprinted human gene, that is specifically expressed in the cancer.

22. A method for reducing cell growth comprising the step of contacting a cancer cell with an effective amount of a vector comprising a heterologous polynucleotide operably linked to one or more regulatory sequences, wherein the heterologous polynucleotide comprises a sequence encoding a cytotoxic or cytostatic product, and wherein the regulatory sequence is derived from a transcriptional regulatory sequence of an imprinted human gene, that is specifically expressed in the cancer cell.

* * * * *

SEQUENCE LISTING

<160> NUMBER OF SEQ ID NOS: 15

<210> SEQ ID NO 1
<211> LENGTH: 830
<212> TYPE: DNA
<213> ORGANISM: Homo sapien

<400> SEQUENCE: 1

| | | | | | | |
|---|---|---|---|---|---|---|
| ctgcagggcc | ccaacaaccc | tcaccaaagg | ccaaggtggt | gaccgacgga | cccacagcgg | 60 |
| ggtggctggg | ggagtcgaaa | ctcgccagtc | tccactccac | tcccaaccgt | ggtgccccac | 120 |
| gcgggcctgg | gagagtctgt | gaggccgccc | accgcttgtc | agtagagtgc | gcccgcgagc | 180 |
| cgtaagcaca | gcccggcaac | atgcggtctt | cagacaggaa | agtggccgcg | aatgggaccg | 240 |
| gggtgcccag | cggctgtggg | gactctgtcc | tgcggaaacc | gcggtgacga | gcacaagctc | 300 |
| ggtcaactgg | atgggaatcg | gcctgggggg | ctggcaccgc | gcccaccagg | gggtttgcgg | 360 |
| cacttccctc | tgcccctcag | caccccaccc | ctactctcca | ggaacgtgag | gtctgagccg | 420 |
| tgatggtggc | aggaagggggc | cctctgtgcc | atccgagtcc | ccaggacccc | gcagctggcc | 480 |
| cccagccatg | tgcaaagtat | gtgcagggcg | ctggcaggca | gggagcagca | ggcatggtgt | 540 |
| cccctgaggg | gagacagtgg | tctgggaggg | agaggtcctg | gaccctgagg | gaggtgatgg | 600 |
| ggcaatgctc | agccctgtct | ccggatgcca | aaggaggggt | gcgggaggc | cgtctttgga | 660 |
| gaattccagg | atgggtgctg | ggtgagagag | acgtgtgctg | gaactgtcca | gggcggaggt | 720 |
| gggccctgcg | ggggccctcg | ggagggccct | gctctgattg | gccggcaggg | cagggcggg | 780 |
| aattctggcg | ggccacccca | gttagaaaaa | gcccgggcta | ggaccgagga | | 830 |

<210> SEQ ID NO 2
<211> LENGTH: 833
<212> TYPE: DNA
<213> ORGANISM: Homo sapien

<400> SEQUENCE: 2

| | | | | | | |
|---|---|---|---|---|---|---|
| gacaaccctc | accaagggcc | aaggtggtga | ccgacggacc | cacagcgggg | tggctggggg | 60 |
| agtcgaaact | cgccagtctc | cactccactc | ccaaccgtgg | tgccccacgc | gggcctggga | 120 |
| gagtctgtga | ggccgcccac | cgcttgtcag | tagagtgcgc | ccgcgagccg | taagcacagc | 180 |
| ccggcaacat | gcggtcttca | gacaggaaag | tggccgcgaa | tgggaccggg | gtgcccagcg | 240 |
| gctgtgggga | ctctgtcctg | cggaaaccgc | ggtgacgagc | acaagctcgg | tcaactggat | 300 |
| gggaatcggc | ctgggggggct | ggcaccgcgc | ccaccagggg | gtttgcggca | cttccctctg | 360 |
| cccctcagca | ccccaccct | actctccagg | aacgtgagtt | ctgagccgtg | atggtggcag | 420 |
| gaagggggccc | tctgtgccat | ccgagtcccc | aggacccgc | agctggcccc | cagccatgtg | 480 |
| caaagtatgt | gcagggcgct | ggcaggcagg | gagcagcagg | catggtgtcc | cctgagggga | 540 |
| gacagtggtc | tgggagggag | aagtcctggc | cctgagggag | gtgatggggc | aatgctcagc | 600 |
| cctgtctccg | gatgccaaag | gagggtgcg | ggaggccgt | ctttggagaa | ttccaggatg | 660 |
| ggtgctgggt | gagagagacg | tgtgctggaa | ctgtccaggg | cggaggtggg | ccctgcgggg | 720 |
| gccctcggga | gggccctgct | ctgattggcc | ggcaggcag | ggcgggaat | tctggcgggg | 780 |
| gccacccag | ttagaaaaag | cccgggctag | gaccgaggag | cagggtgagg | gag | 833 |

<210> SEQ ID NO 3
<211> LENGTH: 877

<212> TYPE: DNA
<213> ORGANISM: Homo sapien

<400> SEQUENCE: 3

| | | | | | |
|---|---|---|---|---|---|
| caaggacatg | gaatttcgga | ccttctgtcc | ccaccctctc | tgctgagcct | aggaacctct | 60 |
| gagcagcagg | aaggccttgg | gtctagagcc | tagaaatgga | cccccacgtc | cacctgccca | 120 |
| gcctagaccc | ccagcattga | aggtggtca | gacttcctgt | gagaggaagc | cactaagcgg | 180 |
| gatggacacc | atcgcccact | ccacccggcc | ctgcccagcc | ctgcccagtc | cagcccagtc | 240 |
| cagcccagcc | ctgcccttcc | cagccctgcc | cagcccagct | catccctgcc | ctacccagcc | 300 |
| cagccctgtc | ctgccctgcc | cagcccagcc | cagcccagcc | ctgccctgcc | ctgccctgcc | 360 |
| cttcccagcc | ctgaccttcc | cagccctgcc | cagcccagct | catccctgcc | ctacccagct | 420 |
| cagccctgcc | ctgccctgcc | ctgccctgcc | cagccctacc | cagcccagcc | ctgccctgcc | 480 |
| ctgcccagct | cagccctgcc | caccccagcc | cagcccagcc | cagcatgcgt | tctctggatg | 540 |
| gtgagcacag | gcttgacctt | agaaagaggc | tggcaacgag | ggctgaggcc | accaggccac | 600 |
| tgggtgctca | cgggtcagac | aagcccgag | cctgctcccc | tgccacgggt | cggggctgtc | 660 |
| accgccagca | tgctgtggat | gtgcatggcc | tcagggctgc | tggctccagg | ctgccccgc | 720 |
| cctggctccc | gaggccaccc | ctcttatgcc | atgaaccctg | tgccacaccc | acctctgagc | 780 |
| tgtccccgct | cctgccgcct | gcaccccctg | agcagcccc | tgtgtgtttc | atgggagtct | 840 |
| tagcaaggaa | gggagctcg | aattcctgca | gcccggg | | | 877 |

<210> SEQ ID NO 4
<211> LENGTH: 1960
<212> TYPE: DNA
<213> ORGANISM: Homo sapien
<220> FEATURE:
<221> NAME/KEY: misc_feature
<222> LOCATION: (1016)..(1016)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t

<400> SEQUENCE: 4

| | | | | | |
|---|---|---|---|---|---|
| ccgggtaccg | agctcccagg | aagataaatg | atttcctcct | ctctagagat | gggggtggga | 60 |
| tctgagcact | cagagccaag | ggcgcagtgg | gtccgggcgg | gggccctcct | cggccctccc | 120 |
| aacatggggg | ccaggaggtc | agcccctcaa | cctggacccc | ggctgggtct | cagggaatgg | 180 |
| tctcccccag | tggcccagct | tgcttgtgtt | ttcagatggg | tgtgcatggg | tgtgtgtgtg | 240 |
| tgtgtgtgtg | tgtgtgtgtg | tgtgtgtgtg | tgtgatgcct | gacaagcccc | agagagccaa | 300 |
| agacctgagt | ggagatcttg | tgacttctca | aaaggggggat | tggaaggttc | gagaaagagc | 360 |
| tgtggtcagc | cttgctctcc | cttaaggctg | tggtaaccac | actaggcata | gcataggcct | 420 |
| gcgcccgtc | cctccttccc | tcctccgcgc | ctctcctttc | tctttctccc | ccctctaccc | 480 |
| cgctccctgg | cctgctcctg | gtgacaccgt | tggcccccctt | ccaggctga | gggaagccag | 540 |
| cgggggcccc | ttcctgaaag | cccacctgca | ggccggcttg | ctgggaaggg | gctgctctcg | 600 |
| cagaggctcc | cgcccgccct | gcagccgttt | cctggaagca | gtcgctgtgg | gtattctgtt | 660 |
| ccttgtcagc | actgtgcttg | caaagaaagc | agacactgtg | ctccttgtcc | ttagggagcc | 720 |
| ccgctccatc | acccaacacc | tggctggaca | caggcgggag | gccgggtccg | cggggagcgg | 780 |
| cgcggggctg | gggccggacc | attaaacaca | cacgggcgcc | aggcactgca | ggctcctcct | 840 |

-continued

| | |
|---|---|
| cctcctcctg cccagcgcct ctgctcacag gcacgtgcca agcccctagg ccaggaggcc | 900 |
| agcagtgggt gcagaacaag ctcctgggaa ggggtgcag ggcggacccc cggggagaag | 960 |
| ggctggcagg gctgtggggg acgctgaccg tgggccccac gttgcagaaa actggntgcc | 1020 |
| tggctggaag atgggggaga tgccaagcct ctgaggcagc acgagcaggg tgcatggagg | 1080 |
| ccggggcgcg gggaggctgc actgcagcat gcaccccaaa gcccanaggg agtgagacc | 1140 |
| aggccctgga atcgagaagt agaaaggcgg cttggaggcc tcggaaccgg ctgacctcca | 1200 |
| acagagtggg tctccagcct ggctctgccc tgccgcaggt cccctcccct cattaccagg | 1260 |
| cctagagcct ccagtcccgg tggccccag cccgagggtg aacggcctca ccctgggtcg | 1320 |
| tgggacagag ggcacgttca tcaagagtgg ctcccaaggg acacgtggct gtttgcagtt | 1380 |
| cacaggaagc attcgagata aggagcttgt tttcccagtg ggcacggagc cagcaggggg | 1440 |
| gctgtggggc agcccagggt gcaaggccag gctgtgggc tgcagctgcc ttgggcccca | 1500 |
| ctcccaggcc tttgcgggag gtggggaggcg ggaggcggca gctgcacagt ggccccaggc | 1560 |
| gaggctctca gccccagtcg ctctccgggt gggcagccca agagggtctg gctgagcctc | 1620 |
| ccacatctgg gactccatca cccaacaact taattaaggc tgaatttcac gtgtcctgtg | 1680 |
| acttgggtag acaaagcccc tgtccaaagg ggcagccagc ctaaggcagt ggggacggcg | 1740 |
| tgggtggcgg gcgacggggg agatggacaa caggaccgag ggtgtgcggg cgatggggga | 1800 |
| gatggacaac aggaccgagg gtgtgcgggc gatgggggag atggacaaca ggaccgaggg | 1860 |
| tgtgcgggac acgcatgtca ctcatgcacg ccaatggggg gcgtgggagg ctggggagca | 1920 |
| gacagactgg gctgggctgg gcgggaagga cgggcagatg | 1960 |

<210> SEQ ID NO 5
<211> LENGTH: 4085
<212> TYPE: DNA
<213> ORGANISM: Homo sapien
<220> FEATURE:
<221> NAME/KEY: misc_feature
<222> LOCATION: (1016)..(1016)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t
<220> FEATURE:
<221> NAME/KEY: misc_feature
<222> LOCATION: (2194)..(2194)
<223> OTHER INFORMATION: n is a, c, g, or t
<220> FEATURE:
<221> NAME/KEY: misc_feature
<222> LOCATION: (3235)..(3235)
<223> OTHER INFORMATION: n is a, c, g, or t

<400> SEQUENCE: 5

| | |
|---|---|
| ccgggtaccg agctcccagg aagataaatg atttcctcct ctctagagat gggggtggga | 60 |
| tctgagcact cagagccaag ggcgcagtgg gtccggggcgg gggccctcct cggccctccc | 120 |
| aacatggggg ccaggaggtc agcccctcaa cctggacccc ggctgggtct cagggaatgg | 180 |
| tctcccccag tggcccagct tgcttgtgtt ttcagatggg tgtgcatggg tgtgtgtgtg | 240 |
| tgtgtgtgtg tgtgtgtgtg tgtgtgtgtg tgtgatgcct gacaagcccc agagagccaa | 300 |
| agacctgagt ggagatcttg tgacttctca aaaggggggat tggaaggttc gagaaagagc | 360 |
| tgtggtcagc cttgctctcc cttaaggctg tggtaaccac actaggcata gcataggcct | 420 |
| gcgcccgtc cctccttccc tcctccgcgc ctctcctttc tctttctccc ccctctaccc | 480 |
| cgctccctgg cctgctcctg gtgacaccgt tggccccctt ccagggctga gggaagccag | 540 |

```
cgggggcccc ttcctgaaag cccacctgca ggccggcttg ctgggaaggg gctgctctcg     600
cagaggctcc cgcccgccct gcagccgttt cctggaagca gtcgctgtgg gtattctgtt     660
ccttgtcagc actgtgcttg caaagaaagc agacactgtg ctccttgtcc ttagggagcc     720
ccgctccatc acccaacacc tggctggaca caggcgggag gccgggtccg cggggagcgg     780
cgcggggctg gggccggacc attaaacaca cacgggcgcc aggcactgca ggctcctcct     840
cctcctcctg cccagcgcct ctgctcacag gcacgtgcca agccctagg ccaggaggcc      900
agcagtgggt gcagaacaag ctcctgggaa ggggtgcag gcggacccc cggggagaag       960
ggctggcagg gctgtggggg acgctgaccg tgggcccac gttgcagaaa actggntgcc     1020
tggctggaag atgggggaga tgccaagcct ctgaggcagc acgagcaggg tgcatggagg    1080
ccggggcgcg gggaggctgc actgcagcat gcaccccaaa gcccanaggg agtggagacc    1140
aggccctgga atcgagaagt agaaaggcgc ttggaggcc tcggaaccgg ctgacctcca     1200
acagagtggg gccggccctg gaggcaaaga ggtgcccggg gtccggccct gcctggggga    1260
gctatgtgtc atgggcaagc acaggatat gtagcccgct ctgagcctat ggacccaggg     1320
cagggctgca aggcagggca ggggagacag cacggggag caaggagcag agaggggcc      1380
tcaggctctc ccaggaggaa cattctcccg acaggaggaa gagacggccc agggtgact    1440
gtggggagcc atggtggcag ctgggtcgt ggcagatggg agagaggctg gcgaggtgaa    1500
ggtgcagggg tcaggctct ggggcccaca tgcctgtggg agcaggcagg cccagggctc     1560
tccgccactc cccactcccg cttggctcat aggctgggcc caagggtggg gtgggatgag    1620
caggagatgg ggcccagggg gcaagcaggg ccccaaagac atttagaaaa accggtttat    1680
gcaggcagca ttcagagcag gcggcgtgcg tggcggggc cctgggagca cagagaggca    1740
cacgtagggc ccccgagggg ctccccattg gccggcagtg acatcacccc tgtgtcaaca    1800
gtgatgtctg cagctccggc cagccagggt ttatggagcg agacccagcc cggcctgggc    1860
cctcactccc caggcccaca cactagccca ctgttcaggg tccggggtgg cggcatggcc    1920
tgggggtcct ggcaccgctg ctcctctgcc caccctaact tccccgcatc gcggctgccc    1980
cctctgagcg tccccaacca gtaagtgtgg ggcccagcag gcctgccgtc tcctcctct    2040
tccctctag agaaaacgt ggaggtcctg gggctggggg cgctcatagc cctgtgacac    2100
aggtgcatgg ggtcaggggt cccagaatgg cccctgggaa ggacctcagc tgggccggcg    2160
gctctaggct tcagggtct gtctgcacag gggntagccc ctcccagacc tctgtgaagc     2220
cagtacgggc ctccccctccc tgccccgtgc tctgtccggt gcttcctgga ctgcactgcg    2280
ggccactggt gagagggtgg acagggaagg gccgccgtgg tgcctgttcc tgcccacctg    2340
gctgtgtggt cccctccaag tagggacaac ccttctgagg gcttgggggc accctgggt    2400
tgccagggcc tccagagcc ctgtgagccc ctggggggtc tggcctgatg cccccctcca     2460
cgtccagggc cggctgtggc ccagaacccc agcttcccag caggccggtg tgcggtggtg    2520
acccaggaga ggcctcgcct ccactgaggg gccaccgacc tctgtcagac cacagagacc    2580
cccaaggagt ctgaaggctg agacccgggg ctgggacca ggtgggactt tcccacggag     2640
ccgtccccag gccagctgg ggacacgtcc cccttctctc cagacacacc ctgcctgcca     2700
ccaggacaca ccggcctgtt gggggtctct tttaagtgct tgccactctg aggtgactgt    2760
ccccttttccaa agaggtttct ggggcccagg tgggatgcgt cggcctgagc aggaggatct    2820
gggccgccag gggctgggga ctgtctcctg gggaaggaag cgcctgggag cgtgtgtgct    2880
```

-continued

```
gacccaggac catccaggga ggcccgtctg tggggcaagc gggaagggag cggctggaga    2940
ggcttggccg cccccgccct gcctcccatt ccttagctcc atgcctgtca acctctgtca    3000
cccagtgagt gatgtccagg ggccctggaa aggtcacagc atgtttgagc ggggtgagag    3060 agagggaaa ggcgggggcg gggaaaagta cgtggaggaa gctttaggcc caaggaagga    3120 gacaggggttc tgggagggag ggagccactg gggccgccgg gaaggtccct gcttgctgct    3180
gccacccaga accctcgcct cttagctagc ccccgcagcc ccagcctttc tggcntgtgg    3240
ccctctcccc catccccagg tgtcctgtgc aaccaggcct tggacccaaa ccctcctgcc    3300
ccctcctctc cctcctcacc ctcccaatgc agtggtctcc agcctggctc tgccctgccg    3360
caggtcccct cccctcatta ccaggcctag agcctccagt cccggtggcc cccagcccga    3420
gggtgaacgg cctcaccctg ggtcgtggga cagagggcac gttcatcaag agtggctccc    3480
aagggacacg tggctgtttg cagttcacag gaagcattcg agataaggag cttgtttttcc    3540 cagtgggcac ggagccagca ggggggctgt ggggcagccc aggtgcaag gccaggctgt    3600 ggggctgcag ctgccttggg ccccactccc aggcctttgc gggaggtggg aggcgggagg    3660
cggcagctgc acagtggccc caggcgaggc tctcagcccc agtcgctctc cgggtgggca    3720
gcccaagagg gtctggctga gcctcccaca tctgggactc catcacccaa caacttaatt    3780
aaggctgaat ttcacgtgtc ctgtgacttg ggtagacaaa gccctgtcc aaaggggcag    3840 ccagcctaag gcagtgggga cggcgtgggt ggcgggcgac ggggagatg gacaacagga    3900 ccgagggtgt gcgggcgatg ggggagatgg acaacaggac cgagggtgtg cgggcgatgg    3960
gggagatgga caacaggacc gagggtgtgc gggacacgca tgtcactcat gcacgccaat    4020 gggggggcgtg ggaggctggg gagcagacag actgggctgg gctgggcggg aaggacgggc    4080
agatg                                                                4085
```

<210> SEQ ID NO 6
<211> LENGTH: 22
<212> TYPE: DNA
<213> ORGANISM: Homo sapien

<400> SEQUENCE: 6

```
cggttcccca cttccccagt tt                                              22
```

<210> SEQ ID NO 7
<211> LENGTH: 33
<212> TYPE: DNA
<213> ORGANISM: Homo sapien

<400> SEQUENCE: 7

```
cggaagtcga caaccctcac caaaggccaa ggt                                  33
```

<210> SEQ ID NO 8
<211> LENGTH: 27
<212> TYPE: DNA
<213> ORGANISM: Homo sapien

<400> SEQUENCE: 8

```
atatggtacc gacaaccctc accaaag                                         27
```

<210> SEQ ID NO 9
<211> LENGTH: 29
<212> TYPE: DNA
<213> ORGANISM: Homo sapien

<400> SEQUENCE: 9

```
atataagctt cttctccctc accctgctc                                              29

<210> SEQ ID NO 10
<211> LENGTH: 23
<212> TYPE: DNA
<213> ORGANISM: Homo sapien

<400> SEQUENCE: 10
acaggtacct ctagagtcga cct                                                    23

<210> SEQ ID NO 11
<211> LENGTH: 24
<212> TYPE: DNA
<213> ORGANISM: Homo sapien

<400> SEQUENCE: 11
atataagctt gctcccatcc tgca                                                   24

<210> SEQ ID NO 12
<211> LENGTH: 14
<212> TYPE: PRT
<213> ORGANISM: Artificial
<220> FEATURE:
<223> OTHER INFORMATION: synthetic

<400> SEQUENCE: 12

Ser Ala Thr Leu Asp Ala Leu Leu Ala Ala Leu Arg Arg Ile
1               5                   10

<210> SEQ ID NO 13
<211> LENGTH: 14
<212> TYPE: PRT
<213> ORGANISM: Artificial
<220> FEATURE:
<223> OTHER INFORMATION: synthetic

<400> SEQUENCE: 13

Ser Ala Thr Leu Asp Ala Leu Leu Ala Ala Leu Gly Gly Ile
1               5                   10

<210> SEQ ID NO 14
<211> LENGTH: 14
<212> TYPE: PRT
<213> ORGANISM: Artificial
<220> FEATURE:
<223> OTHER INFORMATION: synthetic

<400> SEQUENCE: 14

Ser Ala Thr Leu Asp Ala Leu Leu Ala Ala Leu Arg Gly Ile
1               5                   10

<210> SEQ ID NO 15
<211> LENGTH: 14
<212> TYPE: PRT
<213> ORGANISM: Artificial
<220> FEATURE:
<223> OTHER INFORMATION: synthetic

<400> SEQUENCE: 15

Ser Ala Thr Leu Gln Ala Leu Leu Ala Ala Leu Arg Arg Ile
1               5                   10
```